(12) United States Patent
Knight et al.

(10) Patent No.: US 8,765,792 B2
(45) Date of Patent: Jul. 1, 2014

(54) INDOLES

(75) Inventors: Steven David Knight, Collegeville, PA (US); William Henry Miller, Collegeville, PA (US); Kenneth Allen Newlander, Collegeville, PA (US); Sharad Kumar Verma, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/990,505

(22) PCT Filed: Nov. 30, 2011

(86) PCT No.: PCT/US2011/062537
§ 371 (c)(1),
(2), (4) Date: May 30, 2013

(87) PCT Pub. No.: WO2012/075080
PCT Pub. Date: Jun. 7, 2012

(65) Prior Publication Data
US 2013/0245016 A1    Sep. 19, 2013

Related U.S. Application Data

(60) Provisional application No. 61/418,470, filed on Dec. 1, 2010.

(51) Int. Cl.
*A61K 31/404* (2006.01)
*C07D 401/12* (2006.01)

(52) U.S. Cl.
USPC .................................. 514/339; 546/277.4

(58) Field of Classification Search
USPC .................................. 546/277.4; 514/339
See application file for complete search history.

(56) References Cited

U.S. PATENT DOCUMENTS

| | | | |
|---|---|---|---|
| 5,330,986 | A | 7/1994 | Shutske et al. |
| 7,087,637 | B2 | 8/2006 | Grandel et al. |
| 2008/0269200 | A1 | 10/2008 | Baldwin et al. |
| 2009/0012031 | A1 | 1/2009 | Chinnaiyan et al. |
| 2013/0053383 | A1 | 2/2013 | Duquenne et al. |
| 2013/0053397 | A1 | 2/2013 | Brackley et al. |
| 2013/0059849 | A1 | 3/2013 | Burgess et al. |

FOREIGN PATENT DOCUMENTS

WO    WO 2012/118812 A2    9/2012

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

* cited by examiner

*Primary Examiner* — Shawquia Young
(74) *Attorney, Agent, or Firm* — Duke M. Fitch; Kathryn A. Lutomski; John Lemanowicz

(57) ABSTRACT

Herein are disclosed indoles of formula (I)

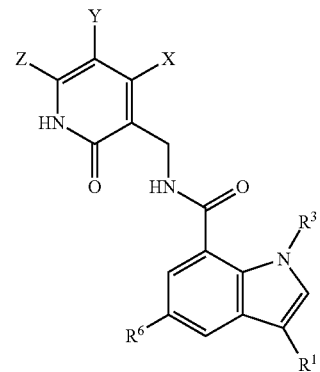

where the various groups are defined herein, and which are useful for treating cancer.

7 Claims, No Drawings

INDOLES

This application is a 371 of International Application No. PCT/US2011/062537, filed 30 Nov. 2011, which claims the benefit of U.S. Provisional Application No. 61/418,470, filed 1 Dec. 2010, which are incorporated herein in their entireties.

FIELD OF THE INVENTION

This invention relates to substituted indoles which inhibit EZH2 and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (enhancer of zeste homolog 2; human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptixe repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism (refs). In addition, EZH2 overexpression in immortalized or primary epithelial cells promotes anchorage independent growth and invasion and requires EZH2 catalytic activity. (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer. The indoles of this invention provide such treatment.

SUMMARY OF THE INVENTION

In a first instance, this invention relates to compounds of formula (I)

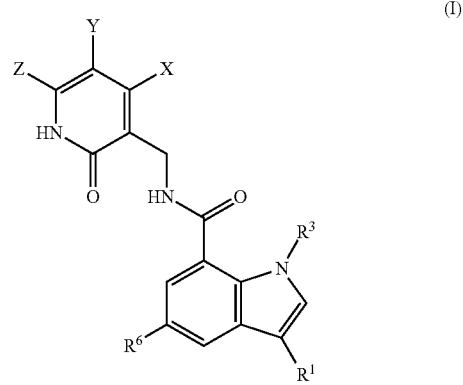

wherein

X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, —$CONR^aNR^aR^b$;

$R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1-C_4$)alkyl, and heteroaryl($C_1-C_4$)alkyl;

wherein any aryl or heteroaryl moiety of said aryl, heteroaryl, aryl($C_1-C_4$)alkyl, or heteroaryl($C_1-C_4$)alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)$((C_1-C_4)$alkyl), —$SO_2(C_1-C_4)$alkyl, —$SO_2NH_2$, —$SO_2NH(C_1-C_4)$alkyl, or —$SO_2N((C_1-C_4)$alkyl)$((C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a salt thereof.

In a further iteration of this invention it relates to a method of treating cancer.

Another aspect of the invention are pharmaceutical preparations comprising compounds of formula (I) and pharmaceutically acceptable excipients.

In a fourth aspect, there is provided the use of a compound of formula (I) or a pharmaceutically acceptable salt or solvate thereof, in the preparation of a medicament for use in the treatment of a disorder mediated by inhibiting EZH2, such as inducing apoptosis in cancer cells.

In a fifth aspect there is provided methods of co-administering the presently invented compounds of formula (I) with another active ingredients.

DETAILED DESCRIPTION OF THE INVENTION

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substitutent group, preferably one to three substituents. The phrase should not be interpreted as duplicative of the substitutions herein described and depicted. Exemplary optional substituent groups include acyl, $C_1-C_6$alkyl, dimethylamino-$C_1-C_3$alkyl, $C_1-C_3$alkylsulfonyl, $C_1-C_3$alkoxy, $C_1-C_3$alkoxycarbonyl, cyano, halogen, haloalkyl, hydroxyl, oxo, amino, piperazine, and nitro.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes. Alkyl may be optionally substituted with one to three groups selected from the group consisting of halogen, amino, methylamino, dimethylamino, cyano, hydroxyl, alkoxy and alkylthio.

The term "alkoxy" as used herein means —O($C_1$-$C_8$alkyl) including —OCH$_3$, —OCH$_2$CH$_3$ and —OC(CH$_3$)$_3$ and the like per the definition of alkyl above.

The term "alkylthio" as used herein is meant —S($C_1$-$C_8$alkyl) including —SCH$_3$, —SCH$_2$CH$_3$ and the like per the definition of alkyl above.

The term "acyloxy" means —OC(O)$C_1$-$C_8$alkyl and the like per the definition of alkyl above.

"Acylamino" means -N(H)C(O)$C_1$-$C_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "$C_3$-$C_8$cycloalkyl" refers to a non-aromatic cyclic hydrocarbon ring having from three to eight carbon atoms. Exemplary "$C_3$-$C_8$cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers, as well as unsubstituted and substituted versions thereof.

As used herein, the term "aryl", unless otherwise defined, is meant aromatic, hydrocarbon, ring system. The ring system may be monocyclic or fused polycyclic (e.g., bicyclic, tricyclic, etc.), substituted or unsubstituted. In various embodiments, the monocyclic aryl ring is C5-C10, or C5-C7, or C5-C6, where these carbon numbers refer to the number of carbon atoms that form the ring system. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl, unless otherwise defined, are described below in the definition of "optionally substituted".

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. Suitable substituents for heteroaryl, unless otherwise defined are described below in the definition of "optionally substituted"

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

While the compounds encompassed by the general structure of formula (I) as defined herein are believed to be useful for inducing apoptosis in cancer cells, some of these compounds are more active that others. In that vein, the following subgroups delineate certain compounds believed to have greater potency or other properties which suggest they may be a better choice for use in therapy, versus other. Those subgroups are represented as follows:

Subgroup A

X and Z are selected from the group consisting of ($C_1$-$C_8$) alkyl, ($C_3$-$C_8$)cycloalkyl, heterocycloalkyl, aryl, heteroaryl, —NR$^a$R$^b$, and —OR$^a$;

Y is H or F;

R$^1$ is selected from the group consisting of ($C_1$-$C_8$)alkyl, ($C_3$-$C_8$)cycloalkyl, heterocycloalkyl, aryl, and heteroaryl;

R$^3$ is selected from the group consisting of hydrogen, ($C_1$-$C_8$)alkyl, cyano, trifluoromethyl, —NR$^a$R$^b$, and halo;

R$^6$ is selected from the group consisting of hydrogen, halo, cyano, trifluoromethyl, amino, ($C_1$-$C_8$)alkyl, ($C_3$-$C_8$)cycloalkyl, aryl, heteroaryl, acylamino; ($C_2$-$C_8$)alkynyl, arylalkynyl, heteroarylalkynyl; —SO$_2$R$^a$; —SO$_2$NR$^a$R$^b$, and —NR$^a$SO$_2$R$^b$;

wherein any ($C_1$-$C_8$)alkyl, ($C_3$-$C_8$)cycloalkyl, ($C_2$-$C_8$) alkynyl, arylalkynyl, heteroarylalkynyl group is optionally substituted by 1, 2 or 3 groups independently selected from halo, ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)

$R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1$-$C_4$)alkyl, and heteroaryl($C_1$-$C_4$)alkyl;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2H$, —$CO_2$($C_1$-$C_4$)alkyl, —$CONH_2$, —$CONH$($C_1$-$C_4$)alkyl, —$CON$(($C_1$-$C_4$)alkyl)(($C_1$-$C_4$)alkyl), —$SO_2$($C_1$-$C_4$)alkyl, —$SO_2NH_2$, —$SO_2NH$($C_1$-$C_4$)alkyl, and —$SO_2N$(($C_1$-$C_4$)alkyl)(($C_1$-$C_4$)alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

(1)

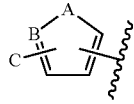

wherein in (1),
A is O, NH, or S; B is CH or N, and C is hydrogen or $C_1$-$C_8$ alkyl; or (2)

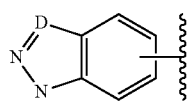

wherein in (2),
D is N or C optionally substituted by hydrogen or $C_1$-$C_8$ alkyl; or (3)

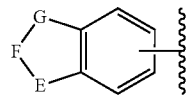

wherein in (3),
E is NH or $CH_2$; F is O or CO; and G is NH or $CH_2$; or (4)

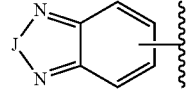

wherein in (4),
J is O, S or CO; or (5)

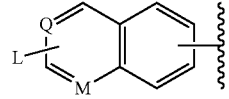

wherein in (5),
Q is CH or N;
M is CH or N; and
L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or (6)

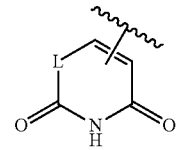

wherein in 6,
L/(6) is NH or $CH_2$; or (7)

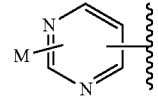

wherein in 7,
M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above; or

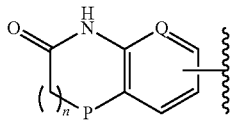

(8)

wherein in (8),

P is CH$_2$, NH, O, or S; Q/(8) is CH or N; and n is 0-2; or

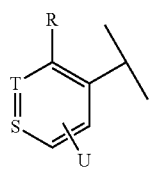

(9)

wherein in (9),

S/(9) and T(9) is C, or S/(9) is C and T(9) is N, or S/(9) is N and T/(9) is C;

R is hydrogen, amino, methyl, trifluoromethyl, halo;

U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazol-4-yl), wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above.

Subgroup B

X and Z are selected independently from the group consisting of (C$_1$-C$_8$)alkyl, (C$_3$-C$_8$)cycloalkyl, heterocycloalkyl, aryl, heteroaryl, —NR$^a$R$^b$, and —OR$^a$;

Y is H;

R$^1$ is (C$_1$-C$_8$)alkyl, (C$_3$-C$_8$)cycloalkyl, or heterocycloalkyl;

R$^3$ is hydrogen, (C$_1$-C$_8$)alkyl or halo;

R$^6$ is hydrogen, halo, cyano, trifluoromethyl, amino, (C$_1$-C$_8$)alkyl, (C$_3$-C$_8$)cycloalkyl, aryl, heteroaryl, acylamino; (C$_2$-C$_8$)alkynyl, arylalkynyl, heteroarylalkynyl; —SO$_2$R$^a$; —SO$_2$NR$^a$R$^b$, or —NR$^a$SO$_2$R$^b$;

wherein any (C$_1$-C$_8$)alkyl, (C$_3$-C$_8$)cycloalkyl, (C$_2$-C$_8$)alkynyl, arylalkynyl, heteroarylalkynyl group is optionally substituted by 1, 2 or 3 groups independently selected from halo, (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$,—NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, and heteroaryl(C$_1$-C$_4$)alkyl;

R$^a$ and R$^b$ are each independently hydrogen, (C$_1$-C$_8$)alkyl, (C$_2$-C$_8$)alkenyl, (C$_2$-C$_8$)alkynyl, (C$_3$-C$_8$)cycloalkyl, (C$_5$-C$_8$)cycloalkenyl, (C$_6$-C$_{10}$)bicycloalkyl, heterocycloalkyl, aryl, heteroaryl, wherein said (C$_1$-C$_8$)alkyl, (C$_2$-C$_8$)alkenyl, (C$_2$-C$_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C$_1$-C$_4$)alkoxy, amino, (C$_1$-C$_4$)alkylamino, ((C$_1$-C$_4$)alkyl)((C$_1$-C$_4$)alkyl)amino, —CO$_2$H, —CO$_2$(C$_1$-C$_4$)alkyl, —CONH$_2$, —CONH(C$_1$-C$_4$)alkyl, —CON((C$_1$-C$_4$)alkyl)((C$_1$-C$_4$)alkyl), —SO$_2$(C$_1$-C$_4$)alkyl, —SO$_2$NH$_2$, —SO$_2$NH(C$_1$-C$_4$)alkyl, and —SO$_2$N((C$_1$-C$_4$)alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$)alkyl, wherein said ring is optionally fused to a (C$_3$-C$_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine as or a compound of or another aryl or heteroaryl group as follows:

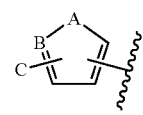

(1)

wherein in (1),

A is O, NH, or S; B is CH or N, and C is hydrogen or C$_1$-C$_8$ alkyl; or

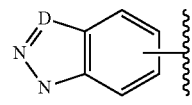

(2)

wherein in (2),

D is N or C optionally substituted by hydrogen or C$_1$-C$_8$ alkyl; or

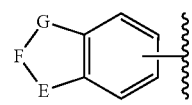

(3)

wherein in (3),
  E is NH or CH$_2$; F is O or CO; and G is NH or CH$_2$; or

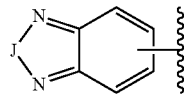
(4)

wherein in (4),
  J is O, S or CO; or

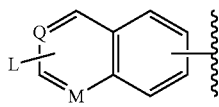
(5)

wherein in (5),
  Q is CH or N;
  M is CH or N; and
  L/(5) is hydrogen, halo, amino, cyano, (C$_1$-C$_8$)alkyl, (C$_3$-C$_8$)cycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
    wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$,
  wherein R$^a$ and R$^b$ are defined as above; or

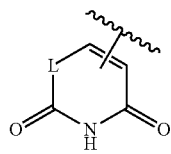
(6)

wherein in 6,
  L/(6) is NH or CH$_2$; or

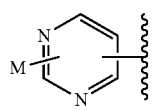
(7)

wherein in 7,
  M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
    wherein any (C$_1$-C$_8$)alkyl, (C$_3$-C$_8$)cycloalkyl, heterocloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above; or

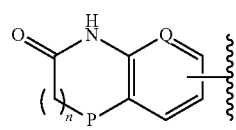
(8)

wherein in (8),
  P is CH$_2$, NH, O, or S; Q/(8) is CH or N; and n is 0-2; or

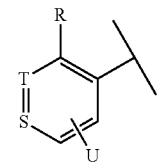
(9)

wherein in (9),
  S/(9) and T(9) is C, or S/(9) is C and T(9) is N, or S/(9) is N and T/(9) is C;
  R is hydrogen, amino, methyl, trifluoromethyl, halo;
  U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazol-4-yl),
    wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, wherein R$^a$ and R$^b$ are defined as above.

Subgroup C
  X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;
  Y is H;
  Z is methyl, ethyl, n-propyl, isopropyl, trifluoromethyl, or benzyl;
  R$^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;
  R$^3$ is H, methyl, ethyl, propyl, isopropyl or Br; and
  R$^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

Individual compounds can be found in the Examples set out below.

5-Bromo-N-[(4,6-dimethyl-2-oxo-1,2-dihydro-3-pyridinyl)methyl]-1-methyl-3-(1-methylethyl)-1H-indole-7-carboxamide;

5-{4-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;

5-{3-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;

N-[(4,6-Dimethyl-2-oxo-1,2-dihydro-3-pyridinyl)methyl]-1-methyl-3-(1-methylethyl)-5-[6-(4-methyl-1-piperazinyl)-3-pyridinyl]-1H-indole-7-carboxamide;

5-Bromo-1-methyl-3-(1-methylethyl)-N-[(6-methyl-2-oxo-4-propyl-1,2-dihydro-3-pyridinyl)methyl]-1H-indole-7-carboxamide;

5-{3-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;

5-{4-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;

1-Methyl-3-(1-methylethyl)-N-[(6-methyl-2-oxo-4-propyl-1,2-dihydro-3-pyridinyl)methyl]-5-[6-(4-methyl-1-piperazinyl)-3-pyridinyl]-1H-indole-7-carboxamide;

N-[(4,6-Dimethyl-2-oxo-1,2-dihydro-3-pyridinyl)methyl]-1-methyl-3-(1-methylethyl)-5-(6-methyl-3-pyridinyl)-1H-indole-7-carboxamide;

N-[(4,6-Dimethyl-2-oxo-1,2-dihydro-3-pyridinyl)methyl]-1-methyl-3-(1-methylethyl)-5-[6-(1-piperazinyl)-3-pyridinyl]-1H-indole-7-carboxamide;

5-(2-Amino-5-pyrimidinyl)-N-[(4,6-dimethyl-2-oxo-1,2-dihydro-3-pyridinyl)methyl]-1-methyl-3-(1-methylethyl)-1H-indole-7-carboxamide;

5-(6-Amino-3-pyridinyl)-N-[(4,6-dimethyl-2-oxo-1,2-dihydro-3-pyridinyl)methyl]-1-methyl-3-(1-methylethyl)-1H-indole-7-carboxamide;

N-[(4,6-Dimethyl-2-oxo-1,2-dihydro-3-pyridinyl)methyl]-1-methyl-3-(1-methylethyl)-5-(2-methyl-5-pyrimidinyl)-1H-indole-7-carboxamide;

N-[(4,6-Dimethyl-2-oxo-1,2-dihydro-3-pyridinyl)methyl]-1-methyl-3-(1-methylethyl)-5-(4-piperidinyl)-1H-indole-7-carboxamide;

N-[(4,6-Dimethyl-2-oxo-1,2-dihydro-3-pyridinyl)methyl]-1-methyl-3-(1-methylethyl)-5-(1-methyl-4-piperidinyl)-1H-indole-7-carboxamide;

N-[(4,6-Dimethyl-2-oxo-1,2-dihydro-3-pyridinyl)methyl]-1-methyl-3-(1-methylethyl)-5-(4-morpholinyl)-1H-indole-7-carboxamide;

N-[(4-Ethyl-6-methyl-2-oxo-1,2-dihydro-3-pyridinyl)methyl]-1-methyl-3-(1-methylethyl)-5-(4-morpholinyl)-1H-indole-7-carboxamide;

5-Bromo-N-[(4,6-dimethyl-2-oxo-1,2-dihydro-3-pyridinyl)methyl]-3-(1-methylethyl)-1H-indole-7-carboxamide;

N-((4,6-Dimethyl-2-oxo-1,2-dihydropyridin-3-yl)methyl)-3-isopropyl-1-methyl-5-(methylsulfonyl)-1H-indole-7-carboxamide;

N-[(4,6-Dimethyl-2-oxo-1,2-dihydro-3-pyridinyl)methyl]-1-methyl-3-(1-methylethyl)-5-(methyloxy)-1H-indole-7-carboxamide;

N-((4-Benzyl-6-methyl-2-oxo-1,2-dihydropyridin-3-yl)methyl)-5-bromo-3-isopropyl-1-methyl-1H-indole-7-carboxamide;

5-Bromo-1-methyl-3-(1-methylethyl)-N-[(4-methyl-2-oxo-1,2-dihydro-3-pyridinyl)methyl]-1H-indole-7-carboxamide;

N-[(4,6-Dimethyl-2-oxo-1,2-dihydro-3-pyridinyl)methyl]-1-methyl-3-(1-methylethyl)-1H-indole-7-carboxamide;

5-Cyclopropyl-N-((4,6-dimethyl-2-oxo-1,2-dihydropyridin-3-yl)methyl)-3-isopropyl-1-methyl-1H-indole-7-carboxamide;

N-((4,6-Dimethyl-2-oxo-1,2-dihydropyridin-3-yl)methyl)-3-isopropyl-5-(2-methoxythiazol-5-yl)-1-methyl-1H-indole-7-carboxamide.

By the term "co-administering" and derivatives thereof as used herein is meant either simultaneous administration or any manner of separate sequential administration of one or more additional pharmaceutically active compounds, whether for treating cancer, the side effects of cancer or cancer therapy, or some other disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

All tautomeric forms of the compounds described herein, including mixtures thereof, are intended to be encompassed within the scope of the invention. Generally, the compounds exemplified herein have been assigned names based on the structure of the tautomer of formula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Treatments

The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deactylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin) is an example of an anti-erbB2 antibody inhibitor of growth factor function. One example of an anti-erbB 1 antibody inhibitor of growth factor function is cetuximab (Erbitux™ C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. lntem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-Fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Chemical Background

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

General Experimental Methods

The following abbreviations are used throughout the experimental and have the following meaning:
aq aqueous
BINAP 2,2'-bis(diphenylphosphino)-1,1'-binapthyl
ca. circa
$CDCl_3$-d chloroform-d
$CD_3OD$-$d_4$ methanol-$d_4$
$Cs_2CO_3$ cesium carbonate
$CHCl_3$ chloroform
ACN acetonitrile
$CH_3CN$ acetonitrile
Celite® registered trademark of Celite Corp. brand of diatomaceous earth
DBU 1,8-diazabicyclo[5.4.0]undeca-7-ene
DCE dichloroethane
DCM methylene chloride
DME 1,2 dimethoxyethane
DMF N,N-dimethyl formamide
DIEA diisopropyl ethylamine
DMSO-$d_6$ dimethylsulfoxide-$d_6$
EtOAc ethyl acetate
EDC 1-(3-dimethylaminopropyl)-3-ethylcarbodimmide hydrochloride
h hour(s)
$^1$H NMR proton nuclear magnetic resonance
HCl hydrochloric acid
HOAT 1-hydroxy-7-azabenzotriazole
HPLC high performance liquid chromatography
IPA 2-propanol
$K_2CO_3$ potassium carbonate
KOH potassium hydroxide
LC/MS liquid chromatography/mass spectroscopy
$MgSO_4$ magnesium sulfate
MeOH methanol
min minute(s)
MTBE methyl tert-butyl ether
MS mass spectrometry
NaOH sodium hydroxide
$Na_2SO_4$ sodium sulfate
$NH_4OH$ ammonium hydroxide
NMM 4-methylmorpholine
NMP N-methyl-2-pyrrolidone
Pd/C palladium (10% by wt) on carbon
$PdCl_2(dppf)$-$CH_2Cl_2$ 1,1'-bis(diphenylphosphino)ferrocene-palladium(II)dichloride dichloromethane complex
$Pd(Ph_3P)_4$ tetrakis(triphenylphosphine)palladium(0)
$SOCl_2$ thionyl chloride
SPhos 2-dicyclohexylphosphino-2',6'-dimethoxybiphenyl
TFA trifluoroacetic acid
THF tetrahydrofuran
TLC thin layer chromatography The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase. Unless otherwise noted, a mobile phase of 25 mL/min A (acetonitrile-0.1% TFA): B (water-0.1% TFA), 10-80% gradient A (10 min) was utilized, with UV detection at 214 nM.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um partical size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50×4.6 mm, 1.8 μm)

eluting with CH$_3$CN: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal.

Analytical HPLC: Products were analyzed by Agilent 1100 Analytical Chromatography system, with 4.5×75 mm Zorbax XDB-C18 column (3.5 um) at 2 mL/min with a 4 min gradient from 5% CH$_3$CN (0.1% formic acid) to 95% CH$_3$CN (0.1% formic acid) in H$_2$O (0.1% formic acid) and a 1 min hold.

The compounds of Formula (I) can be made according to Scheme 1 or by analogous methods. 4-Bromo-2-iodoaniline (1) is converted to hydrazine 2 via a tin(II)-mediated reduction of the corresponding nitroso intermediate. Reductive alkylation of 2 with an aldehyde gives compounds of Formula 3. Cyclization of the hydrazones to provide indoles of Formula 4 can be accomplished with either ZnCl$_2$ or acid. Conversion of the iodide to the cyano, followed by based-mediated hydrolysis furnishes carboxylic acids of Formula 6. Alykylation of the nitrogen with an alkylhalide in the presence of base (e.g. sodium hydride), followed by saponification of the resultant ester with aqueous base provides compounds of Formula 7, which are coupled to various aminomethylpyridones 8 utilizing standard peptide coupling reagents (e.g. EDC, HOAT, NMM) to furnish compounds of Formula 9. Palladium-mediated cross-coupling of various boronic acids (or boronates) with 9 provides compounds of Formula 10.

Scheme 1

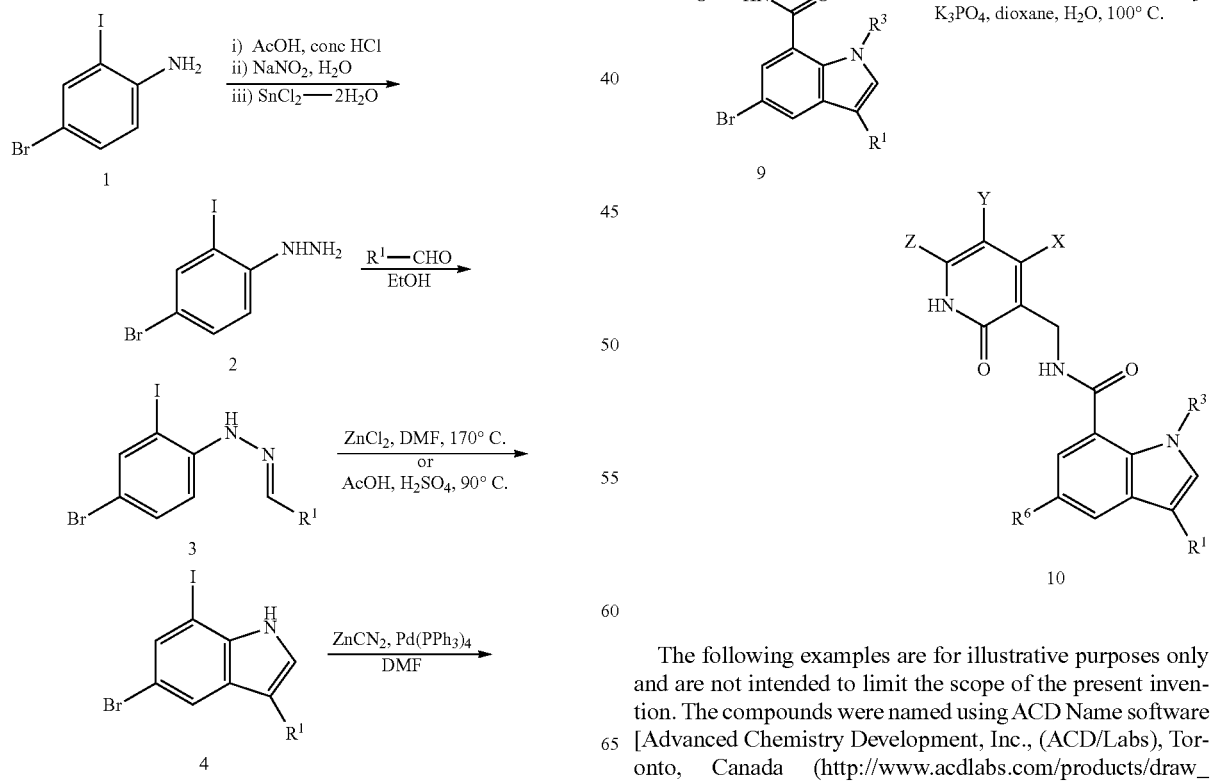

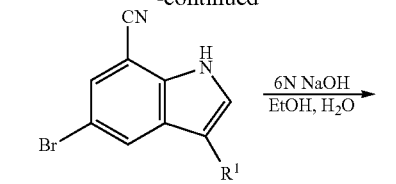

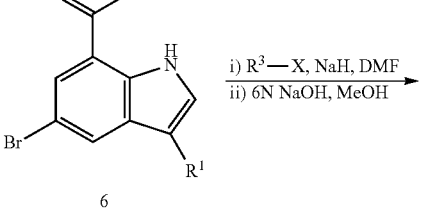

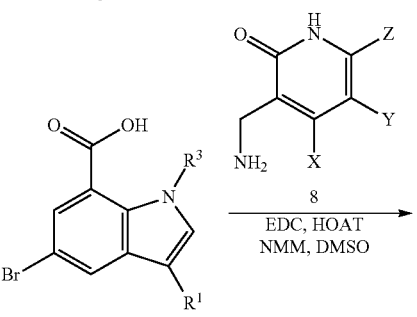

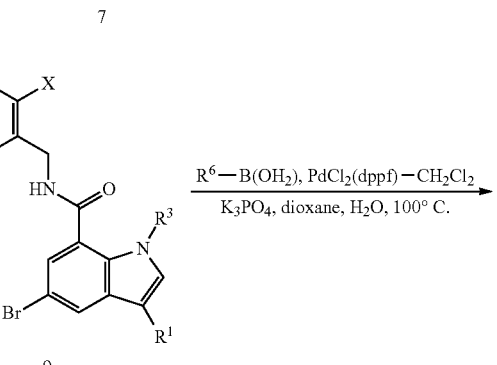

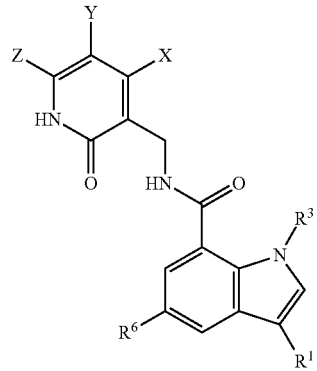

The following examples are for illustrative purposes only and are not intended to limit the scope of the present invention. The compounds were named using ACD Name software [Advanced Chemistry Development, Inc., (ACD/Labs), Toronto, Canada (http://www.acdlabs.com/products/draw_nom/)] or ChemBioDraw Ultra 12Struct=Name Pro 12 soft-

Example 1

5-Bromo-N-[(4,6-dimethyl-2-oxo-1,2-dihydro-3-pyridinyl)methyl]-1-methyl-3-(1-methylethyl)-1H-indole-7-carboxamide

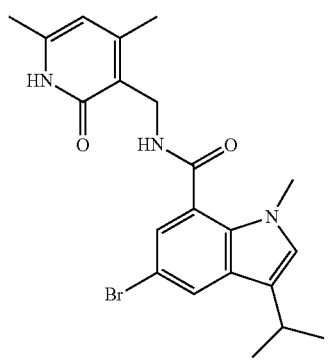 [SMILES: Cc1cc(C)c(CNC(=O)c2cc(Br)cc3c(C(C)C)cn(C)c23)c(=O)[nH]1]

a) 5-Bromo-7-iodo-3-(1-methylethyl)-1H-indole

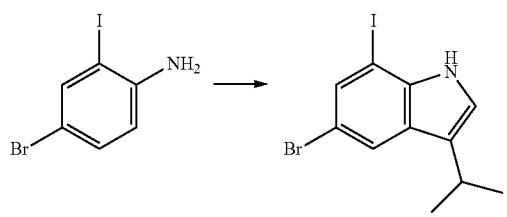

To a mechanically stirred solution of 4-bromo-2-iodoaniline (10.0 g, 33.6 mmol) in acetic acid (25 mL) was slowly added conc HCl (100 mL). The solution quickly became a thick suspension. The reaction was then cooled to 0° C. in an ice bath and treated slowly dropwise with a solution of sodium nitrite (2.6 g, 37.7 mmol) in water (20 mL). The reaction was stirred for 1 h, then a solution of tin(II) chloride dihydrate (16 g, 70.9 mmol) in conc. HCl (20 mL) was added slowly. The reaction was allowed to warm to RT and stirred for 2 h. LCMS indicated that the reaction was complete. The suspension was filtered, washed with water and dried under vacuum to give the crude hydrazine HCl salt (10.70 g, 30.6 mMol, 91%) as a beige solid (94% pure by LCMS).

The above hydrazine HCl salt (10.6 g, 30.3 mMol) was suspended in EtOH (100 mL), stirred, and treated with isovaleraldehyde (3.63 mL, 33.6 mmol). The reaction was stirred overnight at RT. (LCMS showed that the reaction was complete.) The now nearly clear solution was treated with sodium carbonate (3.5 g, 33.0 mmol), stirred for 30 minutes then evaporated to dryness under vacuum. The residue was suspended in 10% EtOAc in hexanes (~100 mL), passed through a pad of silica gel and washed with 10% EtOAc in hexanes (~100 mL). The filtrate was evaporated to dryness under vacuum to give the crude hydrazone (8.91 g, 23.3 mMol) as an orange oil (74% pure by LCMS). This crude hydrazone was used as is in the next reaction.

To a stirred solution of (1E/Z)-3-methylbutanal (4-bromo-2-iodophenyl)hydrazone (4.0 g, 10.50 mmol) in DMF (10 mL) was added zinc chloride (4.0 g, 29.3 mmol). The reaction was heated to 170° C. under a stream of N$_2$ and stirred until the reaction was complete by LCMS (~2 h). The reaction mixture was diluted with CH$_2$Cl$_2$, washed with 1 N Na$_2$CO$_3$, filtered to remove insoluble materials, washed with brine, dried (MgSO4), filtered and concentrated under vacuum. Purification by silica gel chromatography (Analogix SF25-80 g, 0 to 10% CH$_2$Cl$_2$ in hexanes) gave 5-bromo-7-iodo-3-(1-methylethyl)-1H-indole (2.23 g, 6.13 mmol, 58.4% yield) as a yellow oil. MS (ES)+ m/e 364.2 [M+H]$^+$ (very weak).

b) 5-Bromo-3-(1-methylethyl)-1H-indole-7-carbonitrile

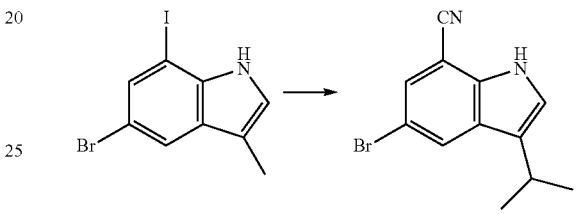

To a stirred solution of 5-bromo-7-iodo-3-(1-methylethyl)-1H-indole (3.05 g, 8.38 mmol) in DMF (50 mL) was added zinc cyanide (0.52 g, 4.43 mmol) and tetrakis(triphenylphosphine)palladium (0.8 g, 0.692 mmol). The reaction was purged with N$_2$, stirred and heated at 90° C. LCMS indicated that the reaction was complete. The reaction was evaporated to dryness under vacuum. Purification by silica gel chromatography (Analogix, SF25-60 g, 0 to 10% EtOAc in hexanes) and trituration with hexanes, filtering and drying under vacuum gave the product 5-bromo-3-(1-methylethyl)-1H-indole-7-carbonitrile (1.67 g, 6.35 mmol, 76% yield) as a light yellow solid. MS (ES)+ m/e 263.0 [M+H]$^+$.

c) 5-Bromo-3-(1-methylethyl)-1H-indole-7-carboxylic acid

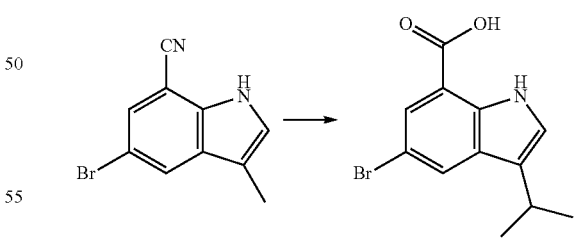

To a stirred solution of 5-bromo-3-(1-methylethyl)-1H-indole-7-carbonitrile (1.66 g, 6.31 mmol) in EtOH (45 mL) and water (15 mL) was added 6 N NaOH (10 mL, 60.0 mmol). The reaction was heated at reflux (100° C. oil bath) under N$_2$ for 72 h. LCMS showed that the reaction was complete after 24 h. The reaction was cooled to RT, evaporated to near dryness, diluted with water (~100 mL), and acidified with 6 N HCl (10 mL). The suspension was triturated, filtered, washed with water and dried under vacuum to give the product 5-bromo-3-(1-methylethyl)-1H-indole-7-carboxylic acid (2.29 g, 8.12 mmol, 129% yield) as an off-white solid. MS (ES)+ m/e 282.4 [M+H]+.

d) 5-Bromo-1-methyl-3-(1-methylethyl)-1H-indole-7-carboxylic acid

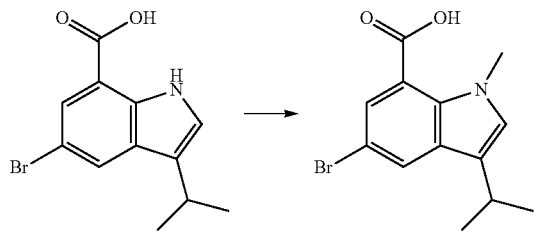 [SMILES: CC(C)c1c[nH]c2c(C(=O)O)cc(Br)cc12 ; CC(C)c1cn(C)c2c(C(=O)O)cc(Br)cc12]

To a stirred solution of 5-bromo-3-(1-methylethyl)-1H-indole-7-carboxylic acid (4.1 g, 14.53 mmol) in DMF (100 mL) at 0° C. was added iodomethane (3.6 mL, 57.6 mmol) followed by sodium hydride 60% dispersion in oil (1.4 g, 35.0 mmol) portionwise over 15 minutes. The reaction was allowed to warm to RT and stirred for 2 h. The reaction was recooled to 0° C., carefully quenched with water (5 mL), and evaporated to near dryness under vacuum. The residue was taken up in MeOH (50 mL) then treated with 6 N NaOH (10 mL, 60.0 mmol). The reaction was heated to 60° C. and stirred for 4 h. After cooling to RT the reaction was concentrated to near dryness, diluted with water, acidified with 6 N HCl (10 mL, 60 mmol), extracted with CH$_2$Cl$_2$, dried (Na$_2$SO$_4$), filtered, and evaporated to dryness to give the crude acid as a brown solid. Purification by silica gel chromatography (Analogix, SF40-120 g, 0 to 50% EtOAc in hexanes) gave material which was triturated with hexanes, filtered and dried under vacuum to give the product 5-bromo-1-methyl-3-(1-methylethyl)-1H-indole-7-carboxylic acid (2.98 g, 10.06 mmol, 69.2% yield) as a white solid. MS (ES)+ m/e 296.3 [M+H]+.

e) 5-Bromo-N-[(4,6-dimethyl-2-oxo-1,2-dihydro-3-pyridinyl)methyl]-1-methyl-3-(1-methylethyl)-1H-indole-7-carboxamide

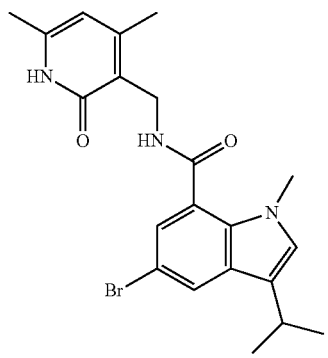 [SMILES: Cc1cc(C)c(CNC(=O)c2cc(Br)cc3c(C(C)C)cn(C)c23)c(=O)[nH]1]

To a stirred suspension of 5-bromo-1-methyl-3-(1-methylethyl)-1H-indole-7-carboxylic acid (300 mg, 1.013 mmol), 3-(aminomethyl)-4,6-dimethyl-2(1H)-pyridinone (280 mg, 1.484 mmol) and HOAt (200 mg, 1.469 mmol) in DMF (15 mL) was added N-methylmorpholine (170 µL, 1.546 mmol) and EDC free base (310 mg, 1.997 mmol). The reaction was stirred for 18 h at RT. LCMS showed that the reaction was complete. The reaction was evaporated to near dryness under vacuum. Water (~15 mL) was added and the solids which precipitated out were triturated, filtered and dried under vacuum. LCMS indicated that the solids were only 87% pure. The solid was partially dissolved in CH$_2$Cl$_2$. Noticed that the product began to crystallize out. Slowly added an equal volume of hexanes, triturated, filtered and dried under vacuum to give the product 5-bromo-N-[(4,6-dimethyl-2-oxo-1,2-dihydro-3-pyridinyl)methyl]-1-methyl-3-(1-methylethyl)-1H-indole-7-carboxamide (188 mg, 0.437 mmol, 43.1% yield) as a white solid. $^1$H NMR (400 MHz, DMSO-d$_6$) δ=11.50 (br. s., 1H), 8.54 (t, J=4.8 Hz, 1H), 7.75 (d, J=1.8 Hz, 1H), 7.14 (s, 1H), 7.09 (d, J=2.0 Hz, 1H), 5.87 (s, 1H), 4.31 (d, J=5.1 Hz, 2H), 3.65 (s, 3H), 3.11 (dt, J=6.9, 13.5 Hz, 1H), 2.22 (s, 3H), 2.12 (s, 3H), 1.26 (d, J=6.8 Hz, 6H). MS (ES)+ m/e 429.9 [M+H]+.

Example 2

5-{4-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide

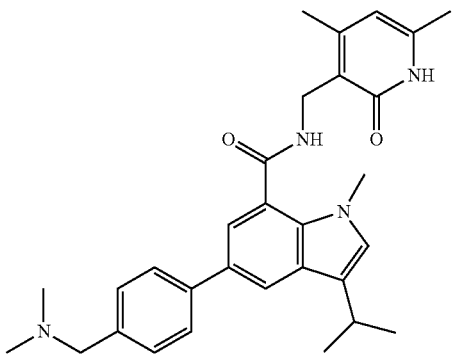

In a glass pressure tube was added 5-bromo-N-[(4,6-dimethyl-2-oxo-1,2-dihydro-3-pyridinyl)methyl]-1-methyl-3-(1-methylethyl)-1H-indole-7-carboxamide (225 mg, 0.523 mmol), 4-(N,N-dimethylaminomethyl)phenylboronic acid pinacol ester hydrochloride (200 mg, 0.672 mmol), potassium phosphate (340 mg, 1.602 mmol), dioxane (12 mL) and water (3 mL). The reaction was stirred and purged with N$_2$ then PdCl$_2$ (dppf)-CH$_2$Cl$_2$ adduct (40 mg, 0.049 mmol) was added. The reaction was capped and stirred at 110° C. for 4 h LCMS indicated that the reaction was complete. The dark black reaction was transferred to a round bottom flask and evaporated to dryness. The crude material was purified by silica gel chromatography (Analogix, SF25-40 g, 0 to 70% CH$_2$Cl$_2$/20% (5% NH$_4$OH in MeOH) in CH$_2$Cl$_2$). A short DASi column was used and the compound loaded as a suspension in CH$_2$Cl$_2$. The pure fractions were combined and evaporated to dryness to give the product as a very dark brown-black solid. The solid was taken up in CH$_2$Cl$_2$ and treated with Silicycle Si-Thiol derivatized silica gel (2 g, 1.46 mMol/g, cat. no. R51030B). After swirling for ~30 minutes the mixture was filtered through a pad of Celite, washed with CH$_2$Cl$_2$, and evaporated to dryness. The now light yellow colored solid was dissolved in a small amount of CH$_2$Cl$_2$, triturated with hexanes, filtered and dried under vacuum to give 5-{4-[(dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide (95 mg, 0.196 mmol, 37.5% yield) as a light tan solid. $^1$H NMR (400 MHz, DMSO-d6) δ 11.50 (s, 1H), 8.50 (t, J=4.93 Hz, 1H), 7.83 (d, J=1.52 Hz, 1H), 7.68 (s, 1H), 7.66 (s, 1H), 7.40 (s, 1H), 7.38 (s, 1H), 7.33 (d, J=1.52 Hz, 1H), 7.10 (s, 1H), 5.87 (s, 1H), 4.36 (d, J=5.05 Hz, 2H), 3.69 (s, 3H), 3.34 (br. s., 3H), 3.22 (dt, J=6.73, 13.58 Hz, 1H), 2.26 (br. s., 6H), 2.24 (s, 2H), 2.11 (s, 3H), 1.31 (d, J=6.82 Hz, 6H). MS (ES)+m/e 485.3 [M+H]⁺.

Following the general procedure of Examples 1 and 2, the following compounds were prepared:

Example 3

5-{3-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide

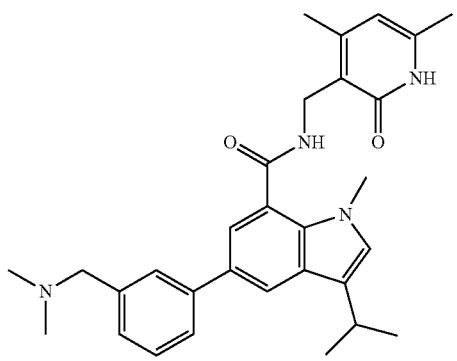

The title compound was prepared in the same manner as described for Example 2 using 3-(N,N-dimethylaminomethyl)phenylboronic acid pinacol ester hydrochloride (200 mg, 0.67 mmol). Obtained 110 mg of the title compound (43% yield). ¹H NMR (400 MHz, DMSO-d6) δ ppm 11.50 (s, 1H), 8.51 (t, J=4.80 Hz, 1H), 7.82 (d, J=1.77 Hz, 1H), 7.56-7.65 (m, 2H), 7.41 (t, J=7.58 Hz, 1H), 7.32 (d, J=1.77 Hz, 1H), 7.25 (d, J=7.58 Hz, 1H), 7.10 (s, 1H), 5.87 (s, 1H), 4.36 (d, J=5.05 Hz, 2H), 3.69 (s, 3H), 3.34 (s, 3H), 3.22 (ddd, J=6.82, 6.95, 13.52 Hz, 1H), 2.25 (br. s., 6H), 2.24 (s, 2H), 2.11 (s, 3H), 1.31 (d, J=6.82 Hz, 6H). MS (ES) [M+H]⁺ 485.3.

Example 4

N-[(4,6-Dimethyl-2-oxo-1,2-dihydro-3-pyridinyl)methyl]-1-methyl-3-(1-methylethyl)-5-[6-(4-methyl-1-piperazinyl)-3-pyridinyl]-1H-indole-7-carboxamide

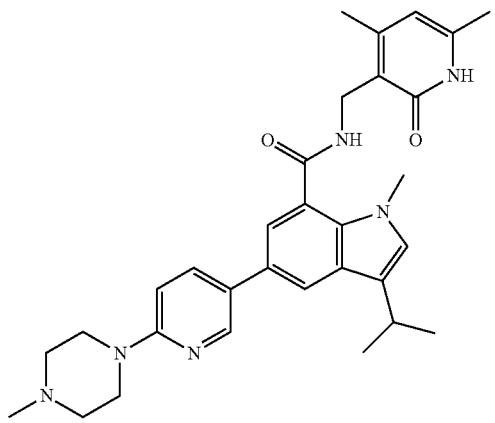

The title compound was prepared in the same manner as described for Example 2 using [6-(4-methyl-1-piperazinyl)-3-pyridinyl]boronic acid (160 mg, 0.72 mmol). Obtained 92 mg of the title compound (33% yield). ¹H NMR (400 MHz, DMSO-d6) δ ppm 11.50 (s, 1H), 8.42-8.49 (m, 2H), 7.89 (dd, J=2.40, 8.72 Hz, 1H), 7.76 (d, J=1.52 Hz, 1H), 7.26 (d, J=1.77 Hz, 1H), 7.08 (s, 1H), 6.93 (d, J=8.84 Hz, 1H), 5.87 (s, 1H), 4.36 (d, J=5.05 Hz, 2H), 3.67 (s, 3H), 3.56 (br. s., 4H), 3.20 (dt, J=6.79, 13.45 Hz, 1H), 2.59 (br. s., 4H), 2.33 (br. s., 3H), 2.24 (s, 3H), 2.12 (s, 3H), 1.30 (d, J=6.82 Hz, 6H). MS (ES) [M+H]⁺ 527.2.

Example 5

5-Bromo-1-methyl-3-(1-methylethyl)-N-[(6-methyl-2-oxo-4-propyl-1,2-dihydro-3-pyridinyl)methyl]-1H-indole-7-carboxamide

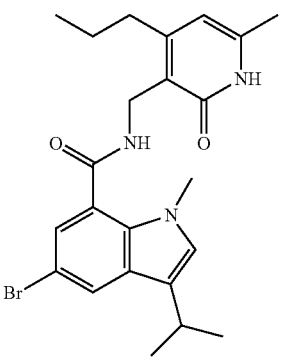 [SMILES: CCCc1cc(C)[nH]c(=O)c1CNC(=O)c1cc(Br)cc2c(C(C)C)cn(C)c12]

The title compound was prepared in the same manner as described for Example 1 using 3-(aminomethyl)-6-methyl-4-propyl-2(1H)-pyridinone (Intermediate 5; 620 mg, 3.44 mmol). Obtained 1.2 g of the title compound (98% yield). ¹H NMR (400 MHz, DMSO-d6) δ ppm 11.51 (s, 1H), 8.52 (t, J=4.93 Hz, 1H), 7.75 (d, J=1.77 Hz, 1H), 7.14 (s, 1H), 7.09 (d, J=2.02 Hz, 1H), 5.90 (s, 1H), 4.33 (d, J=5.05 Hz, 2H), 3.66 (s, 3H), 3.11 (quin, J=6.82 Hz, 1H), 2.52-2.56 (m, 2H), 2.13 (s, 3H), 1.55 (sxt, J=7.53 Hz, 2H), 1.26 (d, J=6.82 Hz, 6H), 0.94 (t, J=7.33 Hz, 3H). MS (ES) [M+H]⁺ 458.1.

Example 6

5-{3-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide

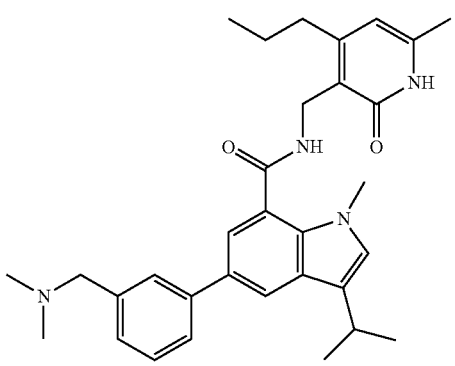

The title compound was prepared in the same manner as described for Example 2 using 5-bromo-1-methyl-3-(1-methylethyl)-N-[(6-methyl-2-oxo-4-propyl-1,2-dihydro-3-pyridinyl)methyl]-1H-indole-7-carboxamide (300 mg, 0.65 mmol) and 3-(N,N-dimethylaminomethyl)phenylboronic acid pinacol ester hydrochloride (250 mg, 0.84 mmol). Obtained 210 mg of the title compound (63% yield). $^1$H NMR (400 MHz, DMSO-d6) δ ppm 11.50 (s, 1H), 8.49 (t, J=4.80 Hz, 1H), 7.82 (d, J=1.77 Hz, 1H), 7.56-7.64 (m, 2H), 7.41 (t, J=7.58 Hz, 1H), 7.31 (d, J=1.52 Hz, 1H), 7.25 (d, J=7.58 Hz, 1H), 7.11 (s, 1H), 5.91 (s, 1H), 4.38 (d, J=5.05 Hz, 2H), 3.70 (s, 3H), 3.33 (s, 2H), 3.22 (quin, J=6.76 Hz, 1H), 2.52-2.59 (m, J=6.82, 8.59 Hz, 2H), 2.26 (br. s., 6H), 2.13 (s, 3H), 1.58 (sxt, J=7.53 Hz, 2H), 1.31 (d, J=6.82 Hz, 6H), 0.94 (t, J=7.33 Hz, 3H). MS (ES) [M+H]$^+$ 513.3.

Example 7

5-{4-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide

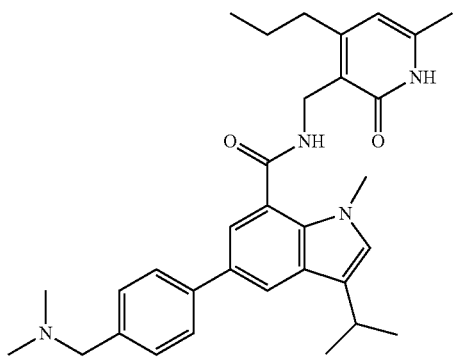

The title compound was prepared in the same manner as described for Example 2 using 5-bromo-1-methyl-3-(1-methylethyl)-N-[(6-methyl-2-oxo-4-propyl-1,2-dihydro-3-pyridinyl)methyl]-1H-indole-7-carboxamide (300 mg, 0.65 mmol) and 4-(N,N-dimethylaminomethyl)phenylboronic acid pinacol ester hydrochloride (250 mg, 0.84 mmol). Obtained 159 mg of the title compound (47% yield). $^1$H NMR (400 MHz, DMSO-d6) δ ppm 11.51 (s, 1H), 8.48 (t, J=4.80 Hz, 1H), 7.83 (d, J=1.77 Hz, 1H), 7.67 (s, 1H), 7.65 (s, 1H), 7.39 (s, 1H), 7.37 (s, 1H), 7.33 (d, J=1.52 Hz, 1H), 7.10 (s, 1H), 5.90 (s, 1H), 4.38 (d, J=4.80 Hz, 2H), 3.70 (s, 3H), 3.34 (br. s., 2H), 3.22 (dt, J=6.82, 13.64 Hz, 1H), 2.52-2.59 (m, 2H), 2.25 (s, 6H), 2.13 (s, 3H), 1.52-1.63 (m, 2H), 1.31 (d, J=6.82 Hz, 6H), 0.94 (t, J=7.33 Hz, 3H). MS (ES) [M+H]$^+$ 513.3.

Example 8

1-Methyl-3-(1-methylethyl)-N-[(6-methyl-2-oxo-4-propyl-1,2-dihydro-3-pyridinyl)methyl]-5-[6-(4-methyl-1-piperazinyl)-3-pyridinyl]-1H-indole-7-carboxamide

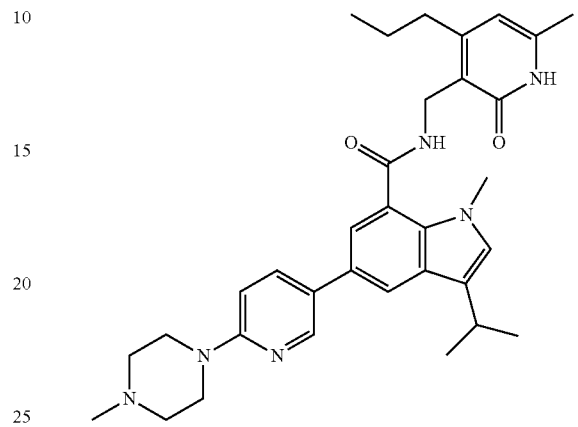

The title compound was prepared in the same manner as described for Example 2 using 5-bromo-1-methyl-3-(1-methylethyl)-N-[(6-methyl-2-oxo-4-propyl-1,2-dihydro-3-pyridinyl)methyl]-1H-indole-7-carboxamide (480 mg, 1.05 mmol) and [6-(4-methyl-1-piperazinyl)-3-pyridinyl]boronic acid (320 mg, 1.45 mmol). Obtained 345 mg of the title compound (59% yield). $^1$H NMR (400 MHz, DMSO-d6) δ ppm 11.51 (s, 1H), 8.41-8.48 (m, J=2.53 Hz, 2H), 7.86 (dd, J=2.53, 8.84 Hz, 1H), 7.76 (d, J=1.77 Hz, 1H), 7.26 (d, J=1.52 Hz, 1H), 7.08 (s, 1H), 6.92 (d, J=8.84 Hz, 1H), 5.90 (s, 1H), 4.37 (d, J=4.80 Hz, 2H), 3.68 (s, 3H), 3.48-3.56 (m, 4H), 3.20 (quin, J=6.76 Hz, 1H), 2.52-2.58 (m, 2H), 2.44 (br. s., 4H), 2.25 (s, 3H), 2.13 (s, 3H), 1.57 (qt, J=7.36, 7.56 Hz, 2H), 1.30 (d, J=6.82 Hz, 6H), 0.93 (t, J=7.33 Hz, 3H). MS (ES) [M+H]$^+$ 555.1.

Example 9

N-[(4,6-Dimethyl-2-oxo-1,2-dihydro-3-pyridinyl)methyl]-1-methyl-3-(1-methylethyl)-5-(6-methyl-3-pyridinyl)-1H-indole-7-carboxamide

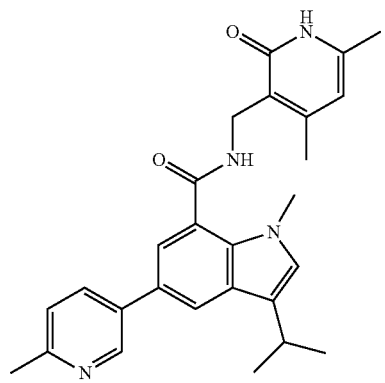

a) 1-Methyl-3-(1-methylethyl)-5-(6-methyl-3-pyridinyl)-1H-indole-7-carboxylic acid

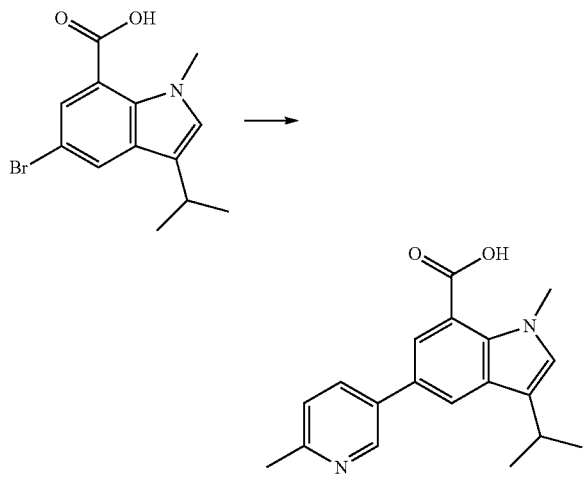

To a 40 mL vial was added 5-bromo-1-methyl-3-(1-methylethyl)-1H-indole-7-carboxylic acid (0.850 g, 2.87 mmol), (6-methyl-3-pyridinyl)boronic acid (0.432 g, 3.16 mmol), K$_2$CO$_3$ (1.190 g, 8.61 mmol) and PdCl$_2$(dppf)-CH$_2$Cl$_2$ adduct (0.234 g, 0.287 mmol). The reagents were diluted with 1,2-dimethoxyethane (21.5 mL) and water (7.2 mL). The reaction was heated to 100° C. with stirring for 30 minutes, then filtered and concentrated under vacuum to give a thick brown residue. The residue was diluted with saturated NaHCO$_3$ (15 mL) and water (10 mL) and aqueous solution washed with EtOAc (3×40 mL). The aqueous solution was then slowly added to a rapidly stirred, cooled (0° C.) solution of 1 N HCl. The mixture was stirred for 20 min and the solids collected by vacuum filtration. LCMS showed the solids contained only a small amount of desired product. The solids were discarded. The acidic aqueous solution was extracted with EtOAc (3×250 mL). LCMS showed the desired product in both layers. Thus, both the organic and aqueous layers were concentrated. The residue was purified by reverse phase HPLC (Gemini 50×100 mm column, acetonitrile and 0.1% formic acid/water) to give 1-methyl-3-(1-methylethyl)-5-(6-methyl-3-pyridinyl)-1H-indole-7-carboxylic acid (590 mg, 66.6% yield) as light tan solid. MS (ES) [M+H]$^+$ 309.5.

b) N-[(4,6-Dimethyl-2-oxo-1,2-dihydro-3-pyridinyl)methyl]-1-methyl-3-(1-methylethyl)-5-(6-methyl-3-pyridinyl)-1H-indole-7-carboxamide

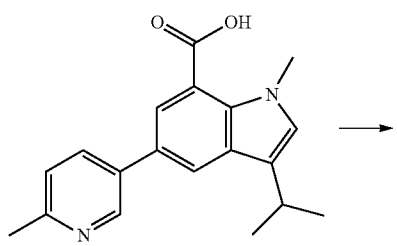

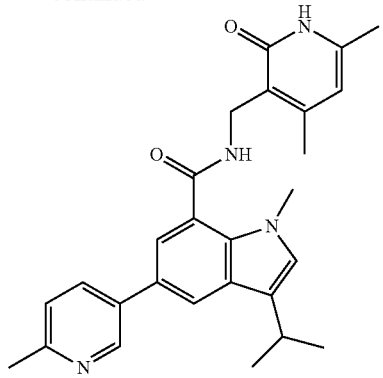

To a 20 mL vial was added 1-methyl-3-(1-methylethyl)-5-(6-methyl-3-pyridinyl)-1H-indole-7-carboxylic acid (0.10 g, 0.324 mmol), 3-(aminomethyl)-4,6-dimethyl-2(1H)-pyridinone (0.098 g, 0.519 mmol), 1-hydroxy-7-azabenzotriazole (0.088 g, 0.649 mmol) and EDC (0.124 g, 0.649 mmol). The reagents were diluted with DMSO (3 mL) and N-methylmorpholine (0.178 mL, 1.621 mmol). The mixture was stirred overnight, then slowly poured into ice-water (50 mL). The mixture was stirred for 10 min, then allowed to sit for 10 min. The mixture was then extracted with EtOAc (2×) and the combined organics washed with brine, dried over magnesium sulfate, and concentrated in vacuo. The residue was triturated with MTBE and the resulting solid dried in a vac oven at 45° C. for 4 h. Purified the solid by HPLC (Gilson; Sunfire 30×75 mm column; Gradient B: 10-65%; A: water+0.1% TFA; B: CH3CN+0.1% TFA). The residue was dissolved in 10% MeOH/DCM and treated with Silicycle carbonate resin (0.65 g) at 37° C. for 15 min. The mixture was allowed to cool to RT and was filtered through Celite. Concentrated in vacuo to give N-[(4,6-dimethyl-2-oxo-1,2-dihydro-3-pyridinyl)methyl]-1-methyl-3-(1-methylethyl)-5-(6-methyl-3-pyridinyl)-1H-indole-7-carboxamide (55 mg, 37.6% yield). $^1$H NMR (400 MHz, DMSO-d6) δ ppm 1.30 (d, J=6.82 Hz, 6H) 2.11 (s, 3H) 2.24 (s, 3H) 3.16-3.28 (m, 1H) 3.33 (s, 3H) 3.68 (s, 3H) 4.36 (d, J=5.05 Hz, 2H) 5.87 (s, 1H) 7.11 (s, 1H) 7.28-7.37 (m, 2H) 7.86 (d, J=1.77 Hz, 1H) 7.98 (dd, J=8.08, 2.53 Hz, 1H) 8.50 (t, J=4.93 Hz, 1H) 8.77 (d, J=2.27 Hz, 1H) 11.50 (s, 1H). MS (ES) [M+H]$^+$ 443.2.

Example 10

N-[(4,6-Dimethyl-2-oxo-1,2-dihydro-3-pyridinyl)methyl]-1-methyl-3-(1-methylethyl)-5-[6-(1-piperazinyl)-3-pyridinyl]-1H-indole-7-carboxamide

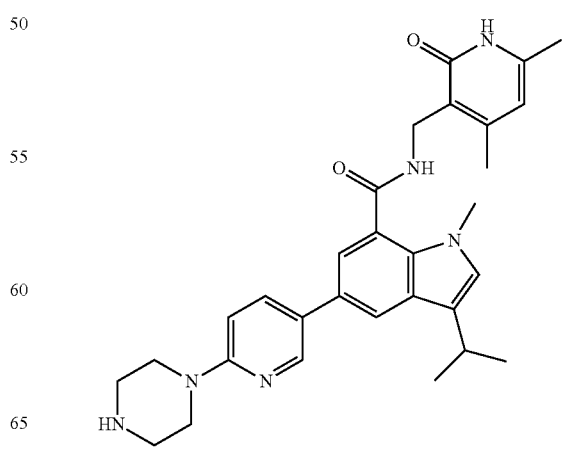

The title compound was prepared in the same manner as described for Example 2 using 1-[5-(4,4,5,5-tetramethyl-1,3,2-dioxaborolan-2-yl)-2-pyridinyl]piperazine (81 mg, 0.28 mmol). Obtained 92 mg of the title compound (76% yield). $^1$H NMR (400 MHz, DMSO-d6) δ ppm 1.30 (d, J=6.82 Hz, 6H) 2.11 (s, 3H) 2.23 (s, 3H) 2.73-2.85 (m, 4H) 3.19 (dt, J=13.64, 6.82 Hz, 1H) 3.39-3.46 (m, 4H) 3.67 (s, 3H) 4.35 (d, J=5.05 Hz, 2H) 5.87 (s, 1H) 6.87 (d, J=8.84 Hz, 1H) 7.07 (s, 1H) 7.25 (d, J=1.77 Hz, 1H) 7.75 (d, J=1.52 Hz, 1H) 7.85 (dd, J=8.84, 2.78 Hz, 1H) 8.39-8.52 (m, 2H) 11.49 (br. s., 1H). MS (ES) [M+H]$^+$ 513.3.

Example 11

5-(2-Amino-5-pyrimidinyl)-N-[(4,6-dimethyl-2-oxo-1,2-dihydro-3-pyridinyl)methyl]-1-methyl-3-(1-methylethyl)-1H-indole-7-carboxamide

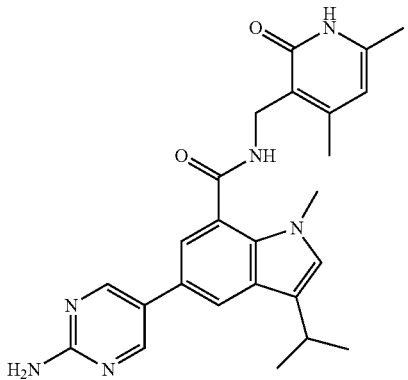 [SMILES: Cc1cc(C)c(CNC(=O)c2cc(-c3cnc(N)nc3)cc3c(C(C)C)cn(C)c23)c(=O)[nH]1]

The title compound was prepared in the same manner as described for Example 2 using 5-(4,4,5,5-tetramethyl-1,3,2-dioxaborolan-2-yl)-2-pyrimidinamine (62 mg, 0.28 mmol). Obtained 74 mg of the title compound (70% yield). $^1$H NMR (400 MHz, DMSO-d6) δ ppm 1.29 (d, J=6.82 Hz, 6H) 2.11 (s, 3H) 2.24 (s, 3H) 3.13-3.25 (m, 1H) 3.67 (s, 3H) 4.35 (d, J=5.05 Hz, 2H) 5.87 (s, 1H) 6.66 (s, 2H) 7.08 (s, 1H) 7.25 (d, J=1.77 Hz, 1H) 7.77 (d, J=1.77 Hz, 1H) 8.44 (t, J=4.93 Hz, 1H) 8.57 (s, 2H) 11.50 (s, 1H). MS (ES) [M+H]$^+$ 445.2.

Example 12

5-(6-Amino-3-pyridinyl)-N-[(4,6-dimethyl-2-oxo-1,2-dihydro-3-pyridinyl)methyl]-1-methyl-3-(1-methylethyl)-1H-indole-7-carboxamide

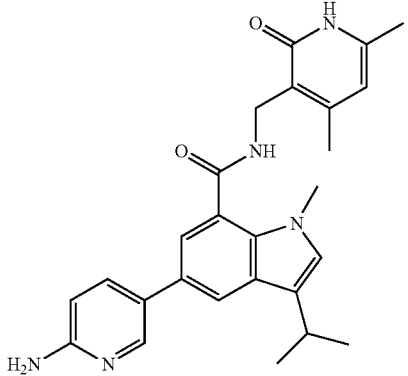 [SMILES: Cc1cc(C)c(CNC(=O)c2cc(-c3ccc(N)nc3)cc3c(C(C)C)cn(C)c23)c(=O)[nH]1]

The title compound was prepared in the same manner as described for Example 2 using 5-(4,4,5,5-tetramethyl-1,3,2-dioxaborolan-2-yl)-2-pyridinamine (61 mg, 0.28 mmol). Obtained 50 mg of the title compound (48% yield). $^1$H NMR (400 MHz, DMSO-d6) δ ppm 1.29 (d, J=6.82 Hz, 6H) 2.11 (s, 3H) 2.23 (s, 3H) 3.19 (dt, J=13.58, 6.73 Hz, 1H) 3.66 (s, 3H) 4.35 (d, J=5.05 Hz, 2H) 5.82-5.99 (m, 3H) 6.52 (d, J=8.34 Hz, 1H) 7.05 (s, 1H) 7.21 (d, J=1.77 Hz, 1H) 7.64-7.76 (m, 2H) 8.23 (d, J=2.02 Hz, 1H) 8.45 (t, J=4.93 Hz, 1H) 11.40 (br. s., 1H). MS (ES) [M+H]$^+$ 444.2.

Example 13

N-[(4,6-Dimethyl-2-oxo-1,2-dihydro-3-pyridinyl)methyl]-1-methyl-3-(1-methylethyl)-5-(2-methyl-5-pyrimidinyl)-1H-indole-7-carboxamide

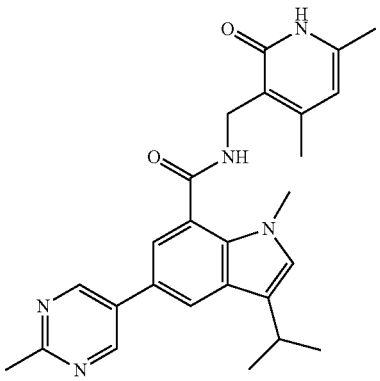

The title compound was prepared in the same manner as described for Example 2 using 2-methyl-5-(4,4,5,5-tetramethyl-1,3,2-dioxaborolan-2-yl)pyrimidine (61 mg, 0.28 mmol). Obtained 36 mg of the title compound (34% yield). $^1$H NMR (400 MHz, DMSO-d6) δ ppm 1.30 (d, J=6.82 Hz, 6H) 2.11 (s, 3H) 2.24 (s, 3H) 2.66 (s, 3H) 3.17-3.28 (m, 1H) 3.69 (s, 3H) 4.36 (d, J=5.05 Hz, 2H) 5.87 (s, 1H) 7.14 (s, 1H) 7.40 (d, J=1.52 Hz, 1H) 7.97 (d, J=1.77 Hz, 1H) 8.50 (t, J=4.93 Hz, 1H) 9.04 (s, 2H) 11.50 (s, 1H). MS (ES) [M+H]$^+$ 444.2.

Example 14

N-[(4,6-Dimethyl-2-oxo-1,2-dihydro-3-pyridinyl)methyl]-1-methyl-3-(1-methylethyl)-5-(4-piperidinyl)-1H-indole-7-carboxamide

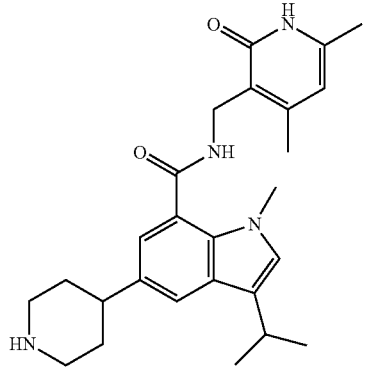 [SMILES: Cc1cc(C)c(CNC(=O)c2cc(C3CCNCC3)cc3c(C(C)C)cn(C)c23)c(=O)[nH]1]

a) 1,1-Dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-3,6-dihydro-1(2H)-pyridinecarboxylate

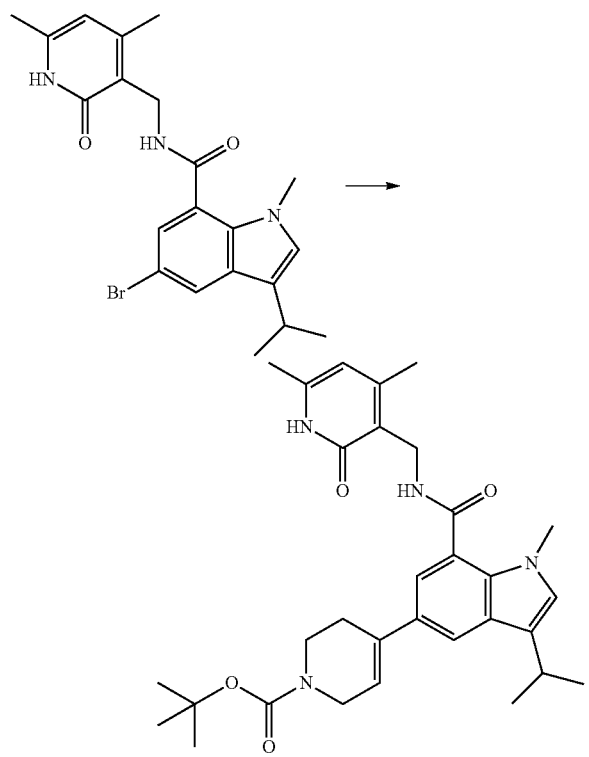

In an oven dried 20 mL vial, equipped with septum cap and stir bar, that was cooled to RT under a nitrogen stream, was added 5-bromo-N-[(4,6-dimethyl-2-oxo-1,2-dihydro-3-pyridinyl)methyl]-1-methyl-3-(1-methylethyl)-1H-indole-7-carboxamide (0.25 g, 0.581 mmol), 1,1-dimethylethyl 4-(4,4,5,5-tetramethyl-1,3,2-dioxaborolan-2-yl)-3,6-dihydro-1(2H)-pyridinecarboxylate (0.180 g, 0.581 mmol), then potassium phosphate(tribasic) (0.370 g, 1.743 mmol) as solids. 1,4-Dioxane (4 mL) and water (1 mL) were added and the vial purged with nitrogen for 10 min. Then $PdCl_2$(dppf)-$CH_2Cl_2$ adduct (0.071 g, 0.087 mmol) was added and the vial purged 1 min, sealed and placed into a heat block at 100° C. It was stirred for 2 h. and allowed to sit overnight at RT. The reaction mixture was diluted with EtOAc, silica gel added, and the mixture concentrated in vacuo to a flowable solid.

Purification: A 24 gram Isco silica column was used. Gradient B: 3-85%. A: Dichloromethane. B: 10% (2 M ammonia in methanol) in chloroform. Appropriate fractions were combined and volatiles removed in vacuo to a give 1,1-dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-3,6-dihydro-1(2H)-pyridinecarboxylate as a yellow foam (0.27 g, 0.406 mmol, 69.8% yield). MS (ES) [M+H]⁺ 533.1.

b) 1,1-Dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-1-piperidinecarboxylate

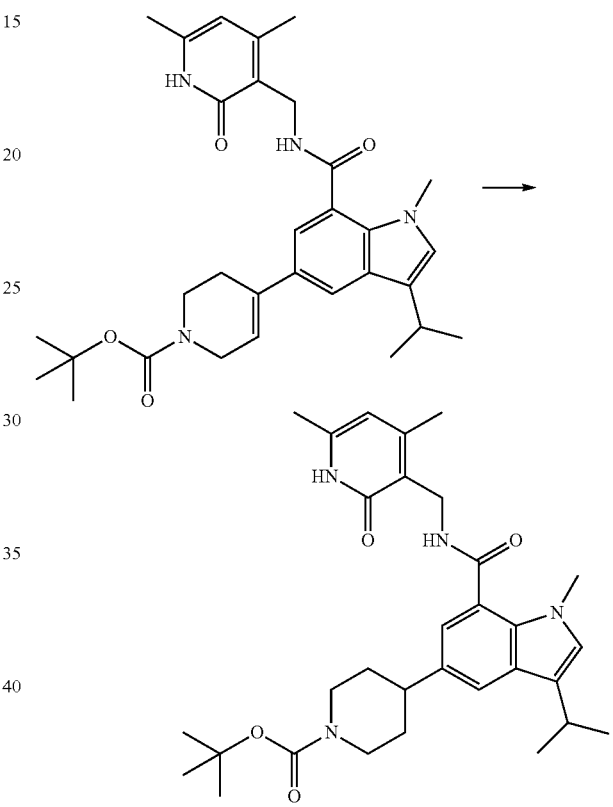

1,1-Dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-3,6-dihydro-1(2H)-pyridinecarboxylate (0.27 g, 0.507 mmol) was dissolved in ethanol (10 mL) and placed in a funnel under a $N_2$ stream for 10 min. Palladium on carbon (0.081 g, 0.076 mmol) was added and the reaction placed alternatingly under $N_2$ and $H_2$ via a 3-way valve. Switched atmosphere to hydrogen (balloon) and stirred at RT overnight. Placed reaction back under $N_2$, diluted with DCM, and added Celite. The mixture was stirred for 5 min, then filtered through analytical grade Celite and washed with 10% MeOH. Solvent was removed in vacuo giving a residue that was dried on hi-vacuum for 1 h to give 1,1-dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-1-piperidinecarboxylate (0.28 g, 0.524 mmol, 103% yield). MS (ES) [M+H]⁺ 535.0.

c) N-[(4,6-Dimethyl-2-oxo-1,2-dihydro-3-pyridinyl)methyl]-1-methyl-3-(1-methylethyl)-5-(4-piperidinyl)-1H-indole-7-carboxamide

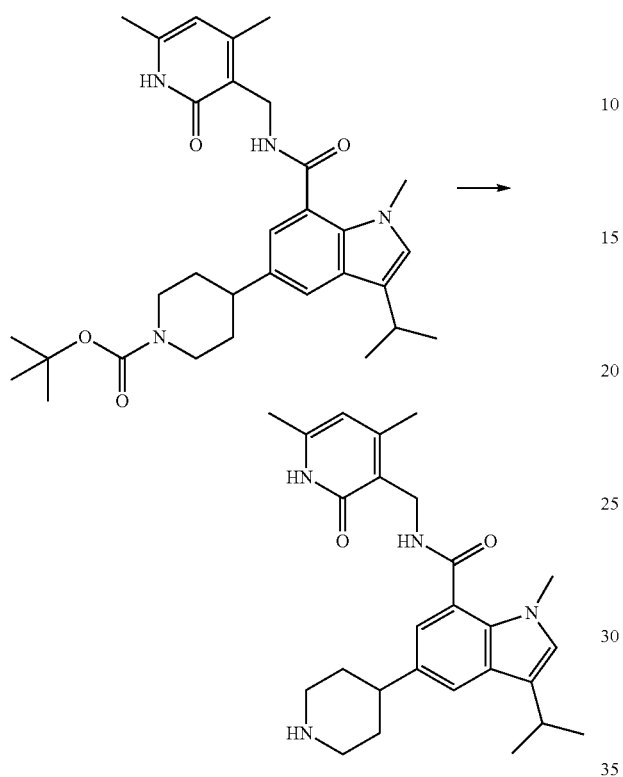

To a solution of 1,1-dimethylethyl 4-[7-({[(4,6-dimethyl-2-oxo-1,2-dihydro-3-pyridinyl)methyl]amino}carbonyl)-1-methyl-3-(1-methylethyl)-1H-indol-5-yl]-1-piperidinecarboxylate (0.28 g, 0.524 mmol) in dichloromethane (4 mL) was added TFA (1.009 mL, 13.09 mmol) via syringe and the mixture stirred for 1 h. The volatiles were removed in vacuo to give a residue, which was dissolved in 10% MeOH/DCM and treated with Silicylce Carbonate resin (1.0 gram) to give a mixture. It was stirred for 15 min at 37° C., then allowed to stand for 15 min. The mixture was filtered, washed with 10% MeOH/DCM, and the filtrate concentrated in vacuo.

Purification: 12 gram Isco GOLD silica column. Gradient B: 10-100%. A: Dichloromethane. B: 10% (2 M ammonia in methanol) in chloroform. Combined product fractions and removed volatiles in vacuo to give N-[(4,6-dimethyl-2-oxo-1,2-dihydro-3-pyridinyl)methyl]-1-methyl-3-(1-methylethyl)-5-(4-piperidinyl)-1H-indole-7-carboxamide (0.18 g, 0.406 mmol, 78% yield). $^1$H NMR (400 MHz, DMSO-d6) δ ppm 1.27 (d, J=6.82 Hz, 6H) 1.63-1.88 (m, 4H) 2.11 (s, 3H) 2.22 (s, 3H) 2.70-2.92 (m, 3H) 3.08-3.17 (m, 1H) 3.23 (d, J=12.13 Hz, 2H) 3.62 (s, 3H) 4.33 (d, J=5.05 Hz, 2H) 5.87 (s, 1H) 6.90 (d, J=1.52 Hz, 1H) 7.02 (s, 1H) 7.39 (d, J=1.52 Hz, 1H) 8.28-8.42 (m, 1H), 11.50 (s, 1H). MS (ES) [M+H]$^+$ 435.1.

Example 15

N-[(4,6-Dimethyl-2-oxo-1,2-dihydro-3-pyridinyl)methyl]-1-methyl-3-(1-methylethyl)-5-(1-methyl-4-piperidinyl)-1H-indole-7-carboxamide

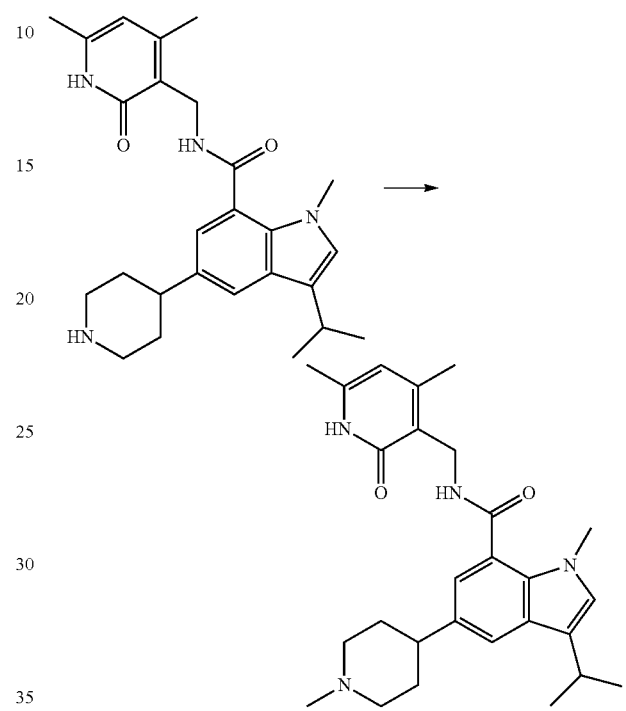

To a solution of N-[(4,6-dimethyl-2-oxo-1,2-dihydro-3-pyridinyl)methyl]-1-methyl-3-(1-methylethyl)-5-(4-piperidinyl)-1H-indole-7-carboxamide (0.13 g, 0.299 mmol) in 1,2-dichloroethane (3.0 mL) was added formaldehyde (0.223 mL, 2.99 mmol) and acetic acid (0.069 mL, 1.197 mmol). The mixture was stirred for 5 min, sodium triacetoxyborohydride (0.159 g, 0.748 mmol) was added, and stirring continued for another 6 h. The reaction was diluted with DCM and saturated aqueous NaHCO3. The layers were separated and the aqueous layer extracted with DCM. The combined organics were dried over magnesium sulfate, filtered, and concentrated in vacuo.

Purification: 12 gram Isco silica column was used. Gradient B: 20-100%. A: dichloromethane. B: 10% (2 M ammonia in methanol) in chloroform. The combined product fractions were concentrated in vacuo to give N-[(4,6-dimethyl-2-oxo-1,2-dihydro-3-pyridinyl)methyl]-1-methyl-3-(1-methylethyl)-5-(1-methyl-4-piperidinyl)-1H-indole-7-carboxamide (77 mg, 0.168 mmol, 56.2% yield). $^1$H NMR (400 MHz, DMSO-d6) δ ppm 1.26 (d, J=6.82 Hz, 6H) 1.63-1.79 (m, 4H) 1.96 (td, J=11.24, 3.03 Hz, 2H) 2.11 (s, 3H) 2.17-2.25 (m, 6H) 2.86 (d, J=11.37 Hz, 2H) 3.08-3.16 (m, 1H) 3.62 (s, 3H) 4.32 (d, J=5.05 Hz, 2H) 5.87 (s, 1H) 6.91 (d, J=1.52 Hz, 1H) 6.99 (s, 1H) 7.40 (d, J=1.52 Hz, 1H) 8.31 (t, J=4.93 Hz, 1H) 11.49 (s, 1H). MS (ES) [M+H]$^+$ 449.0.

Example 16

N-[(4,6-Dimethyl-2-oxo-1,2-dihydro-3-pyridinyl)methyl]-1-methyl-3-(1-methylethyl)-5-(4-morpholinyl)-1H-indole-7-carboxamide a) Methyl 5-bromo-1-methyl-3-(1-methylethyl)-1H-indole-7-carboxylate

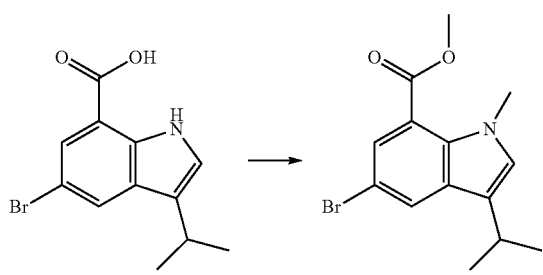 [SMILES: CC(C)c1c[nH]c2c(C(=O)O)cc(Br)cc12 ; COC(=O)c1cc(Br)cc2c(C(C)C)cn(C)c12]

To a stirred solution of 5-bromo-3-(1-methylethyl)-1H-indole-7-carboxylic acid (15 g, 53.2 mmol) in DMF (100 mL) at 0° C. was added iodomethane (13.25 mL, 212.7 mmol) followed by sodium hydride (2.8 g, 122.3 mmol). The reaction mixture was allowed to warm to room temperature and stirred for 2 h. The reaction mixture was concentrated in vacuo to dryness. The residue was diluted with water and ethyl acetate. The organic layer was separated and dried, filtered, and concentrated in vacuo. The crude product was purified by silica gel chromatography (eluent: 8% EtOAC in pet. ether) to afford methyl 5-bromo-1-methyl-3-(1-methylethyl)-1H-indole-7-carboxylate (10.58 g, 64%). $^1$H NMR (400 MHz, DMSO-d$_6$) δ ppm 1.23 (d, 6H, J=6.4 Hz), 3.10-3.19 (m, 1H), 3.74 (s, 3H), 3.92 (s, 3H), 7.22 (s, 1H), 7.58 (s, 1H), 7.95 (s, 1H). MS (ES)+m/e 310.1 [M+H]$^+$.

b) 1-Methyl-3-(1-methylethyl)-5-(4-morpholinyl)-1H-indole-7-carboxylic acid

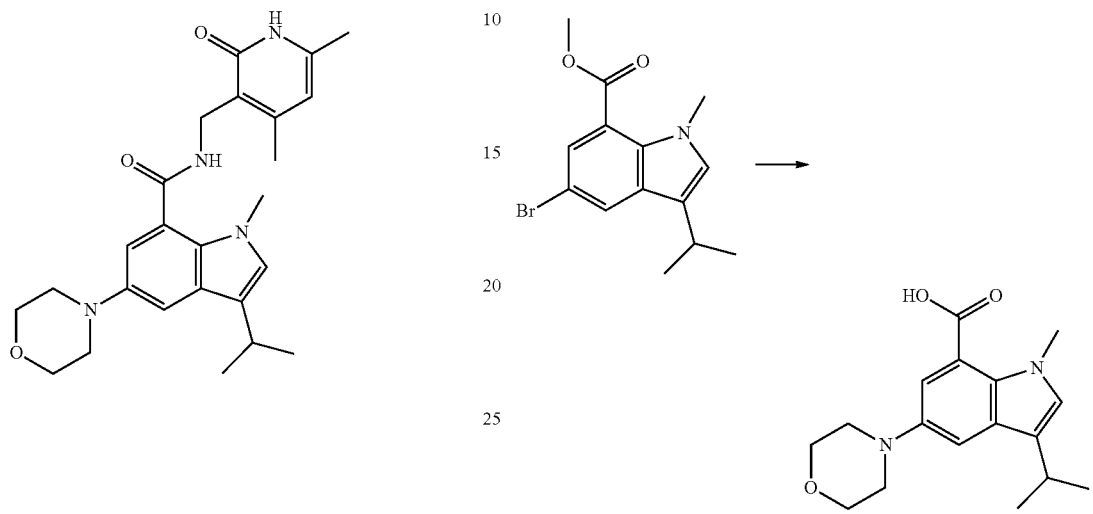

Methyl 5-bromo-1-methyl-3-(1-methylethyl)-1H-indole-7-carboxylate (200 mg, 0.65 mmol), sodium tert-butoxide (155 mg, 1.61 mmol), Pd-XPhos precatalyst (chloro(2-dicyclohexylphosphino-2',4',6'-tri-1-propyl-1,1'-biphenyl)[2-(2-aminoethyl)phenyl]Pd(II) Me-t-butylether adduct) (26.7 mg, 0.032 mmol) and morpholine (112 mg, 1.29 mmol) were suspended in dioxane (5 mL) in a sealed tube and the mixture was stirred at 98° C. overnight. The mixture was diluted with water and the pH was adjusted to 3-4 by the addition of 1 N HCl. It was extracted with EtOAc and DCM/isopropanol (8:2) and the combined organics were washed with brine, dried over MgSO$_4$, filtered and the solvent evaporated.

The residue was dissolved in DCM and purified using normal phase chromatography DCM/MeOH (gradient 0 to 80:20 in DCM). MeOH was added and it was further purified using a reversed-phase HPLC (30×100 Varian Polaris C18, 15-80% gradient of MeCN in water with 0.1% TFA over 12 minutes). Fractions containing the desired product were concentrated until a minimum of water remained, and a saturated solution of NaHCO$_3$ was added. Solids that crashed out were filtered, air-dried for 15 min and dried in vacuum-oven overnight to give 1-methyl-3-(1-methylethyl)-5-(4-morpholinyl)-1H-indole-7-carboxylic acid (125 mg, 62.2% yield). $^1$H NMR (400 MHz, DMSO-d$_6$) δ ppm 7.02-7.03 (m, 2H) 6.95 (s, 1H) 3.75-3.78 (m, 4H) 3.74 (s, 3H) 3.08 (d, J=6.82 Hz, 1H) 3.00-3.05 (m, 4H) 1.27 (s, 3H) 1.26 (s, 3H). MS (ES) [M+H]$^+$ 303.4.

c) N-[(4,6-Dimethyl-2-oxo-1,2-dihydro-3-pyridinyl)methyl]-1-methyl-3-(1-methylethyl)-5-(4-morpholinyl)-1H-indole-7-carboxamide

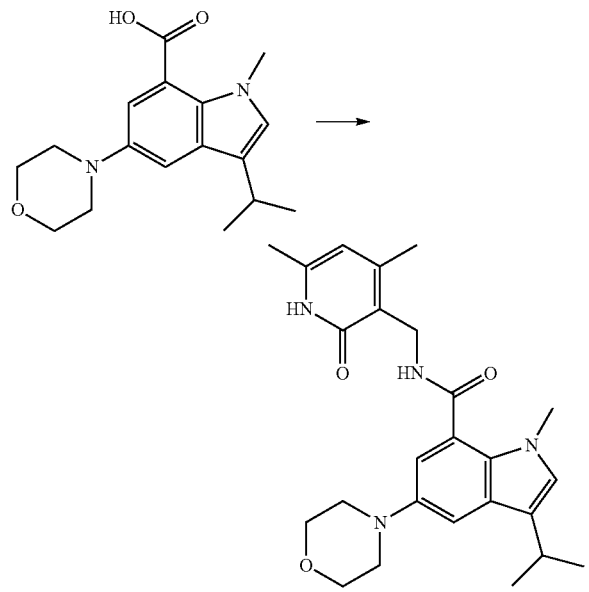

1-Methyl-3-(1-methylethyl)-5-(4-morpholinyl)-1H-indole-7-carboxylic acid (62.5 mg, 0.21 mmol), 3-(aminomethyl)-4,6-dimethyl-2(1H)-pyridinone.HCl (58.5 mg, 0.31 mmol) and 1-hydroxy-7-azabenzotriazole (47.8 mg, 0.35 mmol) were stirred in 2 mL of DMSO for 10 min under nitrogen. N-methylmorpholine (0.095 mL, 0.87 mmol) was added along with EDC (67.4 mg, 0.35 mmol) and the mixture was stirred at rt overnight under nitrogen. Ice-water was added but no solid crashed out. The reaction mixture was concentrated until only DMSO was left and purified using a reversed-phase HPLC (30×100 Varian Polaris C18, 15-80% gradient of MeCN in water with 0.1% TFA over 12 minutes). Fractions containing the desired product were evaporated until a minimum of water remained and saturated solution of NaHCO$_3$ was added. The light orange solids that crashed out were filtered off and dissolved in DMF. Water was added and the solids that crashed out were filtered, air-dried for 15 min and dried in vacuum-oven overnight to give N-[(4,6-dimethyl-2-oxo-1,2-dihydro-3-pyridinyl)methyl]-1-methyl-3-(1-methylethyl)-5-(4-morpholinyl)-1H-indole-7-carboxamide (24 mg, 26.1% yield). $^1$H NMR (400 MHz, DMSO-d$_6$) δ ppm 11.49 (s, 1H) 8.33 (t, J=4.93 Hz, 1H) 7.04 (d, J=2.27 Hz, 1H) 6.96 (s, 1H) 6.80 (d, J=2.27 Hz, 1H) 5.87 (s, 1H) 4.33 (s, 1H) 4.31 (s, 1H) 3.72-3.78 (m, 4H) 3.60 (s, 3H) 3.06-3.12 (m, 1H) 3.00-3.06 (m, 4H) 2.22 (s, 3H) 2.11 (s, 3H) 1.26 (d, J=6.8 Hz, 6H). MS (ES) [M+H]$^+$ 437.0.

Example 17

N-[(4-Ethyl-6-methyl-2-oxo-1,2-dihydro-3-pyridinyl)methyl]-1-methyl-3-(1-methylethyl)-5-(4-morpholinyl)-1H-indole-7-carboxamide

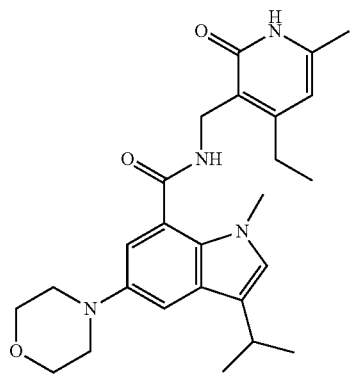 [SMILES: CCc1cc(C)[nH]c(=O)c1CNC(=O)c1cc(N2CCOCC2)cc2c(C(C)C)cn(C)c12]

The title compound was prepared in the same manner as described for Example 16c using 3-(aminomethyl)-4-ethyl-6-methyl-2(1H)-pyridinone hydrochloride (63 mg, 0.31 mmol). Obtained 62 mg of the title compound (67% yield). $^1$H NMR (400 MHz, DMSO-d$_6$) δ ppm 11.48 (br. s., 1H) 8.33 (t, J=4.80 Hz, 1H) 7.04 (d, J=2.27 Hz, 1H) 6.96 (s, 1H) 6.80 (d, J=2.27 Hz, 1H) 5.92 (s, 1H) 4.34 (s, 1H) 4.33 (br. s., 1H) 3.72-3.78 (m, 4H) 3.60 (s, 3H) 3.06-3.12 (m, 1H) 3.00-3.05 (m, 4H) 2.57 (q, J=7.41 Hz, 2H) 2.13 (s, 3H) 1.26 (d, J=7.6 Hz, 6H) 1.13 (t, J=7.58 Hz, 3H). MS (ES) [M+H]$^+$ 450.9.

Example 18

5-Bromo-N-[(4,6-dimethyl-2-oxo-1,2-dihydro-3-pyridinyl)methyl]-3-(1-methylethyl)-1H-indole-7-carboxamide

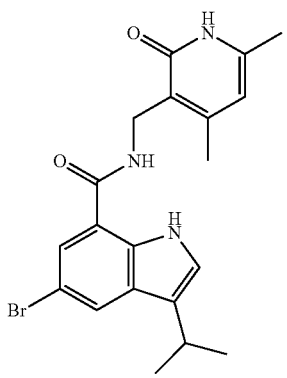 [SMILES: Cc1cc(C)c(CNC(=O)c2cc(Br)cc3c(C(C)C)c[nH]c23)c(=O)[nH]1]

To a stirred suspension of 5-bromo-3-(1-methylethyl)-1H-indole-7-carboxylic acid (400 mg, 1.418 mmol), 3-(aminomethyl)-4,6-dimethyl-2(1H)-pyridinone (300 mg, 1.590 mmol) and HOAt (220 mg, 1.616 mmol) in DMF (15 mL) was added N-methylmorpholine (180 μL, 1.637 mmol) and EDC free base (330 mg, 2.127 mmol). The reaction was stirred for 18 h at RT. LCMS showed that the reaction was complete. The reaction was evaporated to near dryness under vacuum. Water (~15 mL) was added and the solids which precipitated out were triturated, filtered and dried under vacuum to give 5-bromo-N-[(4,6-dimethyl-2-oxo-1,2-dihydro-3-pyridinyl)methyl]-3-(1-methylethyl)-1H-indole-7-carboxamide (571 mg, 1.372 mmol, 97% yield) as a white solid. ¹H NMR (400 MHz, DMSO-d6) δ ppm 11.52 (br. s., 1H), 11.03 (br. s., 1H), 8.58 (t, J=4.55 Hz, 1H), 7.85 (d, J=1.26 Hz, 1H), 7.82 (s, 1H), 7.12 (d, J=2.02 Hz, 1H), 5.89 (s, 1H), 4.35 (d, J=4.55 Hz, 2H), 3.13 (ddd, J=6.57, 6.69, 13.52 Hz, 1H), 2.20 (s, 3H), 2.13 (s, 3H), 1.27 (d, J=6.82 Hz, 6H). MS (ES) [M+H]⁺ 415.9, 418.0.

Example 19

N-((4,6-Dimethyl-2-oxo-1,2-dihydropyridin-3-yl)methyl)-3-isopropyl-1-methyl-5-(methylsulfonyl)-1H-indole-7-carboxamide

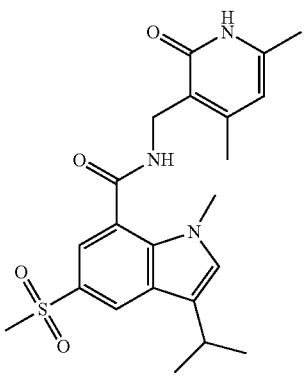

a) Methyl 3-isopropyl-1-methyl-5-(methylsulfonyl)-1H-indole-7-carboxylate

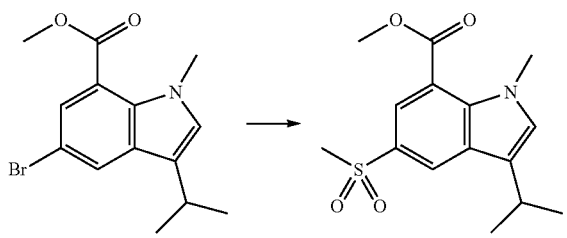 [SMILES: COC(=O)c1cc(Br)cc2c(C(C)C)cn(C)c12 ; COC(=O)c1cc(S(C)(=O)=O)cc2c(C(C)C)cn(C)c12]

Methyl 5-bromo-3-isopropyl-1-methyl-1H-indole-7-carboxylate (502 mg, 1.62 mmol), methanesulfinic acid, Sodium salt (811 mg, 7.9 mmol) and copper(I) iodide 1.51 g, 7.9 mmol) were suspended in N-Methyl-2-pyrrolidone (5 mL) in a sealed vial and the mixture was stirred at 150° C. for 10 hours. The suspension was cooled down, EtOAc was added and insoluble materials were removed by filtration. The filtrate was extracted with EtOAc and DCM and the combined organics were washed with brine, dried over MgSO₄, filtered and the solvent evaporated. The residue was purified using normal phase chromatography Hexanes/EtOAc (gradient 0 to 100% EtOAc). Solids that crashed out were filtered, air-dried for 15 min and dried in vacuum-oven overnight to give 1-methyl-3-(1-methylethyl)-5-(4-morpholinyl)-1H-indole-7-carboxylic acid (125 mg, 62.2% yield). EtOAc was added along with some hexanes, it was sonicated, the solids that crashed out were filtered, air-dried for 15 min and dried in vacuum-oven overnight to give methyl 3-isopropyl-1-methyl-5-(methylsulfonyl)-1H-indole-7-carboxylate (198 mg, 39%). ¹H NMR (400 MHz, DMSO-d₆) δ ppm 1.31 (s, 3H) 1.33 (s, 3H) 3.22-3.28 (m, 4H) 3.82 (s, 3H) 3.96 (s, 3H) 7.43 (s, 1H) 7.99 (d, J=1.77 Hz, 1H) 8.32 (d, J=1.77 Hz, 1H). MS (ES) [M+H]⁺ 310.1.

b) 3-Isopropyl-1-methyl-5-(methylsulfonyl)-1H-indole-7-carboxylic acid

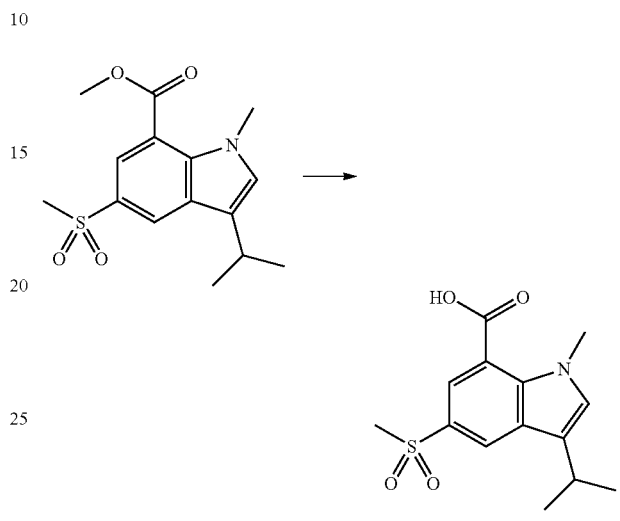

Methyl 3-isopropyl-1-methyl-5-(methylsulfonyl)-1H-indole-7-carboxylate (500 mg, 1.61 mmol) in THF/MeOH (3:1 mL) was treated with 5N NaOH (3 mL). The yellow biphasic solution was stirred at room temperature under nitrogen overnight. 6N HCl was added to pH 4 and the solution was stirred at room temperature for 2 hours. Solids were filtered and dried in vacuum-oven for 3 hours to give 3-isopropyl-1-methyl-5-(methylsulfonyl)-1H-indole-7-carboxylic acid (167 mg, 35%). ¹H NMR (400 MHz, CHLOROFORM-d) δ ppm 1.39 (d, J=6.8 Hz, 6H) 3.15 (s, 3H) 3.27 (quin, J=6.82 Hz, 1H) 3.95-4.02 (m, 3H) 7.03 (s, 1H) 8.40 (d, J=2.02 Hz, 1H) 8.45 (d, J=1.77 Hz, 1H) MS (ES). [M+H]⁺ 296.2.

c) N-((4,6-Dimethyl-2-oxo-1,2-dihydropyridin-3-yl)methyl)-3-isopropyl-1-methyl-5-(methylsulfonyl)-1H-indole-7-carboxamide

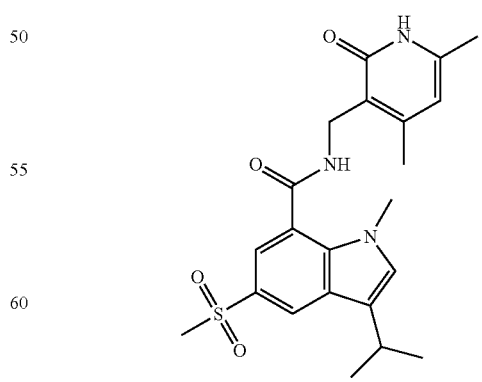

3-Isopropyl-1-methyl-5-(methylsulfonyl)-1H-indole-7-carboxylic acid (80.7 mg, 0.27 mmol), 3-(aminomethyl)-4,6-dimethyl-2(1H)-pyridinone hydrochloride (66.2 mg, 0.35 mmol) and 1-hydroxy-7-azabenzotriazole (56.7 mg, 0.42 mmol) were stirred in 3 mL of DMSO for 10 min under nitrogen. N-methylmorpholine (0.12 mL, 1.09 mmol) was added along with EDC (78.3 mg, 0.41 mmol) and the mixture was stirred at room temperature for 19 hours. Ice-water (15 mL) and a concentrated solution of potassium carbonate were added to pH 10 and the solution was stirred for 40 minutes at room temperature. The solids were filtered, washed with water and dried. DMF was added along with water, solids were filtered and dried in vacuum-oven overnight to give N-((4,6-dimethyl-2-oxo-1,2-dihydropyridin-3-yl)methyl)-3-isopropyl-1-methyl-5-(methylsulfonyl)-1H-indole-7-carboxamide (88 mg, 73%). $^1$H NMR (400 MHz, DMSO-d$_6$) δ ppm 1.31 (d, J=6.8 Hz, 6H) 2.12 (s, 3H) 2.24 (s, 3H) 3.18-3.26 (m, 4H) 3.71-3.75 (m, 3H) 4.36 (d, J=4.80 Hz, 2H) 5.89 (s, 1H) 7.33 (s, 1H) 7.51 (d, J=1.77 Hz, 1H) 8.14 (d, J=2.02 Hz, 1H) 8.65 (t, J=4.93 Hz, 1H) 11.52 (s, 1H). MS (ES) [M+H]$^+$ 430.3.

Example 20

N-[(4,6-Dimethyl-2-oxo-1,2-dihydro-3-pyridinyl)methyl]-1-methyl-3-(1-methylethyl)-5-(methyloxy)-1H-indole-7-carboxamide

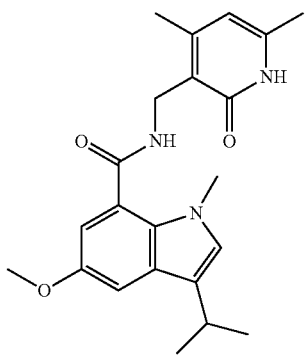

a) 1-Methyl-3-(1-methylethyl)-5-(methyloxy)-1H-indole-7-carboxylic acid

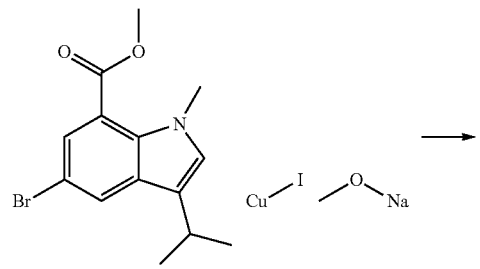

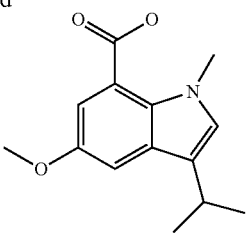

To methyl 5-bromo-1-methyl-3-(1-methylethyl)-1H-indole-7-carboxylate (620 mg, 2 mmol) and Copper(I)iodide (476 mg, 2.500 mmol) was added N-Methyl-2-pyrrolidone (NMP) (4 mL). To the mixture was added dropwise a solution of sodium methoxide (in methanol) (1802 mg, 8.34 mmol) with stirring over a 5 min period, during which time contents turned dark green. The reaction was heated to 120° C., upon which the contents were nearly black colored. The black colored mixture was stirred at 120° C. After 1 h 45 min, the dark reddish brown colored contents were removed from heating and allowed to cool. Upon reaching 80° C., water (150 uL) was added and the reaction mixture was allowed to cool to room temperature with stirring overnight. The reaction contents were then acidified with 1N HCl (8 mL), upon which the contents became a brown suspension. The mixture was diluted with water (8 mL), and lightened a bit. Next added EtOAc (10 mL), and the contents become a biphasic mixture. The contents were filtered through Celite, and the filter cake was washed with EtOAc. The filtrate was poured into a separatory funnel, and the organic phase was separated and set aside. The aq. phase was extracted with EtOAc (2×10 mL), and combined with the previously saved organic layer. The combined organic layers were washed with brine (10 mL), dried (MgSO$_4$), filtered, and concentrated under vacuum. Purification by silica gel chromatography (gradient: 10 to 50% EtOAc in hexanes) gave the title compound as a cream colored solid (80 mg, 16%). Note: Some material loss occurred during purification due to a collection malfunction. $^1$H NMR (400 MHz, DMSO-d$_6$) δ ppm 1.28 (d, J=6.82 Hz, 6H), 3.08-3.16 (m, 1H), 3.74 (s, 3H), 3.80 (s, 3H), 7.09 (s, 2H), 7.21 (s, 1H), 12.9-13.1 (br s, 1H). MS(ES) [M+H]$^+$ 248.2.

b) N-[(4,6-Dimethyl-2-oxo-1,2-dihydro-3-pyridinyl)methyl]-1-methyl-3-(1-methylethyl)-5-(methyloxy)-1H-indole-7-carboxamide

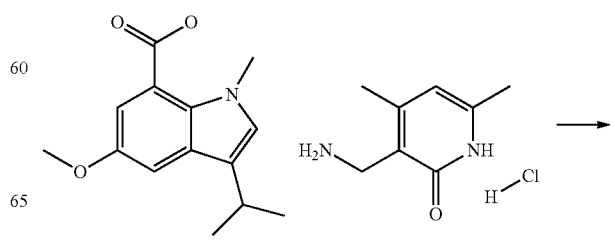

-continued

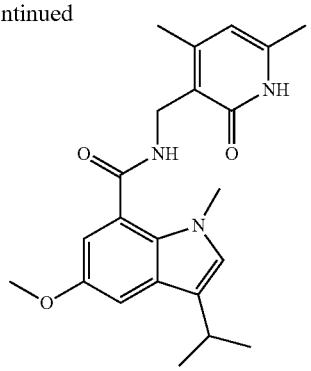

To a stirred suspension of 1-methyl-3-(1-methylethyl)-5-(methyloxy)-1H-indole-7-carboxylic acid (78 mg, 0.315 mmol), 3-(aminomethyl)-4,6-dimethyl-2(1H)-pyridinone hydrochloride (59.5 mg, 0.315 mmol), HOAt (64 mg, 0.473 mmol) in DMF (4 mL) was added EDC (121 mg, 0.631 mmol) and N-methylmorpholine (52 µL, 0.473 mmol). The reaction mixture was stirred for 18 hr at room temperature, after which time the contents were evaporated to near dryness. Water (~5 mL) was added and the solids which precipitated out were isolated. The collected solid was dissolved in DCM/MeOH (4:1, 5 mL), dried over MgSO$_4$, filtered, and concentrated in vacuo to a afford a creme colored solid. The solid was re-dissolved in DCM/MeOH (4:1, 5 mL) and washed with 6N NaOH (1 mL) and water (4 mL). The organic layer was concentrated in vacuo to afford a nearly white solid.

The crude product was then dissolved in DCM/MeOH (4:1, 2 mL) and purified by silica gel chromatography (eluent: 1 to 5% gradient MeOH in CH$_2$Cl$_2$). The title compound was collected as a white solid (80 mg, 67%). $^1$H NMR (400 MHz, DMSO-d$_6$) ppm 1.26 (d, J=6.82 Hz, 6H), 2.11 (s, 3H), 2.20 (s, 3H), 3.05-3.15 (m, 1H), 3.61 (s, 3H), 3.77 (s, 3H), 4.32 (d, J=5.05 Hz, 2H), 5.87 (s, 1H), 6.66 (d, J=2.27 Hz, 1H), 7.00 (s, 1H), 7.05 (d, J=2.27 Hz, 1H), 8.35 (s, 1H), 11.4-11.6 (br s, 1H). MS (ES) [M+H]$^+$ 382.1.

Example 21

N-((4-Benzyl-6-methyl-2-oxo-1,2-dihydropyridin-3-yl)methyl)-5-bromo-3-isopropyl-1-methyl-1H-indole-7-carboxamide

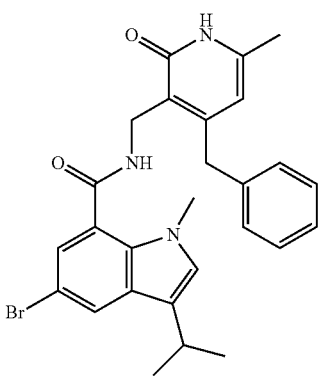 [SMILES: Cc1cc(Cc2ccccc2)c(CNC(=O)c2cc(Br)cc3c(C(C)C)cn(C)c23)c(=O)[nH]1]

A 20 mL, oven dried vial was charged with 5-bromo-1-methyl-3-(1-methylethyl)-1H-indole-7-carboxylic acid (0.075 g, 0.253 mmol), 3-(aminomethyl)-4-benzyl-6-methylpyridin-2(1H)-one hydrochloride (0.080 g, 0.304 mmol), 1-hydroxy-7-azabenzotriazole (0.041 g, 0.304 mmol) and EDC (0.058 g, 0.304 mmol). Dimethyl sulfoxide (DMSO) (2 mL) was added via syringe, followed by N-methylmorpholine (0.111 mL, 1.013 mmol). The mixture was capped and stirred at RT over weekend. The reaction was poured into 60 mL water and the resultant mixture stirred for 10 min, then placed in a freezer for 10 min. The solids were filtered, washed with water (10 mL), air dried for 5 min, and placed in a vacuum oven (40° C.) for 2 h. Collected the solids and further dried in a vacuum oven (45° C.) for 18 h to give N-((4-benzyl-6-methyl-2-oxo-1,2-dihydropyridin-3-yl)methyl)-5-bromo-3-isopropyl-1-methyl-1H-indole-7-carboxamide (120 mg, 0.225 mmol, 89% yield). $^1$H NMR (400 MHz, DMSO-d6) δ ppm 11.58 (s, 1H), 8.63 (t, J=4.9 Hz, 1H), 7.75 (d, J=1.8 Hz, 1H), 7.30 (m, 2H), 7.22 (m, 3H), 7.13 (s, 1H), 7.05 (d, J=1.8 Hz, 1H), 5.78 (s, 1H), 4.39 (d, J=4.8 Hz, 2H), 3.96 (s, 2H), 3.64 (s, 3H), 3.11 (dt, J=13.6, 6.8 Hz, 1H), 2.09 (s, 3H), 1.26 (m, 6H). MS (ES) [M+H]$^+$ 506.3.

Example 22

5-Bromo-1-methyl-3-(1-methylethyl)-N-[(4-methyl-2-oxo-1,2-dihydro-3-pyridinyl)methyl]-1H-indole-7-carboxamide

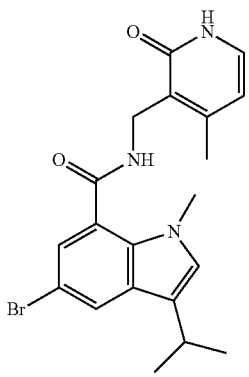 [SMILES: Cc1cc[nH]c(=O)c1CNC(=O)c1cc(Br)cc2c(C(C)C)cn(C)c12]

A 20 mL, oven dried vial was charged with 5-bromo-1-methyl-3-(1-methylethyl)-1H-indole-7-carboxylic acid (0.10 g, 0.338 mmol), 3-(aminomethyl)-4-methyl-2(1H)-pyridinone (0.088 g, 0.506 mmol), 1-hydroxy-7-azabenzotriazole (0.069 g, 0.506 mmol) and EDC (0.097 g, 0.506 mmol). To the mixture was added dimethyl sulfoxide (DMSO) (3 mL) via syringe, followed by N-methylmorpholine (0.148 mL, 1.351 mmol). The mixture was capped and stirred at RT overnight. The reaction was poured into 60 mL water and the resultant mixture stirred for 10 min, then placed in a freezer for 10 min. The solids were filtered, washed with water (10 mL), air dried for 5 min, and placed in a vacuum oven (40° C.). The solid was dissolved in DCM/MeOH and absorbed onto silica gel and concentrated in vacuo to dryness. Purification by column chromatography (12 g Isco GOLD silica column; Gradient B: 5-85%, A: dichloromethane, B: 10% 2 M ammonia/methanol in chloroform) gave 5-bromo-1-methyl-3-(1-methylethyl)-N-[(4-methyl-2-oxo-1,2-dihydro-3-pyridinyl)methyl]-1H-indole-7-carboxamide (85 mg, 0.200 mmol, 59.3% yield). $^1$H NMR (400 MHz, DMSO-d6) δ ppm 1.25 (d, J=6.82 Hz, 6H) 2.26 (s, 3H) 3.03-3.17 (m, 1H) 3.64 (s, 3H) 4.34 (d, J=4.80 Hz, 2H) 6.05 (d, J=6.57 Hz, 1H) 7.09

(d, J=1.77 Hz, 1H) 7.14 (s, 1H) 7.22 (d, J=6.82 Hz, 1H) 7.75 (d, J=1.77 Hz, 1H) 8.57 (t, J=4.80 Hz, 1H) 11.48 (br. s., 1H). MS (ES) [M+H]$^+$ 415.9.

Example 23

N-[(4,6-Dimethyl-2-oxo-1,2-dihydro-3-pyridinyl)methyl]-1-methyl-3-(1-methylethyl)-1H-indole-7-carboxamide

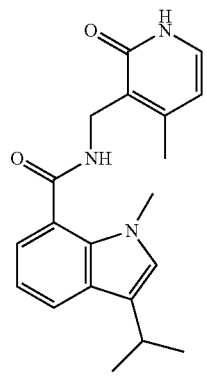 [SMILES: Cc1cc[nH]c(=O)c1CNC(=O)c1cccc2c(C(C)C)cn(C)c12]

To a dried 50 mL round bottom flask, equipped with a stir bar and H$_2$/N$_2$ inlet was added 10% Pd/C(degussa) (0.025 g, 0.012 mmol). The vessel was degassed with N$_2$ and EtOH (~0.5 mL) was added. To the slurry was added a solution of 5-bromo-N-[(4,6-dimethyl-2-oxo-1,2-dihydro-3-pyridinyl)methyl]-1-methyl-3-(1-methylethyl)-1H-indole-7-carboxamide (0.10 g, 0.232 mmol) (solid) in ethanol (6 mL) and hot tetrahydrofuran (THF) (1.0 mL), followed by triethylamine (0.032 mL, 0.232 mmol). The reaction was placed back under N$_2$ and stirred for 5 min, then evacuated/refilled with H$_2$ (3×). The reaction was stirred under a H$_2$ balloon for 4 h. The reaction was then evacuated/refilled with N$_2$ and diluted with DCM (10 mL). A small amount of Celite was added and the reaction stirred for 10 min. The mixture was filtered through analytical grade Celite and washed with successively with 10% MeOH/DCM, EtOH, and DCM. The organics were concentrated and dried on hivac overnight. The residue was dissolved in MeOH/DCM, absorbed onto silica gel, and concentrated in vacuo to dryness. Purification by column chromatography (4 g Isco silica column; Gradient B: 5-85%, A: dichloromethane, B: 10% 2M ammonia/methanol in chloroform) gave N-[(4,6-dimethyl-2-oxo-1,2-dihydro-3-pyridinyl)methyl]-1-methyl-3-(1-methylethyl)-1H-indole-7-carboxamide (77 mg, 0.215 mmol, 92% yield). $^1$H NMR (400 MHz, DMSO-d6) δ ppm 1.27 (d, J=7.07 Hz, 6H) 2.11 (s, 3H) 2.22 (s, 3H) 3.06-3.19 (m, 1H) 3.65 (s, 3H) 4.33 (d, J=4.80 Hz, 2H) 5.86 (s, 1H) 6.91-6.99 (m, 1H) 6.99-7.08 (m, 2H) 7.59 (dd, J=7.83, 1.26 Hz, 1H) 8.31 (t, J=4.93 Hz, 1H) 11.47 (s, 1H). MS (ES) [M+H]$^+$ 352.4.

Example 24

5-Cyclopropyl-N-((4,6-dimethyl-2-oxo-1,2-dihydropyridin-3-yl)methyl)-3-isopropyl-1-methyl-1H-indole-7-carboxamide

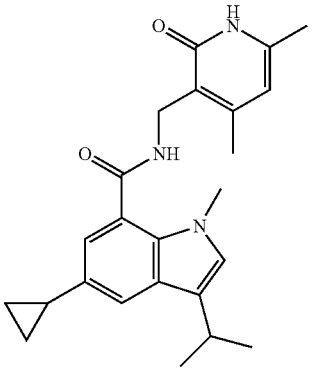 [SMILES: Cc1cc(C)c(CNC(=O)c2cc(C3CC3)cc3c(C(C)C)cn(C)c23)c(=O)[nH]1]

a) 5-Cyclopropyl-3-isopropyl-1-methyl-1H-indole-7-carboxylic acid

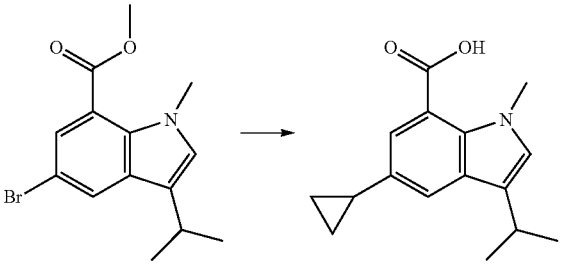 [SMILES: COC(=O)c1cc(Br)cc2c(C(C)C)cn(C)c12 ; CC(C)c1cn(C)c2c(C(=O)O)cc(C3CC3)cc12]

To a vial containing methyl 5-bromo-3-isopropyl-1-methyl-1H-indole-7-carboxylate (0.40 g, 1.290 mmol), potassium cyclopropyltrifluoroborate (0.382 g, 2.58 mmol) and potassium phosphate (0.821 g, 3.87 mmol) was added 1,4-dioxane (5 mL) and water (1.25 mL). The mixture was degassed with argon for 10 min and then was added S-Phos (0.106 g, 0.258 mmol) and palladium(II) acetate (0.029 g, 0.129 mmol). The reaction was sealed and heated in a heat block at 115° C. for 20 h. Added more potassium cyclopropyltrifluoroborate (0.250 g), S-Phos (0.100 g) and palladium (II) acetate (0.030 g, 0.129 mmol) and continued heating overnight (18 h) at 115° C. The reaction mixture was then concentrated and the residue purified by column chromatography (40 g Isco silica column; Gradient B: 0-50%, A: hexane, B: ethyl acetate) to give a clear oil (140 mg).

To a solution of the crude oil in THF (1 mL) and MeOH (3 mL) was added 3 M NaOH (0.5 mL) and the reaction maintained at RT for 10 days. The volatiles were removed in vacuo and the residue dissolved in water (5 mL). Slowly acidified to pH 4-5 with 1M HCl and cool in an ice bath for 1 h. The solids were filtered, washed with a small amount of water, and dried in vac oven (45° C.) for 18 h to give 5-cyclopropyl-3-isopropyl-1-methyl-1H-indole-7-carboxylic acid (87 mg, 0.304 mmol, 23.60% yield), which was used without further purification. MS (ES) [M+H]$^+$ 258.2.

b) 5-Cyclopropyl-N-((4,6-dimethyl-2-oxo-1,2-dihydropyridin-3-yl)methyl)-3-isopropyl-1-methyl-1H-indole-7-carboxamide

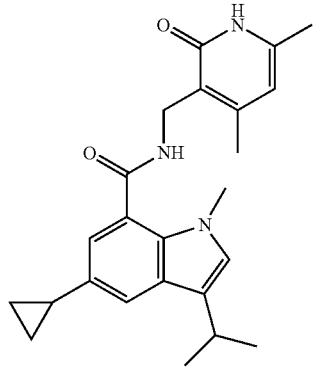 [SMILES: Cc1cc(C)c(CNC(=O)c2cc(C3CC3)cc3c(C(C)C)cn(C)c23)c(=O)[nH]1]

Following the general procedure of Example 22, 5-cyclopropyl-N-((4,6-dimethyl-2-oxo-1,2-dihydropyridin-3-yl)methyl)-3-isopropyl-1-methyl-1H-indole-7-carboxamide (79 mg, 0.198 mmol, 59.9% yield) was isolated. $^1$H NMR (400 MHz, DMSO-d6) δ ppm 11.46 (br. s., 1H), 8.31 (t, J=4.9 Hz, 1H), 7.29 (d, J=1.5 Hz, 1H), 6.98 (s, 1H), 6.74 (d, J=1.5 Hz, 1H), 5.86 (s, 1H), 4.31 (d, J=5.1 Hz, 2H), 3.60 (s, 3H), 3.09 (dt, J=13.6, 6.8 Hz, 1H), 2.21 (s, 3H), 2.10 (m, 3H), 1.98 (m, 1H), 1.27 (m, 6H), 0.89 (m, 2H), 0.64 (m, 2H). MS (ES) [M+H]$^+$ 392.3.

Example 25

N-((4,6-dimethyl-2-oxo-1,2-dihydropyridin-3-yl)methyl)-3-isopropyl-5-(2-methoxythiazol-5-yl)-1-methyl-1H-indole-7-carboxamide

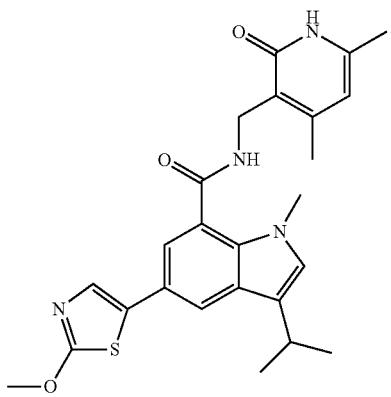

a) N-((4,6-dimethyl-2-oxo-1,2-dihydropyridin-3-yl)methyl)-3-isopropyl-1-methyl-5-(4,4,5,5-tetramethyl-1,3,2-dioxaborolan-2-yl)-1H-indole-7-carboxamide

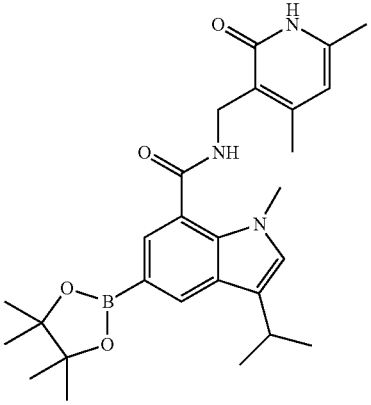

To a mixture of 5-bromo-N-((4,6-dimethyl-2-oxo-1,2-dihydropyridin-3-yl)methyl)-3-isopropyl-1-methyl-1H-indole-7-carboxamide (0.5 g, 1.162 mmol) solid, potassium acetate (0.228 g, 2.324 mmol) and bis(pinacolato)diboron (0.354 g, 1.394 mmol) was added 1,4-dioxane (6 mL). The reaction was degassed with argon for 10 min. PdCl2(dppf)-CH$_2$Cl$_2$ adduct (0.095 g, 0.116 mmol) was then added and the mixture degassed for 1 min. The reaction was sealed and heated in a heat block at 85° C. for ~20 h (overnight). The mixture was poured into ice/water (100 mL) and EtOAc (60 mL) was added. The suspension was filtered through Celite and washed with EtOAc. The layers were separated and saturated NH$_4$Cl was added to the aqueous layer. The combined aqueous was further extracted with EtOAc (2×). and the combined organics dried over magnesium sulfate, filtered and concentrated to a brown oil. Purification of the residue by column chromatography (40 gram Isco GOLD silica column; Gradient B: 3-60%, A: dichloromethane, B: 10% methanol/dichloromethane+0.1% AcOH). The resultant light brown oil was triturated with TBME to give N-((4,6-dimethyl-2-oxo-1,2-dihydropyridin-3-yl)methyl)-3-isopropyl-1-methyl-5-(4,4,5,5-tetramethyl-1,3,2-dioxaborolan-2-yl)-1H-indole-7-carboxamide (0.52 g, 0.871 mmol, 75.0% yield) as a tan glassy solid. MS (ES) [M+H]$^+$ 478.5.

b) N-((4,6-dimethyl-2-oxo-1,2-dihydropyridin-3-yl)methyl)-3-isopropyl-5-(2-methoxythiazol-5-yl)-1-methyl-1H-indole-7-carboxamide

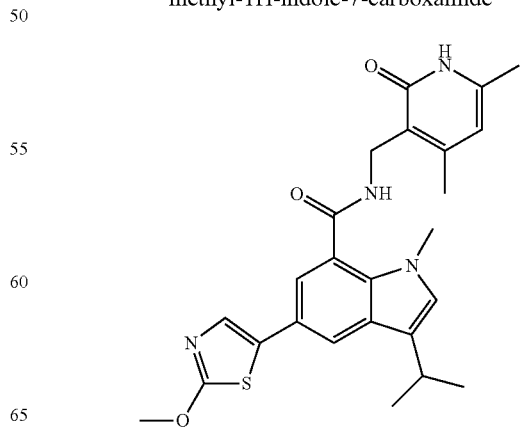

To a vessel containing N-((4,6-dimethyl-2-oxo-1,2-dihydropyridin-3-yl)methyl)-3-isopropyl-1-methyl-5-(4,4,5,5-tetramethyl-1,3,2-dioxaborolan-2-yl)-1H-indole-7-carboxamide (0.150 g, 0.314 mmol) and sodium bicarbonate (0.106 g, 1.257 mmol) was added a solution of 5-bromo-2-methoxythiazole (0.067 g, 0.346 mmol) in 1,4-dioxane (3 mL) and water (1 mL). The mixture was degassed with argon for 10 min, then was added tetrakis(triphenylphosphine)palladium (0) (0.036 g, 0.031 mmol) and the resultant mixture degassed for 1 min and heated in a Biotage microwave reactor at 120° C. for 60 min. The reaction was diluted with EtOAc and adsorbed onto silica gel. Purification by column chromatography (12 gram Isco GOLD silica column; A: dichloromethane, B: 10% 2 M ammonia/methanol in chloroform) to give an oil. The residue was triturated with TBME to give a the title compound contaminated with ~14% of the proton quench product. Purification by prep HPLC (Sunfire 30×75 mm; Gradient B: 25-85%, A: water+0.1% TFA, B: $CH_3CN$+ 0.1% TFA) to give fractions. The combined fractions were concentrated in vacuo to give an aqueous suspension. Neutralized the mixture $NaHCO_3$ to pH 7.5 and stirred in an ice bath for 30 min. The solids were filtered, washed with water, and dried in vac oven (50° C.) to give N-((4,6-dimethyl-2-oxo-1,2-dihydropyridin-3-yl)methyl)-3-isopropyl-5-(2-methoxythiazol-5-yl)-1-methyl-1H-indole-7-carboxamide (0.064 g, 0.135 mmol, 43% yield). $^1$H NMR (400 MHz, DMSO-d6) δ ppm 11.50 (s, 1H), 8.50 (t, J=4.9 Hz, 1H), 7.68 (d, J=1.8 Hz, 1H), 7.51 (s, 1H), 7.19 (d, J=1.8 Hz, 1H), 7.10 (s, 1H), 5.87 (s, 1H), 4.34 (d, J=5.1 Hz, 2H), 4.04 (s, 3H), 3.65 (s, 3H), 3.16 (m, 1H), 2.23 (s, 3H), 2.11 (s, 3H), 1.28 (d, J=6.8 Hz, 6H) MS (ES) [M+H]$^+$ 465.4.

INTERMEDIATES

Intermediate 1

3-(Aminomethyl)-4,6-dimethyl-2(1H)-pyridinone hydrochloride

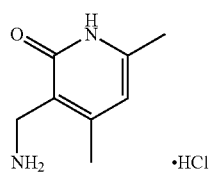

Palladium on carbon (10%) (3.24 g) was charged into a 2 L dry Parr bottle and a small amount of acetic acid was added. Next added 4,6-dimethyl-2-oxo-1,2-dihydro-pyridine-3-carbonitrile (30 g, 202.7 mmol), sodium acetate (30.75 g, 375.0 mmol), platinum oxide (0.218 g), and acetic acid (1 L). The bottle was capped, placed on Parr apparatus, and shaken under an atmosphere of $H_2$ (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, ether, and dried. The product was collected as 36 g. This batch was combined with other batches prepared on smaller scales and triturated with ether to give 51 g of pure compound. $^1$H NMR (400 MHz, DMSO-d6) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(Aminomethyl)-6-methyl-4-(trifluoromethyl)-2 (1H)-pyridinone

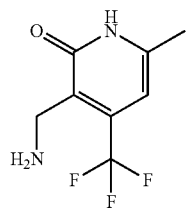

To a dried 500 mL Parr bottle equipped with nitrogen inlet were added sodium acetate (1.502 g, 18.30 mmol), 10% palladium on carbon (1.579 g, 0.742 mmol), platinum(IV) oxide (0.011 g, 0.049 mmol) and a small amount of acetic acid to wet the catalysts, under nitrogen stream. Next was added 2-hydroxy-6-methyl-4-(trifluoromethyl)-3-pyridinecarbonitrile (2.0 g, 9.89 mmol) followed by acetic acid (175 mL) while under nitrogen atmosphere. The contents were sealed, placed on a Parr shaker, and reacted at 40 psi of $H_2$ for ca. 6 hr, keeping the $H_2$ psi between 20 and 40 psi (vessel was refilled twice). The vessel was purged with nitrogen and the reaction mixture filtered through Celite, and the filter pad was further washed with a small amount of acetic acid. The volatiles were removed in vacuo to afford a residue, which was dried under high vacuum for 45 min The solid was suspended in conc. HCl (12 mL), stirred, and filtered. The clear filtrate was concentrated in vacuo and the residue dried under high vacuum. The collected solid was suspended in conc. HCl (2 mL) and diluted with EtOH (13 mL). The contents were agitated and stored at ca. 0° C. (freezer) for 30 min to give a white solid. The solid was filtered and washed with cold ethanol (5 mL). The solid was filtered and dried in vacuum oven for 1 h to give 3-(aminomethyl)-6-methyl-4-(trifluoromethyl)-2(1H)-pyridinone (0.95 g, 40%). LCMS E-S (M+H)=206.9. $^1$H NMR (400 MHz, DMSO-d$_6$) δ ppm 2.31 (s, 3H), 3.40-3.62 (m, 2H), 3.87 (d, J=5.05 Hz, 2H), 8.12-8.37 (m, 3H).

Intermediate 3

3-(Aminomethyl)-4-cyclohexyl-6-methyl-2(1H)-pyridinone

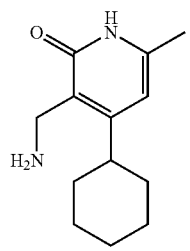 [SMILES: Cc1cc(C2CCCCC2)c(CN)c(=O)[nH]1]

3a) 4-Cyclohexyl-6-methyl-2-oxo-1,2-dihydro-3-pyridinecarbonitrile

To a stirred suspension of CrCl$_2$ (58 g, 472.8 mmol) in THF (1500 mL) was added a THF solution (500 mL) of 1,1-dichloro-2-propanone (10 g, 78.8 mmol) and cyclohexanecarbaldehyde (8.84 g, 78.8 mmol). The reaction mixture was heated at reflux for 2 h, and then quenched by the addition of 1.0 M HCl. The reaction mixture was filtered through a pad of Celite and concentrated in vacuo. The crude residue (10 g) was added to a solution of DMSO (150 mL) containing t-BuOK (7.5 g, 65.7 mmol) and cyanoacetamide (6.1 g, 72.3 mmol) and stirred at room temperature for 30 min Additional t-BuOK (22.5 g, 197.1 mmol) was added and the reaction mixture was stirred under an atmosphere of oxygen for an additional 1 h. The contents were purged with argon, diluted with 4 volumes of H$_2$O, and then 5 volumes of 4 N HCl, which were added slowly. The reaction mixture was filtered, washed with water and dried to give 4-cyclohexyl-6-methyl-2-oxo-1,2-dihydro-3-pyridinecarbonitrile (4.5 g, 32%). $^1$H NMR (400 MHz, DMSO-d$_6$) δ ppm 6.25 (s, 1H), 2.61-2.65 (m, 1H), 2.22 (s, 3H), 1.66-1.79 (m, 4H), 1.24-1.46 (m, 6H).

3b) 3-(Aminomethyl)-4-cyclohexyl-6-methyl-2(1H)-pyridinone

To an ice-bath cooled THF (100 mL) solution of the product from step 1 (2 g, 9.26 mmol) was added NaBH$_4$ (0.81 g, 21.3 mmol) and I$_2$ (2.3 g, 9.26 mmol), and the mixture stirred for 30 min The reaction mixture was then heated at reflux for 3 h, and then allowed to cool to room temperature. After cooling to 0° C., the reaction mixture was acidified by slow addition of 3 N HCl (1 mL). The reaction mixture was concentrated in vacuo and the crude product purified by reverse phase HPLC to give 3-(aminomethyl)-4-cyclohexyl-6-methyl-2(1H)-pyridinone as a solid (0.5 g, 25%). LCMS E-S (M+H)=221.1. $^1$H NMR (400 MHz, DMSO-d$_6$) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 4

3-(Aminomethyl)-4-cyclopropyl-6-methyl-2(1H)-pyridinone

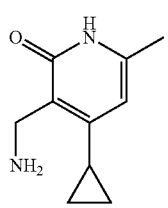

The title compound was prepared in the same manner as described for 3-(aminomethyl)-4-cyclohexyl-6-methyl-2 (1H)-pyridinone (Intermediate 3) using 4-cyclopropyl-6-methyl-2-oxo-1,2-dihydro-3-pyridinecarbonitrile (5 g, 28.7 mmol). Obtained: 0.50 g (10%). LCMS E-S (M+H)=179.1. $^1$H NMR (400 MHz, DMSO-d$_6$) δ ppm 11.76-11.78 (br s, 1H), 7.82-7.92 (br s, 3H), 5.61 (s, 1H), 3.94-3.99 (m, 2H), 2.11 (s, 3H), 1.98-2.05 (m, 1H), 0.95-1.01 (m, 2H), 0.74-0.79 (m, 2H).

Intermediate 5

3-(Aminomethyl)-6-methyl-4-propyl-2(1H)-pyridinone

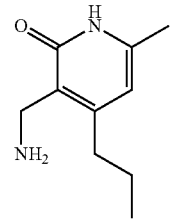

5a) 6-Methyl-2-oxo-4-propyl-1,2-dihydro-3-pyridinecarbonitrile

To a solution of DMSO (300 mL) containing t-BuOK (20 g, 178 mmol) and cyanoacetamide (16.5 g, 196 mmol) was added (3E)-3-hepten-2-one (20 g, 178 mmol), and the contents were stirred at room temperature for 30 min Additional t-BuOK (60 g, 534 mmol) was added and the reaction mixture was placed under an atmosphere of oxygen for an additional 1 h. The reaction mixture was purged with argon, diluted with 4 volumes of H$_2$O, and then 5 volumes of 4 N HCl, which were added slowly. The reaction mixture was filtered, washed with water, and dried to give 6-methyl-2-oxo-4-propyl-1,2-dihydro-3-pyridinecarbonitrile (10 g, 32%). $^1$H NMR (400 MHz, DMSO-d$_6$) δ ppm 12.25-12.40 (br s, 1H), 6.18 (s, 1H), 2.53 (t, 2H), 2.22 (s, 3H), 1.57-1.64 (m, 2H), 0.84 (t, 3H).

5b) 3-(Aminomethyl)-6-methyl-4-propyl-2(1H)-pyridinone

The title compound was prepared in the same manner as described for 3-(aminomethyl)-4-cyclohexyl-6-methyl-2 (1H)-pyridinone (Intermediate 3) using 6-methyl-2-oxo-4-propyl-1,2-dihydro-3-pyridinecarbonitrile (2 g, 11.2 mmol). Obtained: 1.2 g (60%). LCMS E-S (M+H)=181.1. $^1$H NMR (400 MHz, DMSO-d$_6$) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 6

3-(Aminomethyl)-6-methyl-4-phenyl-2(1H)-pyridinone

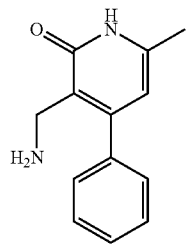 [SMILES: Cc1cc(-c2ccccc2)c(CN)c(=O)[nH]1]

The title compound was prepared in the same manner as described for 3-(aminomethyl)-6-methyl-4-propyl-2(1H)-pyridinone (Intermediate 5) using (3E)-4-phenyl-3-buten-2- one (20 g, 137 mmol). LCMS E-S (M+H)=215.0. ¹H NMR (400 MHz, DMSO-d₆) δ ppm 12.2-12.3 (br s, 1H), 7.88-8.00 (br s, 3H), 7.43-7.51 (m, 3H), 7.29-7.38 (m, 2H), 6.08 (s, 1H), 3.67-3.70 (m, 2H), 2.23 (s, 3H).

Intermediate 7

3-(Aminomethyl)-6-methyl-4-(1-methylethyl)-2(1H)-pyridinone

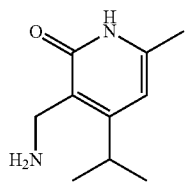

The title compound was prepared in the same manner as described for 3-(aminomethyl)-6-methyl-4-propyl-2(1H)-pyridinone (Intermediate 5) using (3E)-5-methyl-3-hexen-2-one (20 g, 137 mmol). LCMS E-S (M+H)=181.1. ¹H NMR (400 MHz, DMSO-d₆) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 8

3-(Aminomethyl)-4-methyl-6-propyl-2(1H)-pyridinone

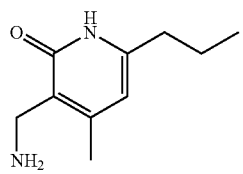

8a) 4-Methyl-2-oxo-6-propyl-1,2-dihydro-3-pyridinecarbonitrile

To a solution of NaNH₂ (32.5 g, 862 mmol) in anhydrous ether (500 mL) at 30° C. was added dropwise a mixture of butyric acid ethyl ester (50 g, 431 mmol) and acetone (37.5 g, 646.5 mol). After addition, the reaction mixture was stirred for 4 h. The reaction mixture was poured onto ice water with stirring. Additional ether was added, and the layers were separated. The aqueous layer was acidified to pH 5.0 with 2 N HCl and then to pH 7.5 with Na₂CO₃. The aqueous layer was then extracted with ether. The combined organic layers were dried over Na₂SO₄, filtered, and concentrated in vacuo. The crude product, 2,4-heptanedione (20 g, 156 mmol), and 2-cyanoacetamide (13.12 g, 156 mmol) were suspended in EtOH (160 mL) at 75° C., followed by addition of piperidine (13.2 g, 156 mmol). The contents were stirred and heated at reflux for 1 h. The mixture was cooled to room temperature and filtered. The collected solid was suspended in water and stirred for 1 h. The mixture was filtered and dried to give 4-methyl-2-oxo-6-propyl-1,2-dihydro-3-pyridinecarbonitrile (11 g, 40%). LCMS E-S (M+H)=181.1. ¹H NMR (400 MHz, DMSO-d₆) δ ppm 12.3-12.4 (br s, 1H), 6.25 (s, 1H), 3.64 (s, 3H), 2.50 (t, 2H), 1.63 (m, 2H), 0.94 (t, 3H).

8b) 3-(Aminomethyl)-4-methyl-6-propyl-2(1H)-pyridinone

Sodium acetate (3.5 g, 42.6 mmol), palladium on carbon (0.81 g) and platinum oxide (0.1 g) were placed in a dried Parr bottle flushed with nitrogen, followed by addition of a small amount of acetic acid (to wet the catalysts). A solution of 4-methyl-2-oxo-6-propyl-1,2-dihydro-pyridine-3-carbonitrile (5 g, 28 mmol) in acetic acid was added to the Parr bottle followed by additional acetic acid (200 mL). The vessel was capped, placed on Parr apparatus and hydrogenated at 45 psi for 12 h. The reaction mixture was filtered and the filtrate concentrated in vacuo. The crude product was purified by preparative HPLC to afford the title compound (TFA salt) as 4.1 g (87%). LCMS E-S (M+H))=181.1. ¹H NMR (400 MHz, DMSO-d₆) δ ppm 11.8-11.9 (br s, 1H), 7.83-7.88 (br s, 3H), 5.99 (s, 1H), 3.77-3.81 (m, 2H), 2.37 (t, 2H), 1.53 (m, 2H), 0.83 (t, 3H).

Intermediate 9

3-(Aminomethyl)-6-cyclopropyl-4-methyl-2(1H)-pyridinone hydrochloride

9a) 1-Cyclopropyl-1,3-butanedione

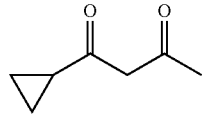

To a stirring solution of THF (100 mL) was added potassium tert-butoxide (5.60 g, 49.5 mmol), followed by a mixture of cyclopropyl methyl ketone (3.27 mL, 33 mmol) and ethyl acetate (9.69 mL, 99 mmol) in 30 mL THF at 35° C., via addition funnel over a 25 min period. The contents were heated and stirred at 60° C. After 3 h, the contents were removed from heating, and allowed to cool to room temperature. The reaction mixture was carefully diluted with 30 mL 2 N HCl and stirred for 10 min The mixture was extracted with diethyl ether (3×50 mL), and the combined organic layers washed with brine (1×50 mL). The organic layer was dried over MgSO₄, filtered, and concentrated in vacuo. Purification by chromatography on silica gel (eluent: 0 to 15% EtOAc in hexanes) with good separation afforded 1-cyclopropyl-1,3-butanedione as a light yellow colored oil, 3.9 g in ~75% purity (residual solvent), for an overall yield of 70%. ¹H NMR (400 MHz, CDCl₃) δ ppm 0.89-0.96 (m, 2H), 1.09-1.15 (m, 2H), 1.59-1.69 (m, 1H), 2.04 (s, 3H), 5.63 (s, 1H), 15.5-16.0 (br s, 1H).

9b) 6-Cyclopropyl-4-methyl-2-oxo-1,2-dihydro-3-pyridinecarbonitrile

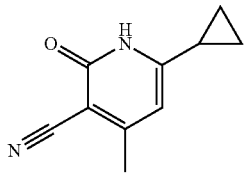

To a stirred solution of ethanol (5 mL) were added 1-cyclopropyl-1,3-butanedione (505 mg, 3.00 mmol) and cyanoacetamide (252 mg, 3.00 mmol), and the heterogenous contents heated until homogenous (ca. 75° C.). Piperidine was added (0.395 mL, 4.00 mmol) and the mixture was heated at reflux for 30 min The reaction mixture was allowed to cool to room temperature, wherein precipitation ensued. The solid precipitate was filtered and set aside. The filtrate was concentrated in vacuo and the oily residue treated with minimal EtOAc and then 10 mL hexanes to afford a second crop of solid. The solid product crops were combined, suspended in water (7 mL), vigorously stirred, and vacuum filtered to afford 6-cyclopropyl-4-methyl-2-oxo-1,2-dihydro-3-pyridinecarbonitrile as a nearly white solid (380 mg, 73%). LCMS E-S (M+H)=175.1. $^1$H NMR (400 MHz, CDCl$_3$) δ ppm 1.01-1.09 (m, 2H), 1.28 (dd, J=8.59, 2.27 Hz, 2H), 1.95-2.01 (m, 1H), 2.43 (s, 3H), 5.82 (s, 1H).

9c) 1,1-Dimethylethyl [(6-cyclopropyl-4-methyl-2-oxo-1,2-dihydro-3-pyridinyl)methyl]carbamate

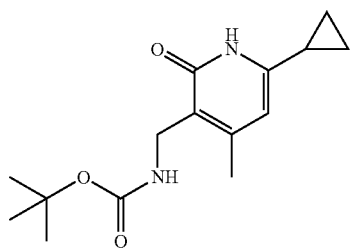 [SMILES: Cc1cc(C2CC2)[nH]c(=O)c1CNC(=O)OC(C)(C)C]

6-Cyclopropyl-4-methyl-2-oxo-1,2-dihydro-3-pyridinecarbonitrile (0.35 g, 2.01 mmol) was added to methanol (20 mL) and the stirred contents cooled to −10° C. Next was added di-tert-butyloxycarbonyl (0.933 mL, 4.02 mmol) and the suspension stirred for 15 min Next was added in NiCl$_2$-6H$_2$O (0.055 g, 0.201 mmol) as a solid and stirred for 5 min Then NaBH$_4$ (0.532 g, 14.06 mmol) was added in 6 portions with 5 min increments between each portion. Then the ice bath was removed and the contents were stirred with warming to room temperature overnight. The reaction mixture was returned to −10° C., followed by addition of 3 more portions of NaBH$_4$ (0.532 g, 14.06 mmol). The ice bath was removed and the mixture stirred at room temperature for 1 h. The contents were quenched by addition of diethylethylene amine (0.218 mL, 2.01 mmol) and stirred for 45 min at room temperature. The volatiles were removed in vacuo and the residue suspended in EtOAc and saturated NaHCO$_3$. The organic layer was washed with additional NaHCO$_3$. The layers were separated, and the organic layer dried over MgSO$_4$, filtered, and concentrated in vacuo. The crude product was purified by silica gel chromatography (eluent: 10% methanol in dichloromethane). The collected product was dried under hi-vacuum for 1 h, and then treated with ether and filtered. After drying in vacuum oven at 45° C. for 2 h, 1,1-dimethylethyl[(6-cyclopropyl-4-methyl-2-oxo-1,2-dihydro-3-pyridinyl)methyl]carbamate was collected (0.28 g, 50%). $^1$H NMR (400 MHz, DMSO-d$_6$) δ ppm 0.73-0.80 (m, 2H), 0.88-0.96 (m, 2H), 1.36 (s, 9H), 1.70-1.82 (m, 1H), 2.11 (s, 3H), 3.95 (d, J=5.31 Hz, 2H), 5.66 (s, 1H), 6.51 (t, J=4.80 Hz, 1H), 11.50 (br. s., 1H).

9d) 3-(Aminomethyl)-6-cyclopropyl-4-methyl-2(1H)-pyridinone hydrochloride 1,1-Dimethylethyl[(6-cyclopropyl-4-methyl-2-oxo-1,2-dihydro-3-pyridinyl)methyl]carbamate (0.28 g, 1.006 mmol) was added to EtOAc (9 mL) and methanol (1.0 mL). The suspension was stirred at room temperature for 5 min, followed by addition of 4 M HCl in dioxane (5.03 mL, 20.12 mmol), and the contents were stirred at room temperature overnight. The volatiles were then removed in vacuo to afford a solid. The solid was triturated with ether, filtered, and dried in a vacuum oven at 45° C. for 4 h. The title compound was collected (0.22 g, 100% yield). $^1$H NMR (400 MHz, DMSO-d$_6$) δ ppm 0.78-0.86 (m, 2H), 0.95-1.03 (m, 2H), 1.83 (tt, J=8.46, 5.05 Hz, 1H), 2.16-2.22 (m, 3H), 3.75 (q, J=5.47 Hz, 2H), 5.79 (s, 1H), 8.02 (br. s., 3H), 11.92 (br. s., 1H).

Intermediate 10

3-(Aminomethyl)-4-ethyl-6-methyl-2(1H)-pyridinone hydrochloride

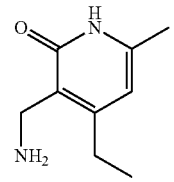

10a) Hex-3-en-2-one

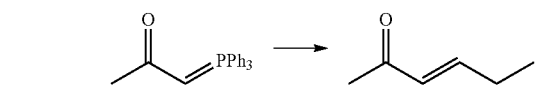

To a stirred solution of 1-(triphenylphosphoranylidene)-2-propanone (100 g, 307 mmol) in DCM (500 mL) was added propionaldehyde (140 mL, 1929 mmol) at room temperature. The reaction mixture was then stirred at room temperature for 18 hours. The reaction was monitored by TLC. The solvent (DCM) was distilled off using ordinary distillation. The residue was then distilled using fractional distillation under vacuum (~450 mbar) and the desired product was isolated. The title compound, hex-3-en-2-one (20 g, 66%), was collected at 110° C. $^1$H NMR (CDCl$_3$, 400 MHz) δ ppm 1.071-1.121 (t, 3H, J=7.4 Hz), 2.250-2.299 (m, 5H), 6.054-6.094 (d, 1H, J=16 Hz), 6.823-6.895 (m, 1H).

10b) 4-Ethyl-1,2-dihydro-6-methyl-2-oxopyridine-3-carbonitrile

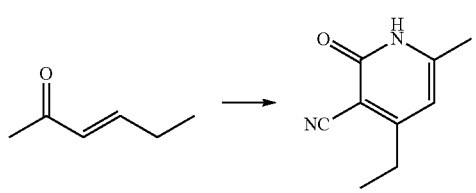

To a stirred solution of t-BuOK (22.85 g, 204.08 mmol) and cyanoacetamide (18.8 g, 224.1 mmol) in DMSO (300 mL) was added hex-3-en-2-one (20 g, 204.08 mmol) under argon atmosphere at room temperature. The reaction mixture was then stirred at room temperature for 30 min and then added additional t-BuOK (68.5 g, 612.05 mmol) was added. Argon gas was displaced by oxygen gas and the mixture stirred for 48 hrs at room temperature in presence of oxygen. Reaction was monitored by TLC. The reaction mixture was cooled to 0° C. and diluted with water (100 mL) followed by 4 N HCl (120 mL). The mixture was stirred for 15 min and the resulting solid was filtered. The solid was washed with water (1 L) and dried to afford the title compound, 4-ethyl-1,2-dihydro-6-methyl-2-oxopyridine-3-carbonitrile (10.5 g, 31%), as an off white solid. $^1$H NMR (CDCl$_3$, 400 MHz): 6 ppm 1.148-1.185 (t, 3H, J=7.4 Hz), 2.237 (s, 3H), 2.557-2.614 (m, 2H), 6.211 (s, 1H), 12.330 (broad s, 1H). MS (ES) [M+H]$^+$ 161.06.

10c) 3-(Amino methyl)-4-ethyl-6-methylpyridin-2(1H)-one

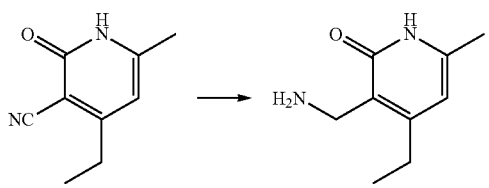

To a suspension of Raney Nickel (6 g) in methanol (200 mL) was added 4-ethyl-1,2-dihydro-6-methyl-2-oxopyridine-3-carbonitrile (10 g, 61.7 mmol) and methanolic ammonia (750 mL). The reaction mixture was stirred at room temperature under hydrogen pressure (80 psi) for 48 hrs. The reaction mixture was filtered through Celite and washed with methanol (250 mL). The filtrate was concentrated under reduced pressure and the residue purified by filter column using silica gel (60-120 mesh), eluted with 10% MeOH in CHCl$_3$, to afford 3-(amino methyl)-4-ethyl-6-methylpyridin-2(1H)-one (5.6 g, 54%) as an off white solid. $^1$H NMR (DMSO-D$_6$, 400 MHz) (free amine): 6 ppm 1.063-1.101 (t, 3H, J=7.6 Hz), 2.101 (s, 3H), 2.412-2.449 (m, 2H), 3.448 (s, 2H), 5.835 (s, 1H). MS (ES) [M+H]$^+$ 167.06.

10d) 3-(Aminomethyl)-4-ethyl-6-methylpyridin-2(1H)-one hydrochloride

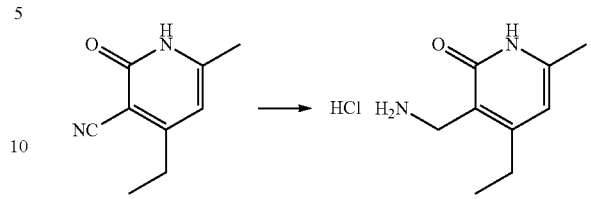

3-(Amino methyl)-4-ethyl-6-methylpyridin-2(1H)-one, (5.6 g, 33 mmol) was suspended in DCM (560 mL) and the insoluble contents/particles were filtered. The filtrate was concentrated and dried. The residue was dissolved in DCM (10 mL) and 4 M HCl in 1,4-dioxane (16 mL, 66 mmol) was added at 0° C. and stirred for 10 min, at which time the reaction mixture was concentrated under high-vacuum and dried. The resulting crude solid was triturated with hexane (150 mL) and filtered. The solid was dried under vacuum. Collected 3-(amino methyl)-4-ethyl-6-methylpyridin-2(1H)-one hydrochloride (5.9 g, 86%). $^1$H NMR (400 MHz, DMSO-d$_6$) δ ppm 1.082-1.120 (t, 3H, J=7.6 Hz), 2.179 (s, 3H), 2.503-2.544 (m, 2H), 3.785-3.798 (d, 2H, J=5.2 Hz), 6.024 (s, 1H), 7.985 (broad s, 2H), 11.858 (broad s, 1H). MS (ES) [M+H]$^+$ 167.2.

Intermediate 11

3-(aminomethyl)-6-ethyl-4-methyl-2(1H)-pyridinone

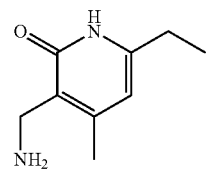

11a) 4-ethyl-6-methyl-2-oxo-1,2-dihydro-3-pyridinecarbonitrile

To a solution of t-BuOK (17.2 g, 153 mmol) and cyanoacetamide (13 g, 153 mmol) in CH$_3$CN (225 mL) was added (3E)-3-hexen-2-one (15 g, 153 mmol) at room temperature under N$_2$ atmosphere. The reaction mixture was stirred for 30 min To the reaction mixture was added additional t-BuOK (51.4 g), and the N$_2$ was displaced by oxygen. After stirring for 1 h without external cooling, the mixture was diluted with 4 N HCl, which was added slowly and with good stirring. The mixture was filtered, washed with EtOH, dried to give 6-ethyl-4-methyl-2-oxo-1,2-dihydro-3-pyridinecarbonitrile (5 g, 21%). $^1$H NMR (400 MHz, DMSO-d$_6$) δ 12.33 (br. s., 1H), 6.18 (s, 1H), 2.45 (q, 2H), 2.30 (s, 3H), 1.11 (t, 3H).

11b) 3-(aminomethyl)-6-ethyl-4-methyl-2(1H)-pyridinone

To an ice bath cooled THF solution (200 mL) of 6-ethyl-4-methyl-2-oxo-1,2-dihydro-3-pyridinecarbonitrile (7 g, 43.2 mmol) was added NaBH$_4$ (4.2 g, 108 mmol), and I$_2$ (11.2 g, 43.2 mmol), and the contents were stirred for 30 min The reaction mixture was then heated at reflux overnight. The reaction mixture was cooled, and carefully neutralized by slow addition of 4 N HCl at 0° C. The mixture was dried over MgSO₄, filtered, and concentrated in vacuo. The product was purified by HPLC to give 3-(aminomethyl)-6-ethyl-4-methyl-2(1H)-pyridinone as a TFA salt (1.9 g 26.4%). LCMS MH+=167.1 ¹H NMR (400 MHz, DMSO-d₆) δ 11.82 (br. s., 1H), 7.82 (br s, 3H), 5.97 (s, 1H), 3.75-3.77 (m, 2H), 2.39 (q, 2H), 2.17 (s, 3H), 1.09 (t, 3H).

Intermediate 12

3-(aminomethyl)-6-methyl-4,4'-bipyridin-2(1H)-one

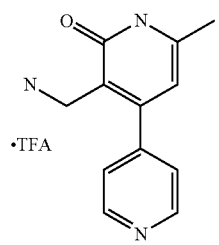 [SMILES: Cc1cc(-c2ccncc2)c(CN)c(=O)[nH]1]

12a) (2Z)-3-hydroxy-1-(4-pyridinyl)-2-buten-1-one

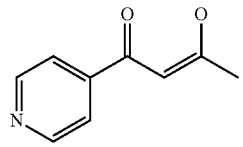

To a solution of ethyl 4-pyridinecarboxylate (30 g, 198 mmol) and acetone (34.58 g, 595 mmol) in THF (150 mL) was slowly added NaOMe (12.87 g, 238 mmol) at 35-40° C. The mixture was stirred at room temperature for 0.5 h, and then heated at reflux for 3 h. The mixture was cooled to room temperature and filtered to give a solid, which was washed with t-BuOMe, and dissolved in H₂O. The solution was acidified with acetic acid and the resulting oily product was extracted with CHCl₃. The solvent was removed in vacuo, and the crude product was obtained (12 g, 37%) and used without further purification. ¹H NMR (400 MHz, DMSO-d₆) δ 8.73 (d, 2H), 7.76 (d, 2H), 6.63 (s, 1H), 2.21 (s, 3H); note: enolic OH does not appear.

12b) 6-methyl-2-oxo-1,2-dihydro-4,4'-bipyridine-3-carbonitrile and 4-methyl-6-oxo-1,6-dihydro-2,4'-bipyridine-5-carbonitrile

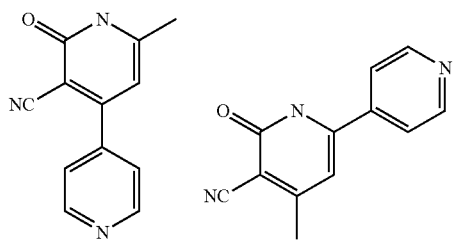 [SMILES: Cc1cc(-c2ccncc2)c(C#N)c(=O)[nH]1 ; Cc1cc(-c2ccncc2)[nH]c(=O)c1C#N]

To a solution of (2Z)-3-hydroxy-1-(4-pyridinyl)-2-buten-1-one (8 g, crude, 49 mmol) and cyanoacetamide (4.12 g, 49 mmol) in anhydrous EtOH (100 mL) was added piperidine (4.17 g, 49 mmol) under N₂ at 75° C. The mixture was heated at reflux for 1 h, and then cooled to room temperature. After filtration, the solid was collected and washed with H₂O to give the crude product (4 g) as two isomers. After separation by HPLC, 1.8 g of 6-methyl-2-oxo-1,2-dihydro-4,4'-bipyridine-3-carbonitrile and 1.2 g of 4-methyl-6-oxo-1,6-dihydro-2,4'-bipyridine-5-carbonitrile were obtained. The identity of 6-methyl-2-oxo-1,2-dihydro-4,4'-bipyridine-3-carbonitrile was established by nOE analysis. ¹H NMR (400 MHz, DMSO-d₆) δ 12.79 (br. s., 1H), 8.75 (d, 2H), 7.58 (d, 2H), 6.37 (s, 1H), 2.31 (s, 3H).

12c) 3-(aminomethyl)-6-methyl-4,4'-bipyridin-2(1H)-one

To an ice bath cooled THF (100 mL) solution of 6-methyl-2-oxo-1,2-dihydro-4,4'-bipyridine-3-carbonitrile (4 g, 18.9 mmol) was added NaBH₄ (1.43 g, 37.9 mmol), and I₂ (4.81 g, 18.9 mmol), and the mixture was stirred for 0.5 h. The reaction mixture was then heated at reflux for 4 h. After cooling to 0° C., the reaction mixture was adjusted to pH 5 with 4 N HCl. The mixture was concentrated in vacuo to give the crude compound, which was purified by HPLC to give 3-(aminomethyl)-6-methyl-4,4'-bipyridin-2(1H)-one (1.9 g, 31%) as a TFA salt. LCMS MH+=216.0 ¹H NMR (400 MHz, DMSO-d₆ in D₂O) δ 8.87 (d, 2H), 7.87 (d, 2H), 6.13 (s, 1H), 3.65 (br s, 2H), 2.17 (s, 3H).

Intermediate 13

3-(aminomethyl)-6-cyclobutyl-4-methyl-2(1H)-pyridinone

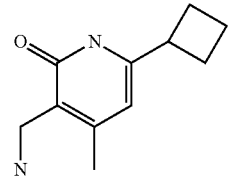

13a) Ethyl cyclobutanecarboxylate

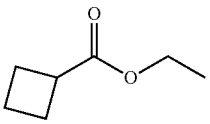

To a solution of cyclobutanecarboxylic acid (50 g, 500 mmol) in EtOH (1.2 L) was slowly added H₂SO₄ (20 mL) at room temperature. The solution was stirred at reflux overnight, and then cooled and poured into H₂O. The aqueous layer was extracted with ether. The combined organic layers were washed with brine, dried over Na₂SO₄, and concentrated in vacuo to give ethyl cyclobutanecarboxylate as a colorless oil (44 g, 69%). ¹H NMR (400 MHz, CDCl₃-d₃) δ 4.04 (q, 2H), 3.04 (m, 1H), 2.12 (m, 4H), 1.88 (m, 2H), 1.18 (t, 3H).

13b) 1-cyclobutyl-1,3-butanedione

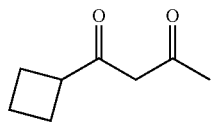

To a solution of NaNH₂ (11.7 g, 91 mmol) in anhydrous ether (150 mL) under N₂ at 30° C. was added dropwise a mixture of ethyl cyclobutanecarboxylate (19.2 g, 150 mmol) and acetone (21.75 g, 375 mmol). After addition, the reaction mixture was stirred for 4 h, then poured onto ice water with stirring. Ether was added and the unreacted components were extracted into the organic phase. The clear aqueous extract was acidified to pH 5.0 with 2 N HCl, and then to pH 7.5 with Na₂CO₃. The solution was extracted with ether. The combined organic layers were dried (Na₂SO₄), filtered, and concentrated to give the crude product of 1-cyclobutyl-1,3-butanedione (9.7 g, 76%), which was used in the next step without further purification. $^1$H NMR (400 MHz, CDCl$_3$-d$_3$) δ 5.42 (s, 1H), 3.66 (s, 1H), 2.11-2.23 (m, 4H), 2.02 (s, 3H), 1.93-1.99 (m, 2H).

13c) 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile

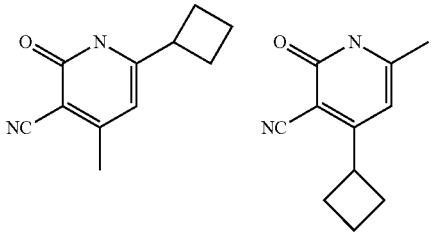

To a solution of 1-cyclobutyl-1,3-butanedione (1.5 g, 10.7 mmol) and cyanoacetamide (1.07 g, 12.8 mmol) in EtOH (25 mL) was added piperidine (1.08 g, 12.8 mmol) at 75° C. After addition, the mixture was stirred with warming to reflux. After 1 h, the mixture was cooled to room temperature during which time precipitation occurred. The contents were filtered, and the filtered solid suspended in water and stirred for 1 h. The heterogenous mixture was filtered and dried to give a mixture of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (1.14 g, 57%). $^1$H NMR (400 MHz, DMSO-d$_6$ in D$_2$O) δ 12.15-12.30 (br s, 2H), 6.39 (s, 1H), 6.34 (s, 1H), 2.40-2.28 (m, 7H), 2.23-2.25 (m, 3H), 2.18-2.21 (m, 4H), 1.99-2.11 (m, 2H), 1.84-1.90 (m, 2H).

13d) 3-(aminomethyl)-6-cyclobutyl-4-methyl-2(1H)-pyridinone and 3-(aminomethyl)-4-cyclobutyl-6-methyl-2(1H)-pyridinone

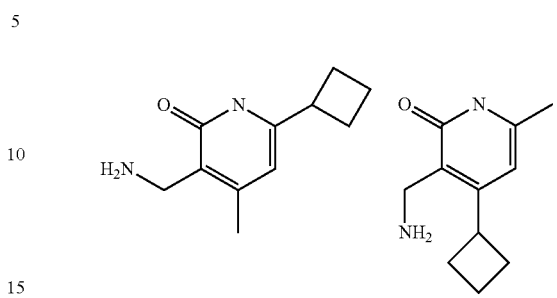

To an ice bath cooled THF (100 mL) solution of 6-cyclobutyl-4-methyl-2-oxo-1,2-dihydro-3-pyridinecarbonitrile and 4-cyclobutyl-6-methyl-2-oxo-1,2-dihydro-3-pyridinecarbonitrile (6 g, 32 mmol) was added NaBH$_4$ (2.73 g, 71.8 mmol), and I$_2$ (8.3 g, 32 mmol), and the mixture was stirred for 30 min The reaction mixture was then heated at reflux for 3 h. After cooling to 0° C., the reaction mixture was adjusted to pH 5 with 6 N HCl. The contents were dried, filtered, and concentrated in vacuo. The crude product was purified by HPLC to give a mixture of 3-(aminomethyl)-6-cyclobutyl-4-methyl-2(1H)-pyridinone and 3-(aminomethyl)-4-cyclobutyl-6-methyl-2(1H)-pyridinone (5.6 g, 91%). $^1$H NMR (400 MHz, DMSO-d$_6$) δ 11.60-11.70 (br s, 2H), 7.85 (br s, 4H), 6.15 (s, 1H), 6.03 (s, 1H), 3.72-3.79 (m, 2H), 3.29-3.33 (m, 2H), 2.16 (s, 6H), 2.05-2.10 (m, 6H), 1.88-1.93 (m, 4H), 1.69-1.79 (m, 4H).

13e) 1,1-dimethylethyl [(6-cyclobutyl-4-methyl-2-oxo-1,2-dihydro-3-pyridinyl)methyl]carbamate and 1,1-dimethylethyl [(4-cyclobutyl-6-methyl-2-oxo-1,2-dihydro-3-pyridinyl)methyl]carbamate

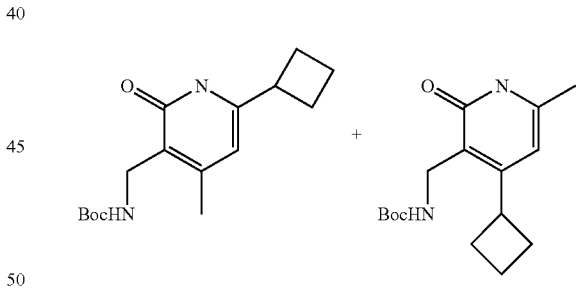

To an ice bath cooled solution of 3-(aminomethyl)-6-cyclobutyl-4-methyl-2(1H)-pyridinone and 3-(aminomethyl)-4-cyclobutyl-6-methyl-2(1H)-pyridinone (3.5 g, 18 mmol) in THF (10 mL) and DMF (10 mL) were added Boc$_2$O (4.68 g, 21.8 mmol) and triethylamine (5.4 g, 54 mmol). The contents were then stirred for 30 min at 30° C. The reaction was quenched by addition of ice water, during which time precipitation occurred. The reaction mixture was filtered and dried to give a mixture of the crude products. The crude products were separated by HPLC to give 1,1-dimethylethyl [(6-cyclobutyl-4-methyl-2-oxo-1,2-dihydro-3-pyridinyl)methyl]carbamate (2.1 g, 20%) and 1,1-dimethylethyl [(4-cyclobutyl-6-methyl-2-oxo-1,2-dihydro-3-pyridinyl)methyl]carbamate (1 g, 9.5%). Data for 1,1-dimethylethyl [(6-cyclobutyl-4-methyl-2-oxo-1,2-dihydro-3-pyridinyl)methyl]carbamate: $^1$H NMR (400 MHz, DMSO-d$_6$) δ 11.28 (br s, 1H), 6.49 (br s, 1H), 5.86

(br s, 1H), 3.85 (br s, 2H), 1.97-2.14 (m, 7H), 1.87-1.94 (m, 1H), 1.72-1.77 (m, 1H), 1.28 (s, 9H).

13f) 3-(aminomethyl)-6-cyclobutyl-4-methyl-2(1H)-pyridinone hydrochloride

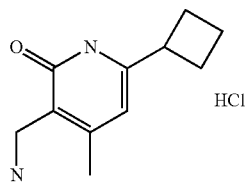

A solution of 1,1-dimethylethyl [(6-cyclobutyl-4-methyl-2-oxo-1,2-dihydro-3pyridinyl)methyl]carbamate (2.1 g, 7.2 mmol) in 4 N HCl (in 15 mL 1,4 dioxane) was heated to 60° C. for 1 h. The mixture was cooled to room temperature. The mixture was filtered and dried to give 3-(aminomethyl)-6-cyclobutyl-4-methyl-2(1H)-pyridinone as an HCl salt (1.95 g, 90%). LCMS MH+=193.1 $^1$H NMR (400 MHz, DMSO-$d_6$) δ 11.70 (br s, 1H), 8.01 (s, 3H), 6.04 (s, 1H), 3.74 (d, 2H), 3.32-3.39 (m, 1H), 2.22 (s, 3H), 2.17-2.20 (m, 2H), 2.06-2.11 (m, 2H), 1.85-1.95 (m, 1H), 1.71-1.79 (m, 1H).

Intermediate 14

3-(aminomethyl)-6-methyl-4-[(methyloxy)methyl]-2 (1H)-pyridinone

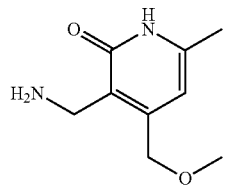

14a) 1-(methyloxy)-2,4-pentanedione

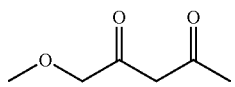

To a solution of sodium (5.83 g, 243.3 mmol) in dry toluene (62.5 mL) was added ethyl (methyloxy)acetate (24 g, 203.4 mmol) at −5° C. After stirring for 3 h, acetone (14 g, 231.4 mmol) was slowly added, upon which the mixture became brown and viscous. Next added 72 mL of tert-butyl methyl ether, and the reaction mixture was stirred at room temperature for 12 h, after which time the sodium salt precipitated. After collection and washing with additional tert-butyl methyl ether, the sodium salt was dissolved in 46 mL of 20% $H_2SO_4$. The contents were extracted with tert-butyl methyl ether and the organic layers concentrated to afford 1-(methyloxy)-2,4-pentanedione (9.76 g, 36.9%). $^1$H NMR (400 MHz, CDCl$_3$-$d_3$) δ 5.76 (s, 1H), 3.96 (s, 2H), 3.38 (s, 3H), 2.07 (s, 3H).

14b) 6-methyl-4-[(methyloxy)methyl]-2-oxo-1,2-dihydro-3-pyridinecarbonitrile

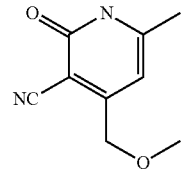

1-(methyloxy)-2,4-pentanedione (9.51 g, 73.12 mmol) and cyanoacetamide (6.17 g, 73.12 mmol) were dissolved in EtOH (76 mL) and heated until homogenous (ca. 75° C.). Piperidine (6.25 g, 73.12 mmol) was added and the reaction mixture heated at reflux for 20 mins, followed by cooling to room temperature. The contents were filtered to give a solid which was suspended in 140 mL water and stirred vigorously for 20 min The heterogenous mixture was filtered to afford 6-methyl-4-[(methyloxy)methyl]-2-oxo-1,2-dihydro-3-pyridinecarbonitrile (7.8 g, 65.6%). LCMS MH+=179.0 $^1$H NMR (400 MHz, DMSO-$d_6$) δ 12.47 (br s, 1H), 6.26 (s, 1H), 4.40 (s, 2H), 3.29 (s, 3H), 2.25 (s, 3H).

14c) 3-(aminomethyl)-6-methyl-4-[(methyloxy)methyl]-2(1H)-pyridinone 6-methyl-4-[(methyloxy)methyl]-2-oxo-1,2-dihydro-3-pyridinecarbonitrile (1.000 g, 5.61 mmol) was suspended in acetic acid (150 ml) and the solution passed through an H-cube instrument equipped with Raney-Ni cartridge at a rate of 1 mL/min at 50 psi and 60° C. After 18 h. the acetic acid was removed under reduced pressure and the remaining residue was dissolved in MeOH. The methanolic solution was passed through a 0.2 µm teflon syringe filter. The methanolic filtrate was purified by reverse phase HPLC (Gemini 50×100 5 µm column. Run 1: 3 min, 90-10%. Run 2, 5 min 0-10%. Run 3, 10 min, 0-20%. The product fractions were concentrated to dryness on a Genevac HT-4 instrument to afford 3-(aminomethyl)-6-methyl-4-[(methyloxy)methyl]-2(1H)-pyridinone as a pale grey waxy solid (900 mg, 70.2% yield) LCMS MH+=183.0 $^1$H NMR (400 MHz, DMSO-$d_6$) δ 8.40 (br. s., 1H), 6.10 (s, 1H), 4.39 (s, 2H), 3.66 (br. s., 2H), 3.32 (s, 3H), 2.19 (s, 3H).

Intermediate 15

3-(aminomethyl)-6-methyl-4-(phenylmethyl)-2(1H)-pyridinone and 3-(aminomethyl)-4-methyl-6-(phenylmethyl)-2(1H)-pyridinone

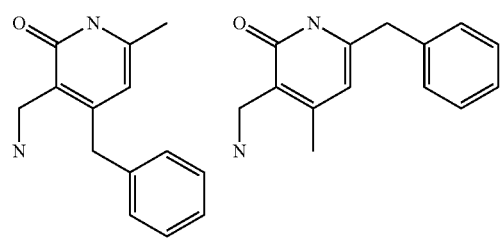

15a) 1-phenyl-2,4-pentanedione

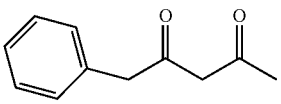

To a solution of NaNH$_2$ (19.02 g, 480 mmol) in anhydrous ether (400 mL) under N$_2$ at −5° C. was added dropwise ethyl phenylacetate (19.2 g, 150 mmol) and then acetone (21.23 g, 370 mmol) with vigorous stirring. After addition, the reaction mixture was stirred at room temperature overnight. The mixture was then acidified to pH 4.0-5.0 with 1 N HCl. The organic layer was separated and concentrated in vacuo. The crude product was purified by silica gel chromatography to give 1-phenyl-2,4-pentanedione (18.32 g, 44%). $^1$H NMR (400 MHz, CDCl$_3$-d$_3$) δ 15.49 (br s, 1H), 7.33-7.45 (m, 5H), 5.53 (s, 1H), 3.66 (s, 2H), 2.10 (s, 3H).

15b) 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile

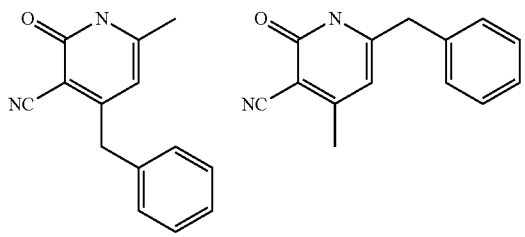 [SMILES: Cc1cc(Cc2ccccc2)c(C#N)c(=O)[nH]1 ; Cc1cc(Cc2ccccc2)[nH]c(=O)c1C#N]

1-phenyl-2,4-pentanedione (18.32 g, 104 mmol) and cyanoacetamide (8.74 g, 104 mmol) were dissolved in EtOH (104 mL) and heated until homogenous (ca. 75° C.). Piperidine (8.86 g, 104 mmol) was added and the reaction mixture heated at reflux for 15-30 min followed by cooling to room temperature, during which time precipitation occurred. The heterogenous contents were filtered to give a solid which was suspended in 200 mL water and stirred vigorously for 20 min The heterogenous mixture was filtered to afford 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (12.06 g, 52%). LCMS MH+=225.1 $^1$H NMR (400 MHz, DMSO-d$_6$) (mixture of compounds) δ 7.21-7.31 (m, 10H), 6.06 (s, 2H), 3.89 (s, 2H), 3.79 (s, 2H), 2.24 (s, 3H), 2.15 (s, 3H).

15c) 3-(aminomethyl)-6-methyl-4-(phenylmethyl)-2(1H)-pyridinone and 3-(aminomethyl)-4-methyl-6-(phenylmethyl)-2(1H)-pyridinone

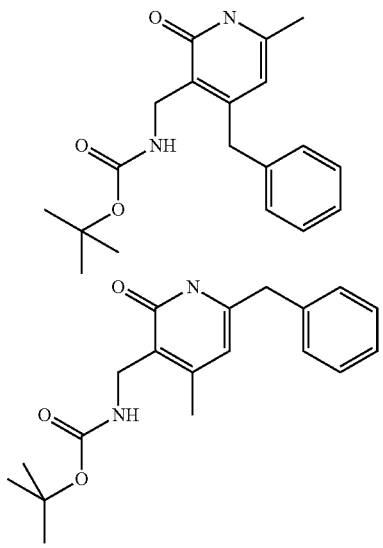

Sodium acetate (6.14 g, 74.8 mmol), Pd/C (0.65 g, 1 mmol), and platinum (II) oxide (45 mg, 1 mmol) were placed in a dried Parr bottle equipped with nitrogen inlet. A small amount of acetic acid was added to wet the catalysts. A solution of 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (6 g, 26.7 mmol) in acetic acid (300 mL) was added to the vessel. The contents were sealed and hydrogenated on Parr shaker at 45 psi for 12 h. The reaction mixture was filtered and washed with acetic acid. The filtrate was removed under reduced pressure. The residue was washed with methanol and filtered to afford a crude mixture of 3-(aminomethyl)-6-methyl-4-(phenylmethyl)-2(1H)-pyridinone and 3-(aminomethyl)-4-methyl-6-(phenylmethyl)-2(1H)-pyridinone. The reaction was run in duplicate to afford a total crude recovery of 14.5 g. To a solution of the above crude product mixture (4.0 g, 17.5 mmol) in THF (10 mL) and DMF (10 mL) was added di-tert-butoxycarbonyl anhydride (5.0 g, 23.4 mmoL) and triethylamine (5.2 g, 52.5 mmol) at 0° C. The reaction mixture stirred with warming to room temperature and then stirred for an additional 4 h. The contents were diluted with ice water and then filtered. The collected solid was dried and the products separated by HPLC to furnish 1.2 g of 1,1-dimethylethyl {[4-methyl-2-oxo-6-(phenylmethyl)-1,2-dihydro-3-pyridinyl]methyl}carbamate ($^1$H NMR (400 MHz, DMSO-d$_6$) δ 11.55-1.60 (br s, 1H), 7.20-7.29 (m, 5H), 5.85 (s, 1H), 3.92 (s, 2H), 3.90 (s, 2H), 2.10 (s, 3H), 1.32 (s, 9H) and 1.0 g of 1,1-dimethylethyl {[6-methyl-2-oxo-4-(phenylmethyl)-1,2-dihydro-3-pyridinyl]methyl}carbamate ($^1$H NMR (400 MHz, DMSO-d$_6$) δ 11.50-11.55 (br s, 1H), 7.18-7.25 (m, 5H), 5.75 (s, 1H), 4.02 (s, 2H), 3.85 (s, 2H), 2.05 (s, 3H), 1.32 (s, 9H).

15d) 3-(aminomethyl)-4-methyl-6-(phenylmethyl)-2 (1H)-pyridinone hydrochloride

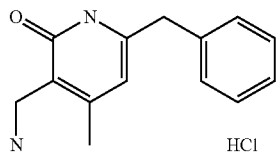 [SMILES: Cc1cc(Cc2ccccc2)[nH]c(=O)c1CN ; Cl]

A solution of 1,1-dimethylethyl {[4-methyl-2-oxo-6-(phenylmethyl)-1,2-dihydro-3-pyridinyl]methyl}carbamate (1.2 g, 3.66 mmol) in 4N HCl (in 15 mL 1,4 dioxane) was heated to 60° C. for 1 h. The mixture was cooled to room temperature. The mixture was filtered and dried to give 3-(aminomethyl)-4-methyl-6-(phenylmethyl)-2(1H)-pyridinone as an HCl salt (0.725 g, 87%). LCMS MH+=229.1 $^1$H NMR (400 MHz, DMSO-$d_6$) δ 11.9-12.0 (br s, 1H), 7.99 (br s, 3H), 7.20 (s, 5H), 5.97 (s, 1H), 3.72-3.75 (m, 4H), 2.17 (s, 3H).

15e) 3-(aminomethyl)-6-methyl-4-(phenylmethyl)-2 (1H)-pyridinone hydrochloride

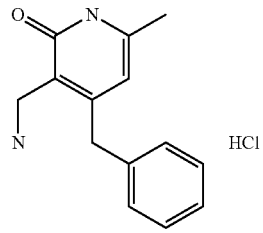 [SMILES: Cc1cc(Cc2ccccc2)c(CN)c(=O)[nH]1 ; Cl]

A solution of 1,1-dimethylethyl {[6-methyl-2-oxo-4-(phenylmethyl)-1,2-dihydro-3-pyridinyl]methyl}carbamate (1.0 g, 3.0 mmol) in 4N HCl (in 15 mL 1,4 dioxane) was heated to 60° C. for 1 h. The mixture was cooled to room temperature. The mixture was filtered and dried to give 3-(aminomethyl)-6-methyl-4-(phenylmethyl)-2(1H)-pyridinone as an HCl salt (0.600 g, 86%). LCMS MH+=229.1 $^1$H NMR (400 MHz, DMSO-$d_6$) δ 11.9-12.0 (br s, 1H), 8.03 (br s, 3H), 7.16-7.30 (m, 5H), 5.84 (s, 1H), 3.91 (s, 2H), 3.81 (s, 2H), 2.10 (s, 3H).

Intermediate 16

3-(aminomethyl)-6-methyl-4-(4-morpholinylmethyl)-2(1H)-pyridinone

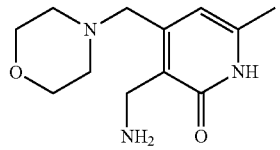 [SMILES: Cc1cc(CN2CCOCC2)c(CN)c(=O)[nH]1]

a) 5-(4-morpholinyl)-3-pentyn-2-one

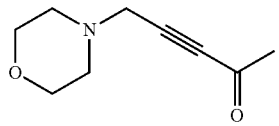

To a cooled (−40° C., CH$_3$CN/CO$_2$) solution of 4-(2-propyn-1-yl)morpholine (2.2 g, 17.58 mmol) in THF (5 mL) was added dropwise via. syringe under N$_2$ a solution of 2 M isopropylmagnesium chloride in THF (10 mL, 20.00 mmol). The reaction was stirred for 1 hr then a solution of N-methoxy-N-methylacetamide (2.2 mL, 20.69 mmol) in THF (5 mL) was added in one portion. The reaction was stirred for 2 hr (allowed to slowly warm to RT), quenched with aq. NH$_4$Cl, extracted with EtOAc, washed with brine, dried (Na$_2$SO$_4$), filtered and evaporated to dryness under vacuum. The residue was purified by silica gel chromatography (Analogix, SF25-60 g, 0 to 80% EtOAc in hexanes). The pure fractions were combined and evaporated to dryness to give the product 5-(4-morpholinyl)-3-pentyn-2-one (2.09 g, 12.50 mmol, 71.1% yield) as a yellow oil. $^1$H NMR (400 MHz, DMSO-$d_6$) δ 3.62-3.57 (m, 4H), 3.56 (s, 2H), 2.49-2.43 (m, 4H), 2.34 (s, 3H). MS (ES)+ m/e 168.0 [M+H]$^+$.

b) 6-methyl-4-(4-morpholinylmethyl)-2-oxo-1,2-dihydro-3-pyridinecarbonitrile

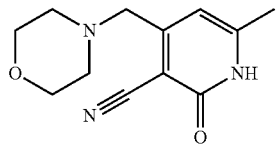 [SMILES: Cc1cc(CN2CCOCC2)c(C#N)c(=O)[nH]1]

To a stirred solution of 21 wt % sodium ethoxide in EtOH (4.2 g, 12.96 mmol) in EtOH (30 mL) was added 2-cyanoacetamide (1.1 g, 13.08 mmol). The reaction was stirred for 15 min then a solution of 5-(4-morpholinyl)-3-pentyn-2-one (2.0 g, 11.96 mmol) in EtOH was added to the reaction in one portion. (The reaction quickly turned dark red.) The reaction was stirred overnight at RT, neutralized with 6 N HCl (2.17 mL, 13.02 mmol) and evaporated to dryness under vacuum. Dried under vacuum overnight. The remaining dark solid was triturated with a solution of (9:1) CH$_2$Cl$_2$, MeOH (50 mL), filtered from insoluble material, washed with (9:1) CH$_2$Cl$_2$, MeOH, and the filtrate evaporated to dryness under vacuum. The dark solid was triturated with a solution of (1:1) EtOAc in hexanes, filtered, washed with (1:1) EtOAc in hexanes, and dried under vacuum to give a brown solid (removed a lot of fast running non-polar impurities). The crude product was purified by silica gel chromatography (Analogix, SF25-60 g, 0 to 15% CH$_2$Cl$_2$/20% (5% NH$_4$OH in MeOH) in CH$_2$Cl$_2$). The pure fractions were combined, evaporated to dryness, triturated with hexanes and dried under vacuum to give the product 6-methyl-4-(4-morpholinylmethyl)-2-oxo-1,2-dihydro-3-pyridinecarbonitrile (0.90 g, 3.86 mmol, 32.3% yield) as a light tan solid.

$^1$H NMR (400 MHz, DMSO-$d_6$) δ 12.44 (br. s., 1H), 6.34 (s, 1H), 3.63-3.56 (m, 4H), 3.48 (s, 2H), 2.45-2.36 (m, 4H), 2.27 (s, 3H)

MS (ES)+ m/e 234.1 [M+H]$^+$.

c) 3-(aminomethyl)-6-methyl-4-(4-morpholinylmethyl)-2(1H)-pyridinone

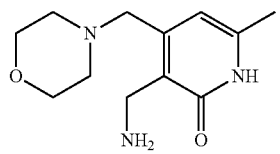 [SMILES: Cc1cc(CN2CCOCC2)c(CN)c(=O)[nH]1]

A clear solution of 6-methyl-4-(4-morpholinylmethyl)-2-oxo-1,2-dihydro-3-pyridinecarbonitrile (0.60 g, 2.57 mmol) in HOAc (20 mL) was treated on an H-Cube apparatus (50 psi, 60° C., 1 mL/min, Raney Nickel cartridge) for 18 hr overnight. LCMS showed that the reaction was complete. The reaction was evaporated to dryness, taken up in a small volume of MeOH and treated with 4 N HCl in dioxane (5 mL, 20.00 mmol). The mixture was evaporated to dryness under vacuum (began to ppt. out during evaporation), triturated with Et2O, filtered and dried under vacuum to give the product 3-(aminomethyl)-6-methyl-4-(4-morpholinylmethyl)-2(1H)-pyridinone (0.76 g, 2.450 mmol, 95% yield) as a light grey solid. $^1$H NMR (400 MHz, DMSO-$d_6$) δ 6.39 (s, 1H), 4.28 (s, 2H), 3.99 (s, 2H), 3.87 (br. s., 4H), 3.27 (br. s., 4H), 2.22 (s, 3H). MS (ES)+ m/e 238.0 [M+H]$^+$ (weak), 221.3 [M+H]$^+$—NH$_3$ (strong).

Intermediate 17 tert-Butyl (5-(aminomethyl)-6-methoxy-4-methylpyridin-2-yl)carbamate

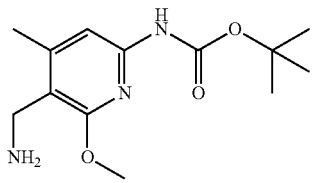 [SMILES: COc1nc(NC(=O)OC(C)(C)C)cc(C)c1CN]

a) Ethyl 4-ethoxy-2-oxopent-3-enoate

To a stirred solution of ethyl 2,4-dioxopentanoate (36.5 g, 231 mmol) and triethyl orthoformate (41 mL, 246 mmol) in ethanol (60 mL) was added ammonium chloride (3.7 g, 69 mmol). The suspension was stirred at RT overnight. LCMS showed that the reaction was mostly complete. (Hydrolyzes on LCMS to some degree?) The reaction was concentrated under vacuum. The remaining oil was taken up in Et$_2$O (300 mL), filtered to remove insolubles, rinsed with Et$_2$O, and concentrated under vacuum. The product was obtained by short path distillation under vacuum (bp 70 to 77° C. at 0.09 mmHg) to give the product ethyl 4-ethoxy-2-oxopent-3-enoate (36.5 g, 47.3 mmol, 79% yield) as a light yellow oil.
$^1$H NMR (400 MHz, CHLOROFORM-d) δ 6.24 (s, 1H), 4.32 (q, J=7.2 Hz, 2H), 4.02 (q, J=6.9 Hz, 2H), 2.41 (s, 3H), 1.41 (t, J=7.1 Hz, 3H), 1.39 (t, J=7.2 Hz, 3H). MS (ES)+ m/e 186.8 [M+H]$^+$, 208.8 M+Na$^+$.

b) ethyl 5-cyano-4-methyl-6-oxo-1,6-dihydropyridine-2-carboxylate

To a stirred solution of ethyl 4-ethoxy-2-oxopent-3-enoate (22.5 g, 121 mmol) and 2-cyanoacetamide (9.0 g, 107 mmol) in acetone (250 mL) was added potassium carbonate (15.8 g, 114 mmol). The reaction was refluxed (85° C. oil bath) for 10 hr (the reaction formed a thick ppt. in a deep red solution). The slurry was added to cold 1 N HCl (230 mL) in ice. After stirring for 30 min the suspension was filtered, washed with water and dried under vacuum to give the product ethyl 5-cyano-4-methyl-6-oxo-1,6-dihydropyridine-2-carboxylate (14.51 g, 70.4 mmol, 65.7% yield) as a light pink solid.
$^1$H NMR (400 MHz, DMSO-$d_6$) δ12.60 (br. s., 1H), 7.05 (br. s., 1H), 4.34 (q, J=7.1 Hz, 2H), 2.45 (s, 3H), 1.32 (t, J=7.1 Hz, 3H). MS (ES)+ m/e 206.8 [M+H]$^+$.

c) ethyl 5-cyano-6-methoxy-4-methylpicolinate

To a stirred suspension of ethyl 5-cyano-4-methyl-6-oxo-1,6-dihydropyridine-2-carboxylate (2.0 g, 9.70 mmol) in CH$_2$Cl$_2$ (25 mL) was added trimethyloxonium tetrafluoroborate (2.0 g, 13.52 mmol). The reaction was rinsed down with CH$_2$Cl$_2$ and stirred at RT for 24 h. (The reaction eventually cleared up.) To the reaction was added 1 N NaOH (75 mL). After stirring for 10 minutes the mixture was poured into a separatory funnel. The CH$_2$Cl$_2$ phase was removed, dried (Na2SO$_4$), filtered and concentrated under vacuum. Purification by silica gel chromatography (Analogix SF25-40 g, 50 to 100% CH$_2$Cl$_2$ in hexanes) gave the product ethyl 5-cyano-6-methoxy-4-methylpicolinate (1.13 g, 5.13 mmol, 52.9% yield) as a white solid. $^1$H NMR (400 MHz, DMSO-$d_6$) δ 7.75 (s, 1H), 4.37 (q, J=7.1 Hz, 2H), 4.03 (s, 3H), 2.55 (s, 3H), 1.33 (t, J=7.2 Hz, 3H). MS (ES)+ m/e 221.2 [M+H]$^+$.

d) 5-cyano-6-methoxy-4-methylpicolinic acid

To a stirred solution of ethyl 5-cyano-6-methoxy-4-methylpicolinate (1.0 g, 4.54 mmol) in MeOH (30 mL) and THF (10 mL) was added 6 N NaOH (2 mL, 12.00 mmol). The suspension was heated to 60° C. and stirred for 2 h. (The reaction cleared up right away.) LCMS indicated that the reaction was complete. The reaction was cooled to RT and concentrated to near dryness. The slurry was neutralized with 6 N HCl (2 mL) diluted with water, filtered, washed with water and dried under vacuum to give the product 5-cyano-6-methoxy-4-methylpicolinic acid (0.76 g, 3.95 mmol, 87% yield) as a white solid. $^1$H NMR (400 MHz, DMSO-$d_6$) δ 13.65 (br. s., 1H), 7.73 (s, 1H), 4.03 (s, 3H), 2.54 (s, 3H). MS (ES)+ m/e 192.9 [M+H]$^+$.

e) tert-butyl (5-cyano-6-methoxy-4-methylpyridin-2-yl)carbamate

To a stirred solution of 5-cyano-6-methoxy-4-methylpicolinic acid (0.75 g, 3.90 mmol) in tert-butanol (25 mL) was added triethylamine (0.7 mL, 5.02 mmol). After the reaction became clear DPPA (1 mL, 4.64 mmol) was added dropwise over 5 minutes. The reaction was slowly heated to 100° C. and stirred for 4 h. The reaction was cooled to RT and evaporated to dryness under vacuum. Purified by silica gel chromatography (Analogix, SF25-60 g, 0 to 20% EtOAc in hexanes) to give, after trituration and filtration from hexanes, the product tert-butyl (5-cyano-6-methoxy-4-methylpyridin-2-yl)carbamate (0.61 g, 2.317 mmol, 59.4% yield) as a white solid. $^1$H NMR (400 MHz, DMSO-$d_6$) δ 10.20 (s, 1H), 7.44 (s, 1H), 3.91 (s, 3H), 2.40 (s, 3H), 1.48 (s, 9H). MS (ES)+ m/e 264.0 [M+H]$^+$.

f) tert-butyl (5-(aminomethyl)-6-methoxy-4-methylpyridin-2-yl)carbamate

A clear solution of tert-butyl (5-cyano-6-methoxy-4-methylpyridin-2-yl)carbamate (0.60 g, 2.279 mmol) in HOAc (5 mL) and ethanol (20 mL) was treated on an H-Cube apparatus (50 psi, 40° C., 1 mL/min, Raney Nickel cartridge) for 18 h. LCMS showed that the reaction was complete (86% pure). The reaction was evaporated to dryness under vacuum. Purified by silica gel chromatography (Analogix, SF25-60 g, 0 to 12% (5% NH$_4$OH/MeOH) in CH$_2$Cl$_2$). The pure fractions were combined and evaporated to dryness under vacuum to give the product tert-butyl (5-(aminomethyl)-6-methoxy-4-methylpyridin-2-yl)carbamate (0.42 g, 1.571 mmol, 68.9% yield) as a white solid. $^1$H NMR (400 MHz, DMSO-d$_6$) δ 9.33 (s, 1H), 7.16 (s, 1H), 3.80 (s, 3H), 3.57 (s, 2H), 2.28 (s, 3H), 1.46 (s, 9H). MS (ES)+ m/e 268.1 [M+H]$^+$.

Intermediate 18

[5-(Aminomethyl)-4-methyl-6-(methyloxy)-2-pyridinyl]methanol

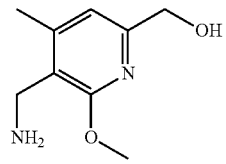

a) 6-(Hydroxymethyl)-2-methoxy-4-methylnicotinonitrile

To a stirred suspension of ethyl 5-cyano-6-methoxy-4-methylpicolinate (5.0 g, 22.70 mmol) and calcium chloride (10 g, 90 mmol) in tetrahydrofuran (50 mL) and ethanol (50.0 mL) at 0° C. in an ice bath was added sodium borohydride (2.5 g, 66.1 mmol). The reaction was slowly allowed to warm to RT and stirred for 18 h. A large amount of ppt. formed and LCMS showed that the reaction was complete. An equal volume of EtOAc was added and the reaction stirred for 1 h. The suspension was filtered through a pad of Celite and washed with EtOAc. The filtrate was transferred to a separatory funnel, washed with aq. NH$_4$Cl, brine, dried (Na$_2$SO$_4$), filtered and concentrated under vacuum. Purification by silica gel chromatography (Analogix, SF40-120 g, 0 to 30% EtOAc in CH$_2$Cl$_2$) gave the product 6-(hydroxymethyl)-2-methoxy-4-methylnicotinonitrile (3.75 g, 21.05 mmol, 93% yield) as a white solid. $^1$H NMR (400 MHz, DMSO-d$_6$) δ 7.16 (s, 1H), 5.61 (t, J=5.8 Hz, 1H), 4.51 (d, J=5.8 Hz, 2H), 3.94 (s, 3H), 2.47 (s, 3H). MS (ES)+ m/e 179.1 [M+H]$^+$.

b) (5-(Aminomethyl)-6-methoxy-4-methylpyridin-2-yl)methanol

A clear solution of 6-(hydroxymethyl)-2-methoxy-4-methylnicotinonitrile (0.50 g, 2.81 mmol) in HOAc (5 mL) and Ethanol (20 mL) was treated on an H-Cube apparatus (50 psi, 40° C., 1 mL/min, Raney Nickel cartridge) for 18 hr overnight. LCMS showed that the reaction was complete (crude contained 57% product and 43% dimeric side product). The reaction was evaporated to dryness under vacuum. Purified by silica gel chromatography (Analogix, SF25-40 g, 0 to 12% (5% NH$_4$OH in MeOH) in CH$_2$Cl$_2$) (step gradient to 8% to elute off the dimeric side product then to 12% to elute off the product). The pure fractions were combined and evaporated to dryness under vacuum to give the product (5-(aminomethyl)-6-methoxy-4-methylpyridin-2-yl)methanol (0.30 g, 1.646 mmol, 58.7% yield) as a white solid. MS (ES)+ m/e 183.1 [M+H]$^+$, 166.1 [M+H]$^+$-NH$_3$.

Intermediate 19 tert-Butyl ((5-(aminomethyl)-6-methoxy-4-methylpyridin-2-yl)methyl)carbamate

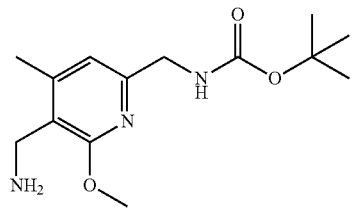 [SMILES: COc1nc(CNC(=O)OC(C)(C)C)cc(C)c1CN]

a) 6-((1,3-Dioxoisoindolin-2-yl)methyl)-2-methoxy-4-methylnicotinonitrile

To a stirred solution of 6-(hydroxymethyl)-2-methoxy-4-methylnicotinonitrile (1.50 g, 8.42 mmol), phthalimide (1.3 g, 8.84 mmol) and triphenylphosphine (2.3 g, 8.77 mmol) in tetrahydrofuran (THF) (50 mL) at 0° C. in an ice bath was added dropwise DIAD (1.8 mL, 9.26 mmol). Within minutes a white suspension formed. Additional THF (~50 mL) was added to allow stirring. The reaction was allowed to warm to RT and stirred for 3 h. LCMS showed that the reaction was complete. The reaction was evaporated to dryness under vacuum. The remaining solid was triturated with a small volume of EtOAc, filtered, washed with a small volume of EtOAc, then dried under vacuum to give the product 6-((1,3-dioxoisoindolin-2-yl)methyl)-2-methoxy-4-methylnicotinonitrile (2.12 g, 6.90 mmol, 82% yield) as a white solid. $^1$H NMR (400 MHz, DMSO-d$_6$) δ 8.00-7.92 (m, 2H), 7.92-7.87 (m, 2H), 7.15 (s, 1H), 4.86 (s, 2H), 3.74 (s, 3H), 2.43 (s, 3H). MS (ES)+ m/e 308.2 [M+H]$^+$.

b) tert-Butyl ((5-cyano-6-methoxy-4-methylpyridin-2-yl)methyl)carbamate

To a stirred fine suspension of 6-((1,3-dioxoisoindolin-2-yl)methyl)-2-methoxy-4-methylnicotinonitrile (2.1 g, 6.83 mmol) in Ethanol (100 mL) was added hydrazine monohydrate (1.4 ml, 28.9 mmol). The reaction was stirred at RT for 18 h. LCMS showed that the reaction was done. The thick white suspension was filtered, pressed dry, washed with EtOH, and the filtrate evaporated to dryness under vacuum. The remaining solid was taken up in Dichloromethane (50 ml), filtered to remove additional insoluble material, and washed with CH$_2$Cl$_2$. To the clear filtrate with stirring was added Boc$_2$O (1.809 ml, 7.79 mmol). After stirring at RT for 1 hr LCMS showed that the reaction was complete. The reaction was concentrated under vacuum and purified by silica gel chromatography (Analogix, SF25-60, 0 to 10% EtOAc in hexanes). The pure fractions were combined and evaporated to dryness to give the product tert-butyl ((5-cyano-6-methoxy-4-methylpyridin-2-yl)methyl)carbamate (1.42 g, 5.12 mmol, 74.9% yield) as a white solid. $^1$H NMR (400 MHz, DMSO-d$_6$) δ 7.48 (t, J=6.1 Hz, 1H), 6.91 (s, 1H), 4.16 (d, J=6.1 Hz, 2H), 3.96 (s, 3H), 2.45 (s, 3H), 1.41 (s, 9H). MS (ES)+ m/e 278.2 [M+H]$^+$.

c) tert-Butyl ((5-(aminomethyl)-6-methoxy-4-methylpyridin-2-yl)methyl)carbamate A clear solution of tert-butyl ((5-cyano-6-methoxy-4-methylpyridin-2-yl)methyl)carbamate (0.65 g, 2.344 mmol) in HOAc (5 mL) and Ethanol (20 mL) was treated on an H-Cube apparatus (50 psi, 40° C., 1 mL/min, Raney Nickel cartridge) for 18 hr overnight. LCMS showed that the reaction was complete. The reaction was evaporated to dryness under vacuum. Purified by silica gel chromatography (Analogix, SF25-60 g, 0 to 10% (5% NH$_4$OH/MeOH) in CH$_2$Cl$_2$). The pure fractions were combined and evaporated to dryness under vacuum to give the product tert-butyl ((5-(aminomethyl)-6-methoxy-4-methylpyridin-2-yl)methyl)carbamate (0.58 g, 2.061 mmol, 88% yield) as a clear thick oil. $^1$H NMR (400 MHz, DMSO-d$_6$) δ 7.31 (t, J=6.1 Hz, 1H), 6.63 (s, 1H), 4.06 (d, J=6.3 Hz, 2H), 3.84 (s, 3H), 3.61 (s, 2H), 2.29 (s, 3H), 1.53 (br. s., 2H), 1.41 (s, 9H). MS (ES)+ m/e 282.2 [M+H]$^+$.

Intermediate 20

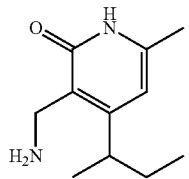

The title compound was prepared in the same manner as described for 3-(aminomethyl)-4-ethyl-6-methyl-2(1H)-pyridinone (Intermediate 10c). LCMS (ES+) m/z=195.22 (M+H). $^1$H NMR (DMSO-d$_6$, 400 MHz): δ 0.809-0.774 (t, 3H, J=6.8 Hz), 1.113-1.097 (d, 3H, J=6.4 Hz), 1.504-1.468 (t, 2H, J=7.2 Hz), 2.184 (s, 3H), 2.839-2.822 (d, 1H, J=6.8 Hz), 3.822 (s, 2H), 6.059 (s, 1H), 8.315 (bs, 2H).

Intermediate 21

2-Methoxy-5-(tributylstannyl)thiazole

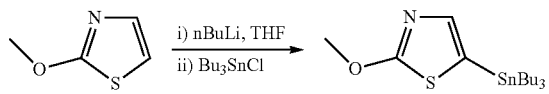

To a stirred solution of 2-methoxythiazole (5 g, 43.4 mmol) in tetrahydrofuran (THF) (50 mL) was added n-BuLi (35.3 mL, 56.4 mmol) and the contents stirred at –78° C. After 15 min, tributylchlorostannane (14.13 mL, 52.1 mmol) was added and the mixture stirred with warming to room temperature over a 3 h period. The reaction mixture was quenched with water (20 mL) and the contents extracted with ether (25 mL). The organic layer was separated and dried over anhydrous sodium sulphate, filtered, and the filtrate concentrated in vacuo to afford the crude product (6 g). The crude product was purified by silica gel column chromatography (eluent: 2% EtOAc/Hexane) to afford 2-methoxy-5-(tributylstannyl)

thiazole (4 g, 22%) as yellow liquid. $^1$H NMR (400 MHz, CDCl$_3$-d$_3$) δ ppm 0.90-0.98 (m, 9H), 1.05-1.15 (m, 6H), 1.30-1.40 (m, 6H), 1.50-1.65 (m, 6H), 4.04 (s, 3H), 7.03 (s, 1H). LCMS (ES) [M+H]$^+$ 405.99.

Intermediate 22

2-Methoxythiazol-5-yl)boronic acid

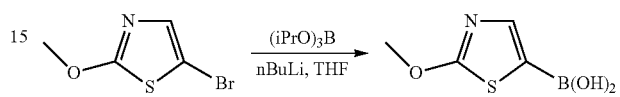

To a stirred solution of 5-bromo-2-methoxythiazole (500 mg, 2.58 mmol) in tetrahydrofuran (THF) (15 mL) was added triisopropyl borate (0.598 mL, 2.58 mmol) and then n-BuLi (2.416 mL, 3.87 mmol), and the contents stirred at –78° C. for 3 h. The reaction mixture was quenched with aq.NH$_4$Cl (5 mL) and the contents extracted with ethyl acetate (15 mL). The organic layer was separated and dried over anhydrous sodium sulphate, filtered, and the filtrate concentrated in vacuo to afford the title compound (400 mg), which was used without further purification.

Assay Protocol

Part A. Compound Preparation
1. Prepare 10 mM stock of compounds from solid in 100% DMSO.
2. In a 384-well Greiner plate (Cat #781280), plate compounds in columns 1 and 13.
3. Set up the Multiprobe instrument to do an 11 point serial dilution (1:3 dilution, columns 6 and 18 are DMSO controls).
4. Stamp 100 mL of compound from the dilution plate into reaction plates (Corning, 384-well, Cat#3706) using the Hummingbird.

Part B. Reagent Preparation
1. Prepare 2× assay buffer mix with final concentrations of 50 mM Tris pH 8, 5 mM MgCl$_2$, 4 mM DTT, 0.00185% Tween-20, and 7 µg/ml Hela nucleosomes (GRITS36431).
2. Prepare 2×EZH2 (GRITS37108) enzyme mix in assay buffer with a final enzyme concentration of 10 nM.
3. Prepare 2× mix of hot and cold SAM in ddH$_2$O with final concentrations of 0.24 µM cold SAM (Sigma) and 0.02 µCi/µL $^3$H-SAM (Perkin Elmer).
4. Prepare 500 µM SAH quench solution in ddH$_2$O with 5-10 drops of concentrated HCl to dissolve.
5. Prepare 6 mg/ml RNA binding SPA beads (Perkin Elmer) suspended in 0.2 M Citric Acid, pH 2.2

| Reagent | Stock | 2× [Final] | [Final] |
|---|---|---|---|
| Mix 1. Assay Buffer Mix | | | |
| Tris pH 8 | 1000 mM | 100 mM | 50 mM |
| MgCl$_2$ | 1000 mM | 10 mM | 5 mM |
| DTT | 1000 mM | 8 mM | 4 mM |

-continued

| Reagent | Stock | 2× [Final] | [Final] |
|---|---|---|---|
| Tween-20 | 1% | 0.0037% | 0.00185% |
| Hela nucleosomes In ddH$_2$0 | 492 µg/ml | 14 µg/ml | 7 µg/ml |
| Mix 2. Enzyme Mix | | | |
| EZH2 GRITS37108 In Mix 1. Buffer | 1351 nM | 20 nM | 10 nM |
| Mix 3. SAM Substrate Mix, 500 nM total SAM | | | |
| Cold SAM | 100 µM | 0.48 µM | 0.24 µM |
| $^3$H-SAM | 0.55 | 0.04 | 0.02 |
| 78 Ci/mmol | µCi/µL | µCi/µL | µCi/µL |
| DMSO | 100% | 2% | 1% |
| In ddH$_2$0 | | | |

*Assay is run at apparent substrate $K_m$ for SAM and nucleosomes.

Part C. Assay Reaction in 384-Well Corning 3706 Plates
In reaction plates stamped with 100 nL compound, 1. Dispense 5 µL no enzyme control (assay buffer mix) to column 18 of plates.
2. Dispense 5 µL of enzyme mix to the remaining wells in the plate. Centrifuge plate to mix and incubate at room temperature for 30 minutes.
3. Dispense 5 µL of substrate mix to all wells to initiate the reactions. Centrifuge plate to mix and incubate at room temperature for 2 hours.
4. Quench the reactions with 10 µL of 500 µM SAH solution (250 µM final).
5. Dispense 10 µL of 6 mg/ml RNA binding SPA beads prepared in 0.2 M citric acid, pH 2.2 using the Evolution instrument. Continuously shake the beads while adding to plates to prevent beads from settling.
6. Seal the plates with Perkin Elmer top seals and allow the beads to equilibrate in the plate for at least 30 minutes at room temperature.
7. Centrifuge the plates >2000 RPM (657 rcf) for one minute. Read plates in Microbeta after at least 5 hours incubation. Plates can be read immediately, but signal increases over time.

Reagent addition can be done manually or with automated liquid handler.

*The final DMSO concentration in this assay is 1%.
*The positive control is in column 6; negative control is in column 18.
*Final starting concentration of compounds is 100 µM.

Part D. Data Analysis

The data was analyzed using a 2-parameter IC$_{50}$ fit in Grafit program. The IC$_{50}$ range for the exemplified compounds was recorded to fall in a range between 16-3981 nm.

Compounds of this invention are not expected to have an unacceptable untoward effect when used in accordance with the teachings herein above and when used in accordance with appropriate and usual scientific and medical practice The foregoing examples are provided to illustrate the invention and are not intended to limit it in any way. What is reserved to the inventors is to be determined by reference to the claims.

What is claimed is:
1. A compound of formula (I):

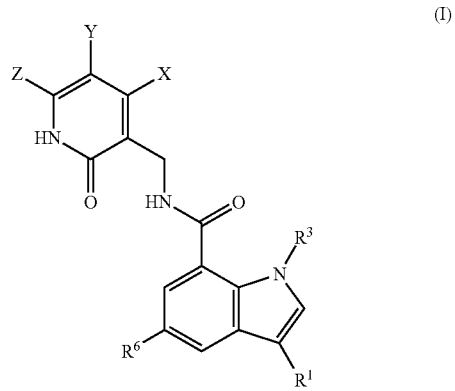

wherein
X and Z are selected independently from the group consisting of hydrogen, (C$_1$-C$_8$)alkyl, (C$_2$-C$_8$)alkenyl, (C$_2$-C$_8$)alkynyl, unsubstituted or substituted (C$_3$-C$_8$)cycloalkyl, unsubstituted or substituted (C$_3$-C$_8$)cycloalkyl-(C$_1$-C$_8$)alkyl or —(C$_2$-C$_8$)alkenyl, unsubstituted or substituted (C$_5$-C$_8$)cycloalkenyl, unsubstituted or substituted (C$_5$-C$_8$)cycloalkenyl-(C$_1$-C$_8$)alkyl or —(C$_2$-C$_8$)alkenyl, (C$_6$-C$_{10}$)bicycloalkyl, unsubstituted or substituted heterocycloalkyl, unsubstituted or substituted heterocycloalkyl-(C$_1$-C$_8$)alkyl or —(C$_2$-C$_8$)alkenyl, unsubstituted or substituted aryl, unsubstituted or substituted aryl-(C$_1$-C$_8$)alkyl or —(C$_2$-C$_8$)alkenyl, unsubstituted or substituted heteroaryl, unsubstituted or substituted heteroaryl-(C$_1$-C$_8$)alkyl or —(C$_2$-C$_8$)alkenyl, halo, cyano, —COR$^a$, —CO$_2$R$^a$, —CONR$^a$R$^b$, —CONR$^a$NR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —NR$^a$NR$^a$C(O)OR$^a$, —OR$^a$, —OC(O)R$^a$, and —OC(O)NR$^a$R$^b$;

Y is H or halo;

R$^1$ is (C$_1$-C$_8$)alkyl, (C$_2$-C$_8$)alkenyl, (C$_2$-C$_8$)alkynyl, unsubstituted or substituted (C$_3$-C$_8$)cycloalkyl, unsubstituted or substituted (C$_3$-C$_8$)cycloalkyl-(C$_1$-C$_8$)alkyl or —(C$_2$-C$_8$)alkenyl, unsubstituted or substituted (C$_5$-C$_8$)cycloalkenyl, unsubstituted or substituted (C$_5$-C$_8$)cycloalkenyl-(C$_1$-C$_8$)alkyl or —(C$_2$-C$_8$)alkenyl, unsubstituted or substituted (C$_6$-C$_{10}$)bicycloalkyl, unsubstituted or substituted heterocycloalkyl, unsubstituted or substituted heterocycloalkyl-(C$_1$-C$_8$)alkyl or —(C$_2$-C$_8$)alkenyl, unsubstituted or substituted aryl, unsubstituted or substituted aryl-(C$_1$-C$_8$)alkyl or -(C$_2$-C$_8$)alkenyl, unsubstituted or substituted heteroaryl, unsubstituted or substituted heteroaryl-(C$_1$-C$_8$)alkyl or —(C$_2$-C$_8$)alkenyl, —COR$^a$, —CO$_2$R$^a$, —CONR$^a$R$^b$, or —CONR$^a$NR$^a$R$^b$;

R$^3$ is hydrogen, (C$_1$-C$_8$)alkyl, cyano, trifluoromethyl, —NR$^a$R$^b$, or halo;

R$^6$ is selected from the group consisting of hydrogen, halo, (C$_1$-C$_8$)alkyl, (C$_2$-C$_8$)alkenyl, (C$_2$-C$_8$)alkynyl, unsubstituted or substituted (C$_3$-C$_8$)cycloalkyl, unsubstituted or substituted (C$_3$-C$_8$)cycloalkyl-(C$_1$-C$_8$)alkyl, unsubstituted or substituted (C$_5$-C$_8$)cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, $CO_2R^a$, —$CONR^aR^b$, C—$ONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, $NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, $NR^aNR^aC(O)OR^a$, —$OR^a$, —$OC(O)R^a$, and —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, $CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1-C_4$)alkyl, and heteroaryl($C_1-C_4$)alkyl;

wherein any aryl or heteroaryl moiety of said aryl, heteroaryl, aryl($C_1-C_4$)alkyl, or heteroaryl($C_1-C_4$)alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, $CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; and $R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)($(C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)($(C_1-C_4)$alkyl), —$SO_2(C_1-C_4)$alkyl, —$SO_2NH_2$, —$SO_2NH(C_1-C_4)$alkyl, and —$SO_2N((C_1-C_4)$alkyl)($(C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)($(C_1-C_4)$alkyl)amino, hydroxyl, oxo, $(C_1-C_4)$alkoxy, and $(C_1-C_4)$alkoxy($C_1-C_4$)alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a pharmaceutically acceptable salt thereof.

2. The compound or pharmaceutically acceptable salt according to claim 1 wherein:

X and Z are selected independently from the group consisting of $(C_1-C_8)$alkyl, $(C_3-C_8)$cycloalkyl, heterocycloalkyl, aryl, heteroaryl, —$NR^aR^b$, and —$OR^a$;

Y is H or F;

$R^1$ is selected from the group consisting of $(C_1-C_8)$alkyl, $(C_3-C_8)$cycloalkyl, heterocycloalkyl, aryl, and heteroaryl;

$R^3$ is selected from the group consisting of hydrogen, $(C_1-C_8)$alkyl, cyano, trifluoromethyl, —$NR^aR^b$, and halo;

$R^6$ is selected from the group consisting of hydrogen, halo, cyano, trifluoromethyl, amino, $(C_1-C_8)$alkyl, $(C_3-C_8)$cycloalkyl, aryl, heteroaryl, acylamino, $(C_2-C_8)$alkynyl, arylalkynyl, heteroarylalkynyl; —$SO_2R^a$, —$SO_2NR^aR^b$, and —$NRaSO_2R^b$;

wherein any $(C_1-C_8)$alkyl, $(C_3-C_8)$cycloalkyl, $(C_2-C_8)$alkynyl, arylalkynyl, or heteroarylalkynyl group is optionally substituted by 1, 2 or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SRa$, —$SOR^a$, —$SO_2R^a$, —$SO_2NR^aR^b$, nitro, —$NR^aR^b$, $NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1-C_4$)alkyl, and heteroaryl($C_1-C_4$)alkyl; and $R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)($(C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)($(C_1-C_4)$alkyl), —$SO_2(C_1-C_4)$alkyl, —$SO_2NH_2$, —$SO_2NH(C_1-C_4)$alkyl, and —$SO_2N((C_1-C_4)$alkyl)($(C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)($(C_1-C_4)$alkyl)amino, hydroxyl, oxo, $(C_1-C_4)$alkoxy, and $(C_1-C_4)$alkoxy($C_1-C_4$)alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

wherein any aryl or heteroaryl group is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

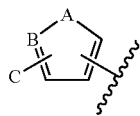
(1)

wherein in (1),
A is O, NH, or S; B is CH or N, and C is hydrogen or $C_1$-$C_8$ alkyl; or

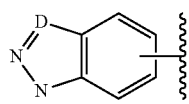
(2)

wherein in (2),
D is N or C optionally substituted by hydrogen or $C_1$-$C_8$ alkyl; or

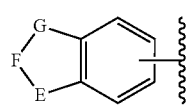
(3)

wherein in (3),
E is NH or $CH_2$; F is O or CO; and G is NH or $CH_2$; or

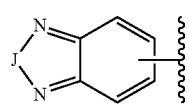
(4)

wherein in (4),
J is O, S or CO; or

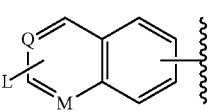
(5)

wherein in (5),
Q is CH or N;
M is CH or N; and
L/(5) is hydrogen, halo, amino, cyano, ($C_1$-$C_8$)alkyl, ($C_3$-$C_8$)cycloalkyl, —COR$^a$, CO$_2$R$^a$, CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$;
wherein any ($C_1$-$C_8$)alkyl or ($C_3$-$C_8$)cycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; or

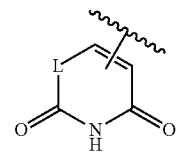
(6)

wherein in 6,
L/(6) is NH or $CH_2$; or

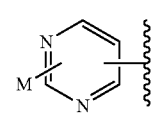
(7)

wherein in 7,
M/(7) is hydrogen, halo, amino, cyano, ($C_1$-$C_8$)alkyl, ($C_3$-$C_8$)cycloalkyl, heterocycloalkyl, —COR$^a$, CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$;
wherein any ($C_1$-$C_8$)alkyl, ($C_3$-$C_8$)cycloalkyl, or heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; or

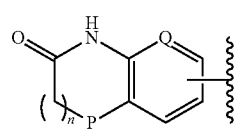
(8)

wherein in (8),
P is $CH_2$, NH, O, or S; Q/(8) is CH or N; and n is 0-2; or

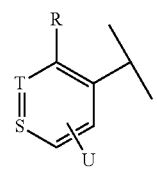
(9)

wherein in (9),
S/(9) and T/(9) are each CH, or S/(9) is CH and T(9) is N, or S/(9) is N and T/(9) is CH;
R is hydrogen, amino, methyl, trifluoromethyl, or halo;
U is hydrogen, halo, amino, cyano, nitro, trifluoromethyl, ($C_1$-$C_8$)alkyl, ($C_3$-$C_8$)cycloalkyl, COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, NR$^a$SO$_2$NR$^a$R$^b$, —NR$^a$NR$^a$R$^b$, —NR$^a$NR$^a$C(O)R$^b$, —OR$^a$, or 4-(1H-pyrazol-4-yl);

wherein any (C₁-C₈)alkyl or (C₃-C₈)cycloalkyl group is optionally substituted by 1, 2 or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, and —OC(O)NR$^a$R$^b$.

3. The compound or pharmaceutically acceptable salt according to claim 1 wherein:

X and Z are selected independently from the group consisting of (C₁-C₈)alkyl, (C₃-C₈)cycloalkyl, heterocycloalkyl, aryl, heteroaryl, —NR$^a$R$^b$, and —OR$^a$;

Y is H;

R$^1$ is (C₁-C₈)alkyl, (C₃-C₈)cycloalkyl, or heterocycloalkyl;

R$^3$ is hydrogen, (C₁-C₈)alkyl or halo;

R$^6$ is hydrogen, halo, cyano, trifluoromethyl, amino, (C₁-C₈)alkyl, (C₃-C₈)cycloalkyl, aryl, heteroaryl, acylamino, (C₂-C₈)alkynyl, arylalkynyl, heteroarylalkynyl, —SO₂R$^a$, —SO₂NR$^a$R$^b$, or NR$^a$SO₂R$^b$;

wherein any (C₁-C₈)alkyl, (C₃-C₈)cycloalkyl, (C₂-C₈)alkynyl, arylalkynyl, or heteroarylalkynyl group is optionally substituted by 1, 2 or 3 groups independently selected from halo, (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, —OC(O)NR$^a$R$^b$, heterocycloalkyl, aryl, heteroaryl, aryl(C₁-C₄)alkyl, and heteroaryl(C₁-C₄)alkyl; and R$^a$ and R$^b$ are each independently hydrogen, (C₁-C₈)alkyl, (C₂-C₈)alkenyl, (C₂-C₈)alkynyl, (C₃-C₈)cycloalkyl, (C₅-C₈)cycloalkenyl, (C₆-C₁₀)bicycloalkyl, heterocycloalkyl, aryl, or heteroaryl, wherein said (C₁-C₈)alkyl, (C₂-C₈)alkenyl, (C₂-C₈)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C₁-C₄)alkoxy, amino, (C₁-C₄)alkylamino, ((C₁-C₄)alkyl)((C₁-C₄)alkyl)amino, —CO₂H, —CO₂(C₁-C₄)alkyl, —CONH₂, —CONH(C₁-C₄)alkyl, —CON((C₁-C₄)alkyl)((C₁-C₄)alkyl), —SO₂(C₁-C₄)alkyl, —SO₂NH₂, —SO₂NH(C₁-C₄)alkyl, and —SO₂N((C₁-C₄)alkyl)((C₁-C₄)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C₁-C₄)alkyl, (C₁-C₄)haloalkyl, amino, (C₁-C₄)alkylamino, ((C₁-C₄)alkyl)((C₁-C₄)alkyl)amino, hydroxyl, oxo, (C₁-C₄)alkoxy, and (C₁-C₄)alkoxy(C₁-C₄)alkyl, wherein said ring is optionally fused to a (C₃-C₈)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C₃-C₈)cycloalkyl, heterocycloalkyl, aryl, or heteroaryl ring;

wherein any aryl or heteroaryl is selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine, or another aryl or heteroaryl group as follows:

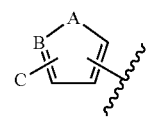

(1)

wherein in (1),
A is O, NH, or S; B is CH or N, and C is hydrogen or C₁-C₈ alkyl; or

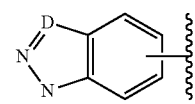

(2)

wherein in (2),
D is N or C optionally substituted by hydrogen or C₁-C₈ alkyl; or

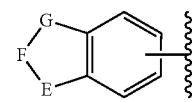

(3)

wherein in (3),
E is NH or CH₂; F is O or CO; and G is NH or CH₂; or

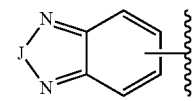

(4)

wherein in (4),
J is O, S or CO; or

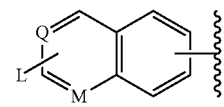

(5)

wherein in (5),
Q is CH or N;
M is CH or N; and
L/(5) is hydrogen, halo, amino, cyano, (C₁-C₈)alkyl, (C₃-C₈)cycloalkyl, —COR$^a$, —CO₂R$^a$, CONR$^a$R$^b$, —CONR$^a$NR$^a$R$^b$, —SO₂R$^a$, —SO₂NR$^a$R$^b$, —NR$^a$R$^b$, —NR$^a$C(O)R$^b$, —NR$^a$SO₂R$^b$, NR$^a$SO₂NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$;

wherein any (C₁-C₈)alkyl or (C₃-C₈)cycloalkyl group is optionally substituted by 1, 2 or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$;

or

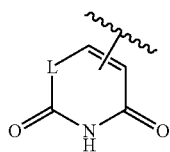
(6)

wherein in 6,
L/(6) is NH or CH$_2$; or

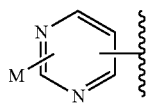
(7)

wherein in 7,
M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$;
wherein any (C$_1$-C$_8$)alkyl, (C$_3$-C$_8$)cycloalkyl, or heterocycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; or

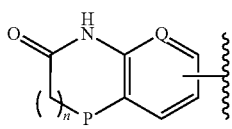
(8)

wherein in (8),
P is CH$_2$, NH, O, or S; Q/(8) is CH or N; and n is 0-2; or

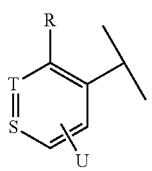
(9)

wherein in (9),
S/(9) and T(9) are each CH, or S/(9) is CH and T(9) is N, or S/(9) is N and T/(9) is CH;
R is hydrogen, amino, methyl, trifluoromethyl, or halo;

U is hydrogen, halo, amino, cyano, nitro, trifluoromethyl, (C$_1$-C$_8$)alkyl, (C$_3$-C$_8$)cycloalkyl, COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, NR$^a$SO$_2$NR$^a$R$^b$, —NR$^a$NR$^a$R$^b$, —NR$^a$NR$^a$C(O)R$^b$, —OR$^a$, or 4-(1H-pyrazol-4-yl);
wherein any (C$_1$-C$_8$)alkyl or (C$_3$-C$_8$)cycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$.

4. The compound or pharmaceutically acceptable salt according to claim 1 wherein:
X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;
Y is H;
Z is methyl, ethyl, n-propyl, isopropyl, trifluoromethyl, or benzyl;
R$^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;
R$^3$ is H, methyl, ethyl, propyl, isopropyl or Br; and
R$^6$ is methyl, cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 24-dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl, 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(4-methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

5. The compound according to claim 1 which is:
5-Bromo-N-[(4,6-dimethyl-2-oxo-1,2-dihydro-3-pyridinyl)methyl]-1-methyl-3-(1-methylethyl)-1H-indole-7-carboxamide;
5-{4-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;
5-{3-[(Dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;
N-[(4,6-Dimethyl-2-oxo-1,2-dihydro-3-pyridinyl)methyl]-1-methyl-3-(1-methylethyl)-5-[6-(4-methyl-1-piperazinyl)-3-pyridinyl]-1H-indole-7-carboxamide;
5-Bromo-1-methyl-3-(1-methylethyl)-N-[(6-methyl-2-oxo-4-propyl-1,2-dihydro-3-pyridinyl)methyl]-1H-indole-7-carboxamide;
5-{3-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;
5-{4-[(Dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;
1-Methyl-3-(1-methylethyl)-N-[(6-methyl-2-oxo-4-propyl-1,2-dihydro-3-pyridinyl)methyl]-5-[6-(4-methyl-1-piperazinyl)-3-pyridinyl]-1H-indole-7-carboxamide;
N-[(4,6-Dimethyl-2-oxo-1,2-dihydro-3-pyridinyl)methyl]-1-methyl-3-(1-methylethyl)-5-(6-methyl-3-pyridinyl)-1H-indole-7-carboxamide;
N-[(4,6-Dimethyl-2-oxo-1,2-dihydro-3-pyridinyl)methyl]-1-methyl-3-(1-methylethyl)-5-[6-(1-piperazinyl)-3-pyridinyl]-1H-indole-7-carboxamide;
5-(2-Amino-5-pyrimidinyl)-N-[(4,6-dimethyl-2-oxo-1,2-dihydro-3-pyridinyl)methyl]-1-methyl-3-(1-methylethyl)-1H-indole-7-carboxamide;
5-(6-Amino-3-pyridinyl)-N-[(4,6-dimethyl-2-oxo-1,2-dihydro-3-pyridinyl)methyl]-1-methyl-3-(1-methylethyl)-1H-indole-7-carboxamide;
N-[(4,6-Dimethyl-2-oxo-1,2-dihydro-3-pyridinyl)methyl]-1-methyl-3-(1-methylethyl)-5-(2-methyl-5-pyrimidinyl)-1H-indole-7-carboxamide;
N-[(4,6-Dimethyl-2-oxo-1,2-dihydro-3-pyridinyl)methyl]-1-methyl-3-(1-methylethyl)-5-(4-piperidinyl)-1H-indole-7-carboxamide;
N-[(4,6-Dimethyl-2-oxo-1,2-dihydro-3-pyridinyl)methyl]-1-methyl-3-(1-methylethyl)-5-(1-methyl-4-piperidinyl)-1H-indole-7-carboxamide;
N-[(4,6-Dimethyl-2-oxo-1,2-dihydro-3-pyridinyl)methyl]-1-methyl-3-(1-methylethyl)-5-(4-morpholinyl)-1H-indole-7-carboxamide;
N-[(4-Ethyl-6-methyl-2-oxo-1,2-dihydro-3-pyridinyl)methyl]-1-methyl-3-(1-methylethyl)-5-(4-morpholinyl)-1H-indole-7-carboxamide;
5-Bromo-N-[(4,6-dimethyl-2-oxo-1,2-dihydro-3-pyridinyl)methyl]-3-(1-methylethyl)-1H-indole-7-carboxamide;
N-((4,6-Dimethyl-2-oxo-1,2-dihydropyridin-3-yl)methyl)-3-isopropyl-1-methyl-5-(methylsulfonyl)-1H-indole-7-carboxamide;
N-[(4,6-Dimethyl-2-oxo-1,2-dihydro-3-pyridinyl)methyl]-1-methyl-3-(1-methylethyl)-5-(methyloxy)-1H-indole-7-carboxamide;
N-((4-Benzyl-6-methyl-2-oxo-1,2-dihydropyridin-3-yl)methyl)-5-bromo-3-isopropyl-1-methyl-1H-indole-7-carboxamide;
5-Bromo-1-methyl-3-(1-methylethyl)-N-[(4-methyl-2-oxo-1,2-dihydro-3-pyridinyl)methyl]-1H-indole-7-carboxamide;
N-[(4,6-Dimethyl-2-oxo-1,2-dihydro-3-pyridinyl)methyl]-1-methyl-3-(1-methylethyl)-1H-indole-7-carboxamide;
5-Cyclopropyl-N-((4,6-dimethyl-2-oxo-1,2-dihydropyridin-3-yl)methyl)-3-isopropyl-1-methyl-1H-indole-7-carboxamide; or
N-((4,6-Dimethyl-2-oxo-1,2-dihydropyridin-3-yl)methyl)-3-isopropyl-5-(2-methoxythiazol-5-yl)-1-methyl-1H-indole-7-carboxamide;
or a pharmaceutically acceptable salt thereof.

6. The compound according to claim 1 which is:
5-bromo-N-[(4,6-dimethyl-2-oxo-1,2-dihydro-3-pyridinyl)methyl]-1-methyl-3-(1-methylethyl)-1H-indole-7-carboxamide;
5-{4-[(dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;
5-{3-[(dimethylamino)methyl]phenyl}-N-[(4,6-dimethyl-2-oxo-1,2-dihydro-3-pyridinyl)methyl]-1-methyl-3-(1-methylethyl)-1H-indole-7-carboxamide;
N-[(4,6-dimethyl-2-oxo-1,2-dihydro-3-pyridinyl)methyl]-1-methyl-3-(1-methylethyl)-5-[6-(4-methyl-1-piperazinyl)-3-pyridinyl]-1H-indole-7-carboxamide;
5-bromo-1-methyl-3-(1-methylethyl)-N-[(6-methyl-2-oxo-4-propyl-1,2-dihydro-3-pyridinyl)methyl]-1H-indole-7-carboxamide;
5-{3-[(dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;
5-{4-[(dimethylamino)methyl]phenyl}-1-methyl-3-(1-methylethyl)-N-[(6-methyl-2-oxo-4-propyl-1,2-dihydro-3-pyridinyl)methyl]-1H-indole-7-carboxamide;
1-methyl-3-(1-methylethyl)-N-[(6-methyl-2-oxo-4-propyl-1,2-dihydro-3-pyridinyl)methyl]-5-[6-(4-methyl-1-piperazinyl)-3-pyridinyl]-1H-indole-7-carboxamide;
N-[(4,6-dimethyl-2-oxo-1,2-dihydro-3-pyridinyl)methyl]-1-methyl-3-(1-methylethyl)-5-(6-methyl-3-pyridinyl)-1H-indole-7-carboxamide;
N-[(4,6-dimethyl-2-oxo-1,2-dihydro-3-pyridinyl)methyl]-1-methyl-3-(1-methylethyl)-5-[6-(1-piperazinyl)-3-pyridinyl]-1H-indole-7-carboxamide;
5-(2-amino-5-pyrimidinyl)-N-[(4,6-dimethyl-2-oxo-1,2-dihydro-3-pyridinyl)methyl]-1-methyl-3-(1-methylethyl)-1H-indole-7-carboxamide;
5-(6-amino-3-pyridinyl)-N-[(4,6-dimethyl-2-oxo-1,2-dihydro-3-pyridinyl)methyl]-1-methyl-3-(1-methylethyl)-1H-indole-7-carboxamide;
N-[(4,6-dimethyl-2-oxo-1,2-dihydro-3-pyridinyl)methyl]-1-methyl-3-(1-methylethyl)-5-(2-methyl-5-pyrimidinyl)-1H-indole-7-carboxamide;
N-[(4,6-dimethyl-2-oxo-1,2-dihydro-3-pyridinyl)methyl]-1-methyl-3-(1-methylethyl)-5-(4-piperidinyl)-1H-indole-7-carboxamide;
N-[(4,6-dimethyl-2-oxo-1,2-dihydro-3-pyridinyl)methyl]-1-methyl-3-(1-methylethyl)-5-(1-methyl-4-piperidinyl)-1H-indole-7-carboxamide;
N-[(4,6-dimethyl-2-oxo-1,2-dihydro-3-pyridinyl)methyl]-1-methyl-3-(1-methylethyl)-5-(4-morpholinyl)-1H-indole-7-carboxamide;
N-[(4-ethyl-6-methyl-2-oxo-1,2-dihydro-3-pyridinyl)methyl]-1-methyl-3-(1-methylethyl)-5-(4-morpholinyl)-1H-indole-7-carboxamide; or
5-bromo-N-[(4,6-dimethyl-2-oxo-1,2-dihydro-3-pyridinyl)methyl]-3-(1-methylethyl)-1H-indole-7-carboxamide;
or a pharmaceutically acceptable salt thereof.

7. A pharmaceutical composition comprising the compound or pharmaceutically acceptable salt according to claim 1 and a pharmaceutically acceptable excipient.

\* \* \* \* \*